(12) United States Patent
Haneda et al.

(10) Patent No.: US 6,787,534 B2
(45) Date of Patent: Sep. 7, 2004

(54) SULFONAMIDE-CONTAINING HETEROCYCLIC COMPOUNDS

(75) Inventors: Toru Haneda, Ibaraki (JP); Akihiko Tsuruoka, Ibaraki (JP); Junichi Kamata, Ibaraki (JP); Tadashi Okabe, Ibaraki (JP); Keiko Takahashi, Ibaraki (JP); Kazumasa Nara, Ibaraki (JP); Shinichi Hamaoka, Ibaraki (JP); Norihiro Ueda, Ibaraki (JP); Toshiaki Wakabayashi, Ibaraki (JP); Yasuhiro Funahashi, Ibaraki (JP); Taro Semba, Ibaraki (JP); Naoko Hata, Ibaraki (JP); Yuji Yamamoto, Ibaraki (JP); Yoichi Ozawa, Ibaraki (JP); Naoko Tsukahara, Ibaraki (JP); Takashi Owa, Ibaraki (JP)

(73) Assignee: Eisai Co., Ltd., Tokyo (JP)

( * ) Notice: Subject to any disclaimer, the term of this patent is extended or adjusted under 35 U.S.C. 154(b) by 0 days.

(21) Appl. No.: 10/149,253

(22) PCT Filed: Dec. 27, 2000

(86) PCT No.: PCT/JP00/09326

§ 371 (c)(1),
(2), (4) Date: Jun. 10, 2002

(87) PCT Pub. No.: WO01/47891

PCT Pub. Date: Jul. 5, 2001

(65) Prior Publication Data

US 2003/0144507 A1 Jul. 31, 2003

(30) Foreign Application Priority Data

Dec. 28, 1999 (JP) .......................... 11-375489

(51) Int. Cl.[7] .................. A61K 31/33; A61K 31/44; A61K 31/47; C07D 213/00; C07D 215/00
(52) U.S. Cl. .................. 514/183; 514/277; 514/299; 514/311; 514/345; 514/351; 546/1; 546/152; 546/159; 546/290; 546/293; 546/294
(58) Field of Search .................. 514/183, 277, 514/299, 311, 345, 351; 546/1, 152, 159, 290, 293, 294

(56) References Cited

U.S. PATENT DOCUMENTS

| | | | |
|---|---|---|---|
| 3,046,122 A | 7/1962 | Sus | 96/33 |
| 3,157,684 A | 11/1964 | Marrian et al. | 266/461 |
| 3,801,321 A | 4/1974 | Evans et al. | 96/48 |
| 4,333,760 A | 6/1982 | Zimmerman | 43/54 |
| 4,826,528 A | 5/1989 | Mengel et al. | 71/92 |
| 4,881,969 A | 11/1989 | Saupe et al. | |
| 4,931,433 A | 6/1990 | Tolman | |
| 5,089,633 A | 2/1992 | Powers et al. | 549/285 |
| 5,529,999 A | 6/1996 | Ray et al. | |
| 5,852,190 A | 12/1998 | Pascal et al. | |
| 6,300,342 B1 | 10/2001 | Heckel et al. | |

FOREIGN PATENT DOCUMENTS

| | | |
|---|---|---|
| DE | 9688 | 11/1943 |
| DE | 197 27 117 A | 1/1999 |

(List continued on next page.)

OTHER PUBLICATIONS

G. Dubois et al, Bull. De la Soc. de Pharm. de Boedeaux, 127/1–4,29–36(1988).*

(List continued on next page.)

Primary Examiner—Richard L. Raymond
Assistant Examiner—Sudhaker B. Patel
(74) Attorney, Agent, or Firm—Birch, Stewart, Kolasch & Birch, LLP

(57) ABSTRACT

The present invention provides a sulfonamide- or sulfonylurea-containing heterocyclic compounds. Specifically, it provides a heterocyclic compound represented by the formula (I), a pharmacologically acceptable salt thereof or a hydrate of them.

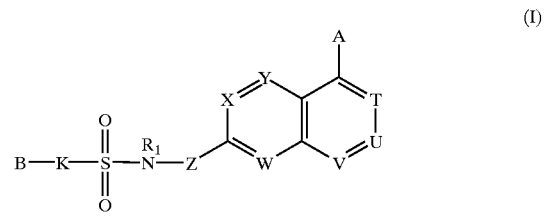

(I)

In the formula, A is hydrogen atom, a halogen atom, a C1–C4 alkyl or alkoxy group which may be substituted with a halogen atom, or cyano group; B is an optionally substituted aryl group or monocyclic heteroaryl group, or:

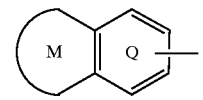

(wherein, the ring Q is an aromatic ring which may have nitrogen atom; and the ring M is a ring sharing a double bond with the ring Q, which ring may have a heteroatom; and the rings Q and M may share nitrogen atom); K is a single bond; T, W, X and Y are the same as or different from each other and each is =C(D)— (wherein, D is hydrogen or a halogen atom) or nitrogen atom; U and V are the same as or different from each other and each is =C(D)—, nitrogen atom, —CH$_2$—, oxygen atom or —CO—; Z is a single bond or —CO—NH—; and R$_1$ is hydrogen atom, etc.

9 Claims, No Drawings

FOREIGN PATENT DOCUMENTS

| | | | |
|---|---|---|---|
| EP | 0 266 949 A1 | | 5/1988 |
| EP | 329012 A2 | | 8/1989 |
| EP | 329012 | * | 8/1989 |
| EP | 398283 A1 | | 11/1990 |
| EP | 496332 A1 | | 7/1992 |
| EP | 496332 | * | 7/1992 |
| EP | 0 610 653 A1 | | 8/1994 |
| EP | 672662 A1 | | 9/1995 |
| EP | 672662 | * | 9/1995 |
| EP | 1 258 252 A | | 11/2002 |
| GB | 662798 | | 12/1951 |
| GB | 1492029 A | | 11/1977 |
| JP | 59-220733 A | | 12/1984 |
| JP | 62-426 A | | 1/1987 |
| JP | 1-254682 A | | 10/1989 |
| JP | 02-149562 A | | 6/1990 |
| JP | 03-150560 A | | 6/1991 |
| JP | 7-138493 A | | 5/1995 |
| JP | 7-267936 A | | 10/1995 |
| WO | 96/11690 A1 | | 4/1996 |
| WO | 9715308 | * | 5/1997 |
| WO | WO 97/15308 A1 | | 5/1997 |
| WO | WO 99/01434 A1 | | 1/1999 |

OTHER PUBLICATIONS

Antonello et al, Gazzetta Chim. Italiana, 91, 926–32(1961).*
Gopalcharo et al (J. Scientific & Ind. Res., Section B:Physical ASc.,21/B/4,183–5(1962).*
Gopalchari, R., J. Scientific and Ind. Tesearch, Section B, Physical Sciences, 21B/4,183–5(1962).*
Antonello C., Chemical Abstr. CASREACT AN:45964.*
Gopalchari et al, CAPLUS DN 57:62647., also cited as CAOLD CA57:12432d.*
Chittum et al, Chemical Abstract CAPLUS DN 81:91322.*
Kotler et al,Chemical Abstract CAPLUS DN 65:56729.*
Charles J. Matson et al,J. Med. Chem.,22/7,816–23(1979).*
Chemical Abstrac DN 127:17703 See Compound with CAS RN #3357-75-4.*
Cecil Textbook of Medicine, Edited by Bennett and Plum, W.B.Saunders Co, 1996,p. g1004-1010.*
Uckum et al,"Structure bases Design of Novel Anti–cancer Agts.", Current Cancer Targets,1,59–71(2001).*
Scozzafava et al, PubMed Abstract 1268681, also cited as Curr. Med. Chgem. 10/11,925–53,(Jun. 2003).*
Gross et al,PubMed Abstract 11407307,also cited as Int.Immunopharmacol. 1/6,1131–9,(Jun. 2001).*
Hayashi et al, PubMed Abstract 12118089,also cited as Lab.Invest. 82/7,871–80,(Jul. 2002).*
Sartippour et al,PubMed 12680218,also cited as Anticancer res. 23/1A,231–4,(Jan. 2003).*
G.Dubois et al,"Synth. of trimethylsiulylquinolines", Chemical Abstract CASREACT AN 112:179084.*
Pellerano, C.: Ann. Chim. (ROME) , vol. 53, No. 12, 1963, pp. 1850–1859, XP009001877.
Donia, S.G.: Egypt. J. Pharm. Sci., vol. 34, No. 4–6, 1993, pp. 529–538, XP001120378.
Gopalchari, R.: J. Sci. Ind. Res. (India), vol. 21B, No. 4, 1962, pp. 183–185, XP009001866.
Miura Y. et al.: Heterocycles, vol. 35, No. 2, 1993, pp. 693–699, XP009001888.
Pagani, G. et al.: IL FARMACO—Ed. Sci., vol. 26, No. 2, 1971, pp. 118–131, XP009001889.
Database Chemcats, Chemical Abstract Service, Columbus, Ohio, US; retrieved from STN, XP002223294.
Cordi et al., Bioorg. Med. Chem., vol. 3, No. 2, pp. 129–141 (1995).
Ried et al., Justus Liebigs Ann. Chem., vol. 707, pp. 242–249 (1967).
Bailey et al., J. Chem. Soc. C, No. 22, pp. 3769–3678 (1971).
Erickson et al., J. Med. Chem., vol. 22, No. 7, pp. 816–823 (1979).
Menon et al., J. Sci. Industr. Res., vol. 21B, pp. 20–23, Jan. 1962.
A. S. Bailey et al., J. Chem. Soc., Perkin Transactions 1, 1975, pp. 420–424.
J. J. Howbert et al., J. Med. Chem., 1190, vol. 33, No. 9, pp. 2393–2407.
R. R. Wilkening et al., Bioorganic & Medicinal Chemistry Letters, 9 (1999), 673–678.
M. Ohtani et al., J. Med. Chem., vol. 39, No. 15, pp. 2871–2873, Jul. 19, 1996.
D. Hellwinkel et al., Chem Ber. 118, 66–85 (1985).
A. A. El–Maghraby et al., J. Chem. Tech. Biotechnol. 1983, 33A, 25–32.
J. Buzniak et al., Polish Journal of Chemistry, vol. 55, No. 9, 1981, pp. 1923–1927.
C. A. Obafemi, Phosphorus and Sulfur, 1982, vol. 13, pp. 119–131.
A. M. Islam et al., Egypt J. Chem., 19, No. 6, pp. 945–960 (1976).
J. G. Krause, Chemistry and Industry, 1978, pp. 271–272.
A. A. Abou Ouf et al., J. Drug Res. Egypt, vol. 6, No. 2, pp. 123–129 (1974).
G. Paglietti et al., Annali di Chimica, 62, pp. 128–143, 1972.
M. M. El–Kerdawy et al., U.A.R. J. Chem., 13, No. 2, pp. 231–234 (1970).
V. G. Buchmann et al., Journal fur Praktische Chemie, vol. 4, No. 16, 1962, pp. 152–165.
E. R. Ward et al., J. Amer. Chem. Soc., Abstracts, 1961, pp. 4866–4872.
J. R. Stevens et al., J. Am. Chem. Soc., vol. 68, 1946, pp. 1035–1039.
Z. Budesinsky et al., Collection Czechoslov Chem. Comm., vol. 37, pp. 887–895, 1972.
S. V. Litvinenko et al., Chemistry of Heterocyclic Compounds, vol. 30, No. 3, 1994, pp. 340–344.
R. Niedlein et al., Archiv der Pharmazie, vol. 304, No. 10, 1971, pp. 763–773.
H. J. Rodda, J. Chem. Soc., pp. 3509–3512, 1956.
J. L. Neumeyer et al., J. Med. Chem., 1970, vol. 13, No. 4, pp. 613–616.
D. V. Prasad et al., Synthetic Communications, 18(8), 881–887 (1988).
H. W. Bersch, et al., Arzneimittel–Forschung, vol. 5, No. 3, 1955, pp. 116–120.

* cited by examiner

SULFONAMIDE-CONTAINING HETEROCYCLIC COMPOUNDS

This application is the national phase under 35 U.S.C. §371 of PCT International Application No. PCT/JP00/09326 which has an International filing date of Dec. 27, 2000, which designated the United States of America.

TECHNICAL FIELD

The present invention relates to a sulfonamide-containing heterocyclic compound which is useful as a medicament and to an antiangiogenic effect thereof. Further, it relates to an antitumor agent, a cancer metastasis suppressor, a therapeutic agent for diabetic retinopathy, a therapeutic agent for rheumatic arthritis and a therapeutic agent for hematoma on the basis of an antiangiogenic effect.

PRIOR ART

It has become clear that there is a close relation between proliferation of cancer and angiogenesis. Thus, when angiogenesis is not generated at the site of cancer, the cancer remains in a state of dormant tumor. However, it has become clarified that, when angiogenesis is generated, oxygen and nutrients in blood are supplied to the tumor whereby proliferation and metastasis of cancer are promoted resulting in a clinically malignant state. Accordingly, it is expected that, when angiogenesis of cancer is suppressed, proliferation and metastasis of cancer can be suppressed. Since angiogenetic vessels are composed of endothelial cells and interstitial cells of the host, target of the antiangiogenic agent is not cancer cells but such normal cells of the host. Because of the fact that the cancer cells are not a direct target, efficacy to the cancer which does not respond to known anticancer agents can be expected as well and, in addition, it is presumed that the possibility of occurrence of tolerant cancer which is a big problem in cancer therapy is little. In addition, angiogenesis is a tumor-specific phenomenon and, in mature individuals, it is limited to the formation of endometrium, etc. accompanied by a menstrual cycle. Accordingly, its adverse effect is thought to be little as compared with known anticancer drugs. Recently, it has been experimentally proved in preclinical tests that antiangiogenic agents are able to suppress and further to reduce the proliferation of cancer in the cancer-transplanted models and that tolerant cancer is not generated and, in clinical tests, the correlation between angiogenesis and malignization of many solid cancers such as breast cancer, prostatic cancer, lung cancer and cancer of the colon has been shown.

In cancer tissues, apoptosis and proliferation of cancer cells continuously occur and it has been known that, depending upon the balance between them, progressive cancer or dormant tumor is resulted. An antiangiogenic agent does not directly kill the cancer cells but cuts off the nutrient sources so that the said balance is inclined to apoptosis inducing dormant tumor or reduction in cancer whereby it is a drug which can be expected to exhibit an excellent effect (prolongation of life, inhibition of recurrence and suppression of metastasis) by a long-term therapy.

In a preclinical stage, there are antiangiogenic agents by various action mechanisms but, since their antitumor effect in a preclinical stage is insufficient, their usefulness in clinical stage is still doubtful and, therefore, there has been a brisk demand for antiangiogenic agents where the effect is reliable.

It has been also known that angiogenesis participates in retinopathy or retinitis. When blood vessel is proliferated in retina, eyesight gets worse and, when progressed, blindness is resulted. Effective therapeutic drugs have been demanded.

In GB 662798, hydroxy- and acyloxy-phenylsulfonylamino-substituted quinoline and quinoxaline are disclosed, but relates to antiviral agents and are different from the present invention. In J. Sci. Ind. Res., sect. B, 21(1962), 3-p-toluenesulfonylamino-8-hydroxyquinoline is disclosed. Though, there is no description relating to an antiangiogenic effect. In JP-A 1-254682, 1,8-naphthylidine and pyrido[2,3-d]pyrimidine derivatives having a substituted sulfonamide are disclosed, but relates to herbicides and are different from the present invention. In JP-A 62-426 and 7-267936, sulfonamidequinoxaline derivatives having antitumor activity are disclosed. Though, there is no description relating to an antiangiogenic effect.

Accordingly, an object of the present invention is to provide a novel sulfonamide-containing heterocyclic compound that has an excellent an antiangiogenic effect and has a different structure from those of conventional antiangiogenic agent. Another object of the present invention is to provide an intermediate of the compound and a pharmaceutical composition containing the compound as an active ingredient.

DISCLOSURE OF THE INVENTION

The present inventors have made intensive investigations for an antiangiogenic agent. As a result, they have found that a novel sulfonamide-containing heterocyclic compound has an excellent antiangiogenic effect and has an excellent effect as a pharmaceutical drug. Thus, they have accomplished the present invention.

Specifically, the present invention provides a sulfonamide-containing heterocyclic compound represented by the formula (I), a pharmacologically acceptable salt thereof or a hydrate of them.

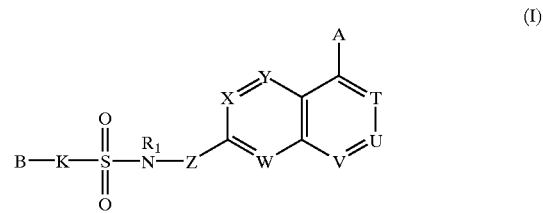

(I)

In the formula:

A is hydrogen atom, a halogen atom, hydroxyl group, a C1–C4 alkyl group or alkoxy group which may be substituted with a halogen atom, cyano group, —(CO)$_k$NR$^2$R$^3$ (wherein, R$^2$ and R$^3$ are the same as or different from each other and each means hydrogen atom or a C1–C4 alkyl group which may be substituted with a halogen atom; and k means 0 or 1), a C2–C4 alkenyl group or alkynyl group which may have a substituent, or a phenyl group or phenoxy group which may have a substituent selected from the following group A;

B is an aryl group or monocyclic heteroaryl group which may have a substituent selected from the following group A, or

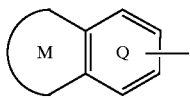

(wherein, the ring Q is an aromatic ring which may have one or two nitrogen atoms; the ring M is an unsaturated C5–C12 monocyclic or polycyclic ring which shares a double bond with the ring Q, and the ring may have 1 to 4 hetero atoms selected from nitrogen atom, oxygen atom and sulfur atom; the ring Q and the ring M may share nitrogen atom with each other; and the ring Q and the ring M may each have a substituent selected from the following group A);

K is a single bond or —$(CR^4R^5)m$— (wherein, $R^4$ and $R^5$ are the same as or different from each other and each means hydrogen atom or a C1–C4 alkyl group; and m is an integer of 1 or 2);

T, W, X and Y are the same as or different from each other and each means =C(D)— (wherein D is hydrogen atom, a halogen atom, hydroxyl group, a C1–C4 alkyl group or alkoxy group which may be substituted by a halogen atom, cyano group, —$(CO)nNR^6R^7$ (wherein $R^6$ and $R^7$ are the same as or different from each other and each means hydrogen atom or a C1–C4 alkyl group which may be substituted with a halogen atom; and n means 0 or 1), or a C2–C4 alkenyl group or alkynyl group which may have a substituent), or nitrogen atom;

U and V are the same as or different from each other and each means =C(D)— (wherein, D has the same meaning as defined above), nitrogen atom, —$CH_2$—, oxygen atom or —CO—;

Z is a single bond or —CO—NH—;

R1 is hydrogen atom or a C1–C4 alkyl group; and

══ means a single or double bond,

Group A a halogen atom, hydroxyl group, a C1–C4 alkyl group or alkoxy group which may be substituted by a halogen atom, cyano group, —$R^8R^9N(NH)p$— (wherein $R^8$ and $R^9$ are the same as or different from each other and each means hydrogen atom or a C1–C4 alkyl group which may be substituted with a halogen atom; and p means 0 or 1, and $R^8$ and $R^9$ may be combined with the nitrogen atom to which they bound to form a 5- or 6-membered ring which may include nitrogen atom, oxygen atom or sulfur atom and may have a substituent), an aminosulfonyl group which may be substituted with one or two C1–C4 alkyl groups, an optionally substituted C1–C8 acyl group, a C1–C4 alkyl-S(O)s-C1–C4 alkylene group (wherein s means an integer of 0, 1 or 2), a phenylsulfonylamino group which may have a C1–C4 alkyl or a substituent, —$(CO)qNR^{10}R^{11}$ (wherein $R^{10}$ and $R^{11}$ are the same as or different from each other and each means hydrogen atom or a C1–C4 alkyl group which may be substituted with an amino group which may be substituted with a halogen atom or a C1–C4 alkyl group; and q means 0 or 1), or an aryl or heteroaryl group which may have a substituent, provided that when U is oxygen atom, V means —CO— or —$CH_2$—; when V is oxygen atom, U means —CO— or —$CH_2$—; and the following cases 1) where only one of T, U, V, W, X and Y is nitrogen atom; and A and D are both hydrogen atoms, 2) where T, U, V, W, X and Y are all nitrogen atoms, 3) where Y and W are nitrogen atoms; T, U, V and X are =C(D1)— (wherein D1 means hydrogen atom, methyl group, a halogen atom, trifluoromethyl group or methoxy group); and Z is a single bond; and A is hydrogen atom, methyl group, a halogen atom, trifluoromethyl group or methoxy group, 4) where W is nitrogen atom; T, U, V, X and Y are =C(D2)— (wherein D2 means hydrogen atom); K and Z are single bonds; A is hydroxyl group; and B is p-toluenesulfonylamino group, 5) where V and W are nitrogen atoms and 6) where T, V and W are nitrogen atoms are excluded.

The present invention provides a halogen-substituted quinoline compound represented by the following formula:

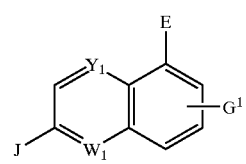

(II)

(wherein, $Y_1$ and $W_1$ are different from each other and each means nitrogen atom or =$C(D^3)$— (wherein, $D^3$ is hydrogen atom, a halogen atom, hydroxyl group, a C1–C4 alkyl group or alkoxy group which may be substituted with a halogen atom, cyano group or —$(CO)nNR^6R^7$ (wherein, $R^6$ and $R^7$ are the same as or different from each other and each means hydrogen atom or a C1–C4 alkyl group which may be substituted with a halogen atom; and n means 0 or 1)); E is a halogen atom, cyano group or a C1–C4 alkyl group which may be substituted with a halogen atom; J is an amino group which may have a protecting group or a carboxyl group which may have a protecting group; $G^1$ is hydrogen atom, a halogen atom, hydroxyl group, a C1–C4 alkyl group or alkoxy group which may be substituted with a halogen atom, cyano group, —$(CO)tNR^{14}R^{15}$ (wherein, $R^{14}$ and $R^{15}$ are the same as or different from each other and each means hydrogen atom or a C1–C4 alkyl group which may be substituted with a halogen atom; and t means 0 or 1), or an optionally substituted C2–C4 alkenyl group or alkynyl group which is a production intermediate of the compound represented by the above formula (I), or a salt thereof.

In addition, the present invention provides a process for producing a compound represented by the formula:

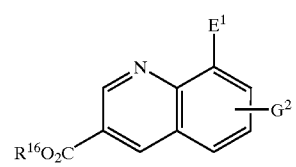

(IV)

(wherein $E^1$ is a halogen atom; $R^{16}$ is a carboxyl-protecting group; $G^2$ is hydrogen atom, a halogen atom, hydroxyl group or a C1–C4 alkyl group or alkoxy group which may be substituted with a halogen atom), which comprises the step of reducing a compound represented by the formula:

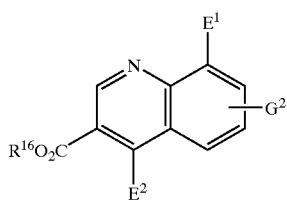

(III)

(wherein E¹ is a halogen atom; E² is chlorine atom or bromine atom; R¹⁶ is a carboxyl-protecting group; G² is hydrogen atom, a halogen atom, hydroxyl group, or a C1–C4 alkyl group or alkoxy group which may be substituted with a halogen atom) with tin, zinc or iron.

The compound represented by the above formula (IV) is a compound of the above formula (II) wherein $Y_1$ is nitrogen atom; $W_1$ is =CH—; E is a halogen atom; J is a carboxyl group having a protecting group; and G¹ is hydrogen atom, a halogen atom, hydroxyl group, or a C1–C4 alkyl group or alkoxy group which may be substituted with a halogen atom.

The present invention provides an antiangiogenic agent, an anti-cancer agent, a cancer metastasis suppressor, a therapeutic agent for diabetic retinopathy, a therapeutic agent for rheumatic arthritis or a therapeutic agent for hematoma, comprising the sulfonamide-containing heterocyclic compound represented by the above formula (I) a pharmacologically acceptable salt thereof or a hydrate of them, as an active ingredient.

The present invention provides a method for preventing or treating a disease against which an antiangiogenic effect is efficacious for the prevention or treatment of cancer, cancer-metastasis, diabetic retinopathy, rheumatic arthritis or hematoma, by administering a pharmacologically effective amount of the sulfonamide-containing heterocyclic compound represented by the above formula (I), a pharmacologically acceptable salt thereof or a hydrate of them to a patient.

The present invention provides use of the sulfonamide-containing heterocyclic compound represented by the above formula (I), a pharmacologically acceptable salt thereof or a hydrate of them, for producing an antiangiogenic agent, an anti-cancer agent, a cancer metastasis suppressor, a therapeutic agent for diabetic retinopathy, a therapeutic agent for rheumatic arthritis or a therapeutic agent for hematoma.

In the present invention, the "aromatic ring which may have one or two nitrogen atoms" in ring Q is an aromatic hydrocarbon or a 6-membered aromatic heterocycle including one or two nitrogen atoms. Examples of such aromatic rings in ring Q are benzene, pyridine, pyrimidine, pyrazine, pyridazine etc. The "unsaturated C5–C12 monocyclic or polycyclic ring, which may have one to four hetero atoms selected from nitrogen atom, oxygen atom and sulfur atom" as ring M means an unsaturated monocyclic or polycyclic ring which shares a double bond with ring Q and includes aromatic hydrocarbon rings such as benzene and naphthalene; unsaturated hydrocarbon rings such as cyclopentene, cyclohexene, cycloheptene, cyclooctene, cyclopentadienes, cycloheptadienes and cyclooctadienes; and unsaturated heterocyclic rings such as tetrahydropyridine, pyrrole, furan, thiophene, oxazole, isoxazole, thiazole, isothiazole, pyrazole, imidazole, triazole, pyridine, pyrimidine, pyrazine, pyridazine, triazine, indole, isoindole, quinoline, isoquinoline, indazolidine, naphthylidine, benzofuran, benzopyran, benzothiophene, benzimidazole, benzoxazole, benzothiazole, pyrrolopyridine, pyridopyrimidine and imidazopyridine. The phrase "ring Q and ring M may share one nitrogen atom with each other" means the case where the nitrogen atom is present at the condensation position between the two rings, and such rings include, for example, indazolidine, imidazo[1,2-a]pyridine, imidazo[1,5-a]pyridine and pyrazolo[1,5-a]pyrimidine.

In the present invention, the C1–C4 alkyl group in $R_1$, $R^4$ and $R^5$, and the C1–C4 alkyl group in the C1–C4 alkyl group which may be substituted with a halogen atom in A, D, $R_1$, $R^2$, $R^3$, $R^6$, $R^7$, $R^8$, $R^9$, $R^{10}$, $R^{11}$, $R^{12}$, $R^{13}$, $R^{14}$, $R^{15}$, $G^1$, $G^2$ and Group A include linear or branched alkyl groups having 1 to 4 carbon atoms such as methyl group, ethyl group, n-propyl group, isopropyl group, n-butyl group, isobutyl group, sec-butyl group and tert-butyl group. The phrase "which may be substituted with a halogen atom" means that each of these alkyl groups may be substituted by a halogen atom(s) selected from fluorine atom, chlorine atom, bromine atom and iodine atom. Such halogen-substituted alkyl groups include, for example, monofluoromethyl group, monochloromethyl group, difluoromethyl group, trifluoromethyl group, 1- or 2-monofluoroethyl group, 1- or 2-monochloroethyl group, 1- or 2-monobromoethyl group, 1,2-difluoroethyl group, 1,2-dichloroethyl group, 1,1,2,2,2-pentafluoroethyl group and 3,3,3-trifluoropropyl group. Among them, monofluoromethyl group, difluoromethyl group, trifluoromethyl group, 1- or 2-monofluoroethyl group, 1,2-difluoroethyl group and 1,1,2,2,2-pentafluoroethyl group are preferred.

In the present invention, the C1–C4 alkoxy group in the C1–C4 alkoxy group which may be substituted with a halogen atom in A, D and Group A includes linear or branched alkoxy groups having 1 to 4 carbon atoms, such as methoxy group, ethoxy group, n-propoxy group, isopropoxy group, n-butyloxy group, isobutyloxy group, sec-butyloxy group and tert-butyloxy group. The phrase "which may be substituted with a halogen atom" means that each of these alkoxy groups may be substituted by a halogen atom(s) selected from fluorine atom, chlorine atom, bromine atom and iodine atom. Such halogen-substituted alkoxy groups include, for example, monofluoromethoxy group, difluoromethoxy group, trifluoromethoxy group, 1- or 2-monofluoroethoxy group, 1- or 2-monochloroethoxy group, 1- or 2-monobromoethoxy group, 1,2-difluoroethoxy group, 1,1,2,2,2-pentafluoroethoxy group and 3,3,3-trifluoropropoxy group. Among them, monofluoromethoxy group, difluoromethoxy group, trifluoromethoxy group, 1- or 2-monofluoroethoxy group, 1,2-difluoroethoxy group and 1,1,2,2,2-pentafluoroethoxy group are preferred.

In the present invention, the C2–C4 alkenyl group or alkynyl group in A and D includes alkenyl groups or alkynyl groups having 2 to 4 carbon atoms, such as vinyl group, allyl group, 2- or 3-butenyl group, 1,3-butanedienyl group, ethynyl group, 2-propynyl group, 2-methylethynyl group, and 2- or 3-butynyl group.

The aryl group in B and Group A in the present invention means and includes aromatic hydrocarbon groups such as phenyl group and naphthyl group. The heteroaryl group means and includes monocyclic and polycyclic rings each containing one or more nitrogen atoms, oxygen atoms and sulfur atoms. Such heteroaryl groups include, for example, pyrrolyl, imidazolyl group, pyrazolyl group, triazolyl group, furyl group, thienyl group, oxazolyl group, isoxazolyl group, thiazolyl group, isothiazolyl group, thiadiazolyl group, pyridyl group, pyrimidyl group, pyrazyl group, indolyl group, indolizinyl group, benzimidazolyl group, benzothiazolyl group, benzoxazolyl group, quinolinyl group, isoquinolinyl group, quinazolinyl group, and phthalazinyl group.

The phrase "$R^8$ and $R^9$ may be combined with the nitrogen atom to which they bound to form a 5- or 6-membered ring which may include nitrogen atom, oxygen atom or sulfur atom" in $R^8$ and $R^9$ in the present invention means that $R^8$ and $R^9$ together with the nitrogen atom to which they bound form a ring such as pyrrolidinyl group, piperidinyl group, morpholino group, thiomorpholino group and piperazinyl group.

In the present invention, the C1–C4 alkyl group in the aminosulfonyl group which may be substituted with one or two C1–C4 alkyl groups, an optionally substituted C1–C8 acyl group, the C1–C4 alkyl-S(O)s-C1–C4 alkylene group, C1–C4 alkyl- or phenyl-sulfonylamino group which phenyl group may have a substituent and the C1–C4 alkyl group which may be substituted with an amino group which may be substituted with a halogen atom or a C1–C4 alkyl group in Group A mean and include the same alkyl groups as mentioned above. The alkylene group includes, for example, methylene group, ethylene group, propylene group and butylene group, as well as methylmethylene group, 1- or 2-methylethylene group, 1-, 2- or 3-methylpropylene group and dimethylmethylene group.

The C1–C8 alkanoyl group means, for example, formyl group, acetyl group, propionyl group, butyryl group, isobutyryl group, valeryl group, benzoyl group etc.

The protecting group in the "amino group which may have a protecting group" in J in the present invention is not specifically limited as long as it is generally used as an amino-protecting group in organic synthesis. Such protecting groups include, but are not limited to, benzyloxycarbonyl group, t-butoxycarbonyl group, formyl group, acetyl group, chloroacetyl group, 2,2,2-trichloroethyl group, benzylidene group, benzhydryl group and trityl group. The protecting group in the carboxyl group which may have a protecting group and the carboxy-protecting group in $R^{16}$ are not specifically limited and can be any protecting groups as long as they are generally used as carboxyl-protecting groups in organic synthesis. Such protecting groups include, but are not limited to, methyl group, ethyl group, propyl group, isopropyl group, t-butyl group, methoxymethyl group, 2,2,2-trichloroethyl group, pivaloyloxymethyl group and benzyl group.

In the present invention, the substituent in the phrase "which may have a substituent" means and includes the aforementioned halogen atoms, C1–C4 alkyl groups or alkoxy groups which may be substituted with a halogen atom, hydroxyl group, hydroxy-C1–C4 alkyl groups, amino groups which may be substituted with one or two C1–C4 alkyl groups, C2–C4 alkenyl groups or alkynyl groups, cyano group, C1–C8 acyl groups, aminosulfonyl groups which may be substituted with one or two C1–C4 alkyl groups, carboxyl group, C1–C4 alkoxy-carbonyl groups, and carbamoyl groups which may be substituted with one or two C1–C4 alkyl groups.

The sulfonamide-containing heterocyclic compounds represented by the above formula (I) may form salts with acids or bases. The present invention also includes the salts of the compound (I). Such salts with acids include, for example, inorganic acid salts such as hydrochlorate, hydrobromate and sulfate; and salts with an organic acid such as acetic acid, lactic acid, succinic acid, fumaric acid, maleic acid, citric acid, benzoic acid, methanesulfonic acid and p-toluenesulfonic acid. Examples of the salt with a base are an inorganic salt such as sodium salt, potassium salt and calcium salt, and that with an organic base such as triethylamine, arginine or lysine.

It goes without saying that the present invention further includes all the optical isomers, if any, as well as a hydrate of these compounds. Further, the compounds which show an antiangiogenic effect produced from the compound of the present invention by subjecting as a result of metabolism such as oxidation, reduction and hydrolysis in vivo are also included. The present invention further includes the compounds which produce the compound of the present invention as a result of metabolism such as oxidation, reduction and hydrolysis in vivo.

The compounds (I) of the present invention can be prepared by various processes. Representative processes of them are as follows.

1) When Z is a Single Bond

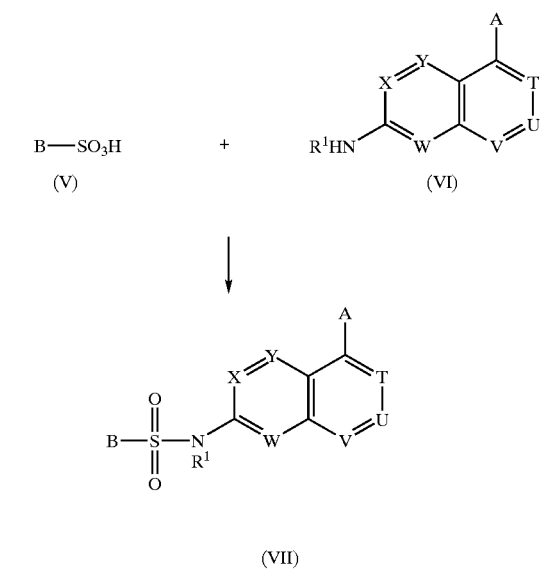

In the formula, A, B, T, U, V, W, X and T have the same meanings as defined above.

Specifically, the objective compounds can be prepared by allowing a sulfonic acid represented by the formula (V) or a reactive derivative thereof to react with a compound represented by the formula (VI).

Such reactive derivatives of the sulfonic acid (V) include, for example, generally used reactive derivatives such as sulfonyl halides, sulfonyl anhydrides and N-sulfonylimidazolide. Among them, sulfonyl halides are typically preferred. Solvents for use in the reaction are not specifically limited, but are preferably solvents that dissolve material substances and are inert to these materials. Such solvents include pyridine, tetrahydrofuran, dioxane, benzene, ethyl ether, dichloromethane, dimethylformamide, and mixtures of these solvents. When an acid liberates accompanied with a proceeding reaction as in the case when a sulfonyl halide is used in the reaction, the reaction is preferably performed in the presence of an appropriate deacidification agent. Therefore, in such a case, pyridine and other basic solvents are typically preferably used. When a neutral solvent is used, an alkali metal carbonate, an organic tertiary amine or another basic substance may be added to the reaction system. Solvents that can be used herein are not limited to those mentioned above. The reaction generally proceeds at room temperature, but the reaction system may be cooled or heated according to necessity. The reaction time can optionally be selected depending on the types of material compounds and the reaction temperature and is generally from 10 minutes to 20 hours.

When the amino group or hydroxyl group of the resulting product is protected, a sulfonamide derivative (VII) having a free hydroxyl group or amino group can be obtained by subjecting the product to treatment with an acid, treatment with a base, catalytic reduction and other conventional deprotecting procedures according to necessity.

2) When Z is —CO—NH—

The reaction between the sulfonamide represented by the formula (IX) and the haloformate represented by the formula (XIII) is performed in an inert solvent such as acetone, tetrahydrofuran and methyl ethyl ketone in the presence of an acid scavenger such as potassium carbonate, sodium carbonate, potassium hydroxide and sodium hydroxide. A reaction temperature may range from about 30° C. to reflux

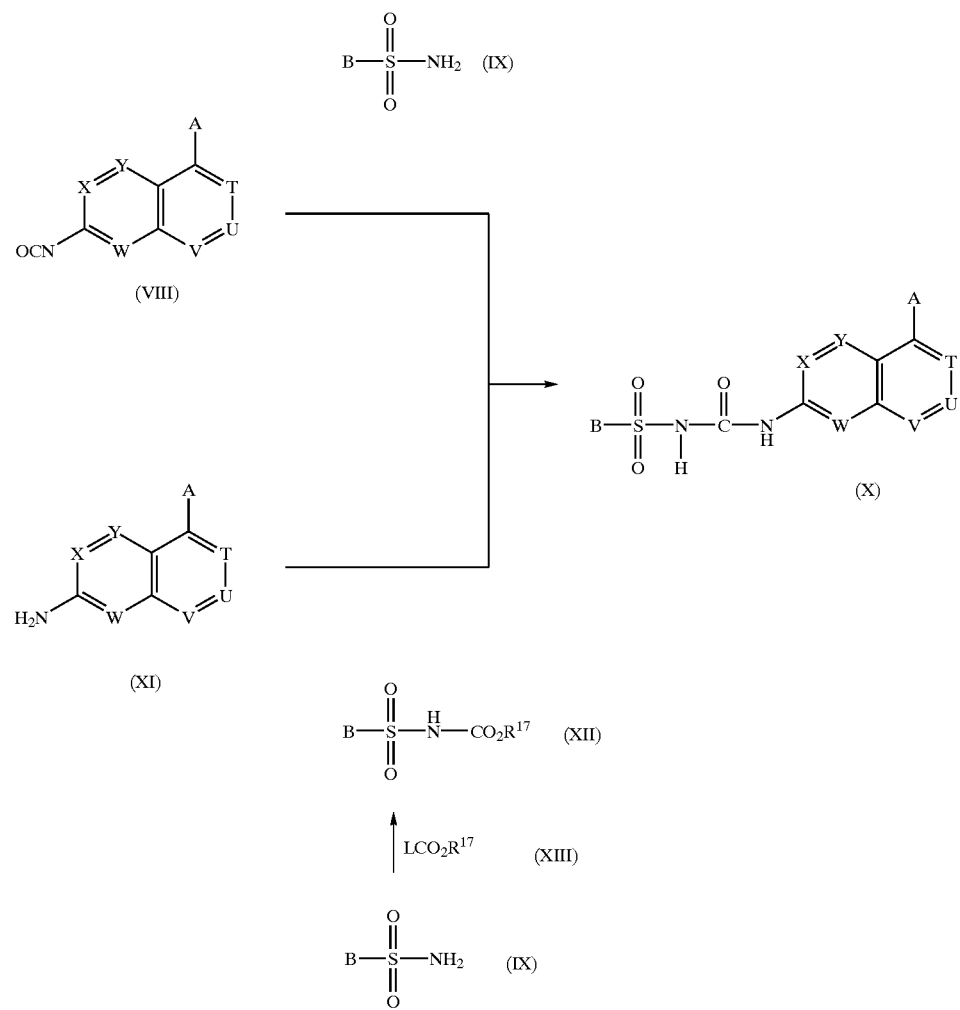

In the formula, L is chlorine atom or bromine atom; $R^{17}$ is a C1–C4 alkyl group or a benzyl group; and A, B, T, U, V, W, X and Y have the same meanings as defined above.

The target compound can be prepared by allowing an isocyanate compound represented by the formula (VIII) to react with sulfonamide compound represented by the formula (IX).

The reaction is generally performed in water or a water-miscible inert solvent such as tetrahydrofuran and acetone in the presence of a base such as sodium hydroxide, potassium hydroxide, lithium hydroxide, sodium methoxide and sodium hydride. The reaction is performed at a temperature from 0° C. to 100° C. and preferably from about 20° C. to about 30° C.

Alternatively, the target compound is prepared by a process in which the sulfonamide represented by the formula (IX) is allowed to react with a haloformate represented by the formula (XIII) to give a carbamate represented by the formula (XII), and the resulting carbamate is allowed to react with an amine represented by the formula (XI).

temperature. Subsequently, the reaction between the carbamate represented by the formula (XII) and the amine represented by the formula (XI) is performed by heating in an inert high-boiling solvent such as dioxane, toluene and diglyme at temperatures ranging from about 50° C. to reflux temperature.

The amine compounds represented by the formula (VI) or (XI) are materials for the sulfonamide- or sulfonylurea-containing heterocyclic compounds of the present invention and can be prepared by combinations of conventional procedures.

For example, quinoline and isoquinoline derivatives can be prepared according to the following production processes.

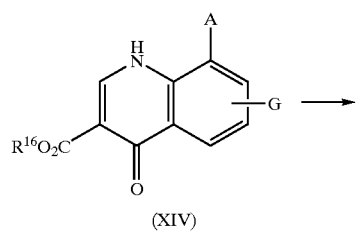
(XIV)
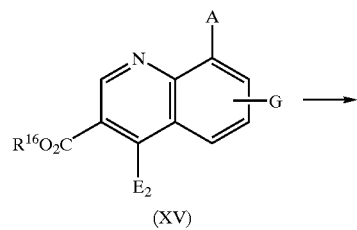
(XV)
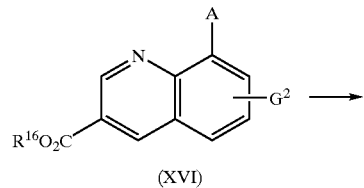
(XVI)
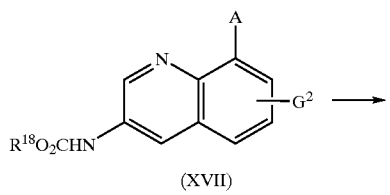
(XVII)
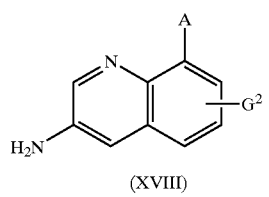
(XVIII)
In the formula, A, $E_2$, $G^2$ and $R^{16}$ have the same meanings as defined above; and $R^{18}$ is a C1–C4 alkyl group or a benzyl group.
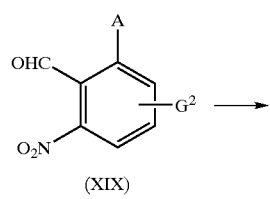
(XIX)
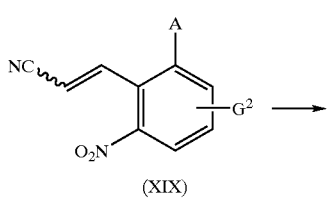
(XIX)
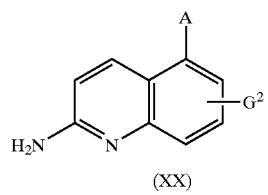
(XX)
In the formula, A and $G^2$ have the same meanings as defined above.
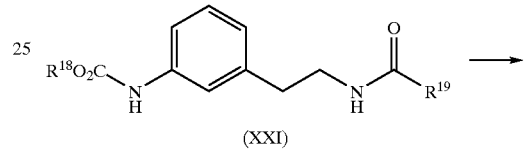
(XXI)
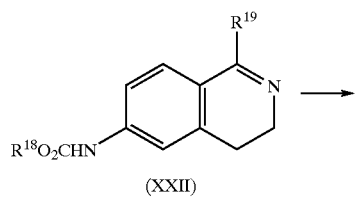
(XXII)
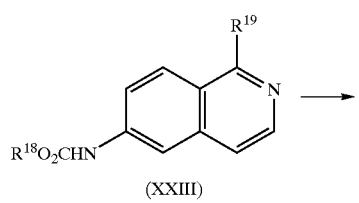
(XXIII)
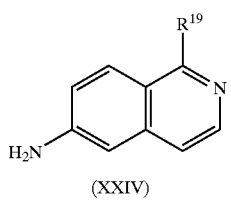
(XXIV)
In the formula, $R^{18}$ has the same meaning as defined above; and $R^{19}$ is a C1–C4 alkyl group.
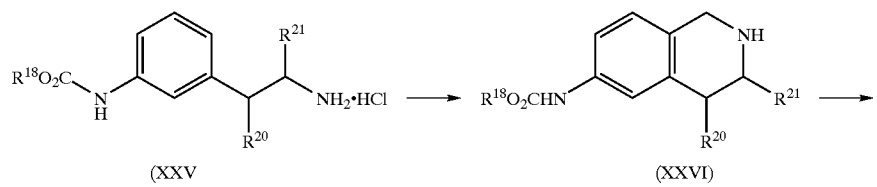
(XXV)   (XXVI)

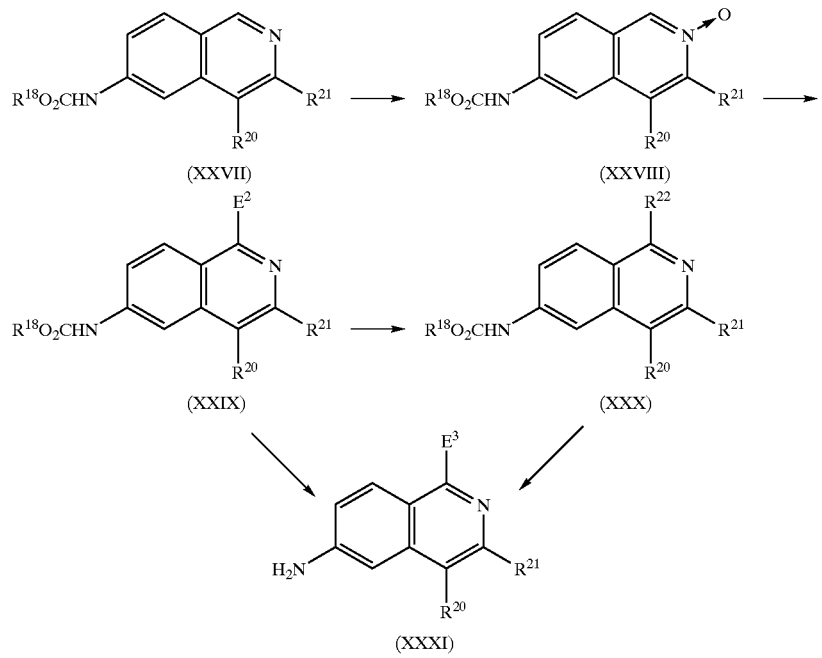

In the formula, $R^{18}$ and $E^2$ have the same meanings as defined above; $R^{20}$ and $R^{21}$ are each hydrogen atom or a C1–C4 alkyl group; $R^{22}$ is a C1–C4 alkoxy group, an optionally substituted phenoxy group or phenyl group, cyano group, or an amino group which may be substituted with one or two C1–C4 alkyl groups; and $E^3$ is hydrogen atom, a halogen atom, a C1–C4 alkoxy group, an optionally substituted phenoxy group or phenyl group, cyano group, or an amino group which may be substituted with one or two C1–C4 alkyl groups.

When the compounds of the present invention are used as pharmaceutical drugs, they are administered to a patient orally or parentally. The dose varies depending on the severity of symptoms, age, sex, body weight and sensitivity of the patient, medication method, administration time period, administration interval, characteristics, dispensing and type of the resulting pharmaceutical preparation, the type of the active ingredient etc., and is not specifically limited. The dose is generally from 10 to 6000 mg, preferably from about 50 to about 4000 mg and more preferably from 100 to 3000 mg per day per adult. The drug is administered to a subject one to three times a day.

To prepare oral solid preparations, fillers and, where necessary, other additives such as binders, disintegrators, lubricants, coloring agents and flavoring agents are added to a base component, and the resulting mixture is formed into tablets, coated tablets, granules, fine granules, powders, capsules etc. according to a conventional procedure.

Such fillers include lactose, corn starch, sucrose, glucose, sorbitol, crystalline cellulose and silicon dioxide. The binders include, for example, polyvinyl alcohol, ethyl cellulose, methylcellulose, gum arabic, hydroxypropylcellulose and hydroxypropylmethylcellulose. The lubricants include magnesium stearate, talc and silica. The coloring agents include those permitted to use in pharmaceutical drugs. The flavoring agents include cocoa powder, menthol, aromatic powder, peppermint oil, borneol and powdered cinnamon bark. These tablets and granules can be coated with sugar, gelatin or other coating substances according to necessity.

To prepare injections, additives such as pH adjusting agents, buffers, suspending agents, solubilizing agents, stabilizers, isotonicity and preservatives are added to the base component, and the resulting mixture is formed into intravenous injections, subcutaneous injections or intramuscular injections according to a conventional procedure. Where necessary, the injections are formed into freeze-dried preparations.

Such suspending agents include methylcellulose, polysorbate 80, hydroxyethylcellulose, gum arabic, powdered tragacanth, sodium carboxymethylcellulose and polyoxyethylene sorbitan monolaurate.

The solubilizing agents include polyoxyethylene hydrogenated caster oil, polysorbate 80, nicotinamide, polyoxyethylene sorbitan monolaurate, Macrogol and caster oil fatty acid ethyl esters.

The stabilizers include sodium sulfite and sodium metasulfite, and the preservatives include, for example, methyl parahydroxybenzoate, ethyl parahydroxybenzoate, sorbic acid, phenol, cresol and chlorocresol.

The effect of the compounds of the present invention will be illustrated with reference to Pharmacological Experimental Example below.

Pharmacological Experimental Example 1, Antiangiogenic Effect

The inhibition degree of angiogenesis which was observed when aorta pieces of rat were incubated in collagen was defined as an antiangiogenic effect. That is, the thoracic aorta excised from male rat of Sprague-Dawley strain (10–12 weeks age) was washed with a Hanks' solution (Gibco BRL, Gaithersburg, USA) so that fat tissues around there were removed minutely. The aorta was incised to prepare pieces of 2 mm square and they were allowed to stand in a 24-well plate holding the endothelial cells upside. Then, 500 μl of neutralized Type I collagen (Cell Matrix Type I-A; manufactured by Nitta Gelatin) were poured over each well and allowed to stand at room temperature for about 20 minutes in a clean bench to solidify the gel. After confirming that the gel was solidified, 500 μl of MCDB 131 medium (manufactured by Chlorella Kogyo) were added thereto followed by incubating in a $CO_2$ incubator (5% $CO_2$) at 37° C. On the next day, the culture medium was exchanged with 500 μl of MCDB 131 medium containing the test compound and the incubation was continued. After three days, the medium was again exchanged with 500 μl of MCDB 131 medium containing the test compound and, at the stage of the 7th day from the initiation of addition of the test compound, numbers of capillaries formed around the aorta were counted under a microscope. The solution containing the test compound was prepared in a three-fold dilution system where 10 μg/ml was the highest concentration.

Inhibiting rate was calculated from the following formula and 50% inhibiting concentration ($IC_{50}$) for each test compound was determined.

Inhibiting Rate (%)=(C−T)/$C_x$100

C: Numbers of capillaries when no compound was added
T: Numbers of capillaries when a compound was added
Table 1

| Test Compound (Ex. No.) | $IC_{50}$ (μg/ml) |
|---|---|
| Ex 1 | 0.49 |
| Ex 2 | 0.74 |
| Ex 4 | 0.09 |
| Ex 6 | 0.12 |
| Ex 11 | 0.04 |
| Ex 15 | 0.87 |
| Ex 24 | 0.49 |
| Ex 27 | 0.08 |
| Ex 38 | 0.15 |
| Ex 47 | 0.09 |
| Ex 48 | 0.35 |
| Ex 50 | 0.31 |
| Ex 53 | 0.53 |
| Ex 59 | 0.20 |
| Ex 61 | 0.3 |
| Ex 69 | 0.15 |
| Ex 77 | 0.39 |
| Ex 80 | 0.20 |
| Ex 81 | 0.85 |
| Ex 84 | 0.14 |
| Ex 91 | 0.33 |
| Ex 92 | 0.2 |

EXAMPLES

Next, Preparation Examples illustrating the preparation of material compounds for the compounds of the present invention and Examples on typical examples of the compounds of the present invention are shown below. Though these Examples are not intended to limit the scope of the present invention.

Preparation Example 1
2-Amino-9-bromoquinoline

After stirring 2-bromo-6-nitrobenzaldehyde (30.4 g), magnesium oxide (75 g) and dimethyl sulfoxide (11.3 ml) sufficiently for 1 minute, diethyl (cyanomethyl)phosphonate (25.8 ml) was added thereto and the mixture was stirred for further 2 hours. After the completion of stirring, the mixture was left stand overnight. Then, ethyl acetate was added thereto, and the mixture was stirred and then filtered. The filtrate was concentrated and the residue was purified by silica gel column chromatography (ethyl acetate), to give 32 g of 3-(2-bromo-6-nitrophenyl)-2-propenenitrile (E-isomer:Z-isomer=3:1).

$^1$H-NMR(CDCl$_3$) δ (ppm): 5.63(d, J=16.5 Hz, E-isomer 1H), 5.81(d, J=10.8 Hz, Z-isomer 1H), 7.42–7.52(m, E-isomer 1H, Z-isomer 2H), 7.56(d, J=16.5 Hz, E-isomer 1H), 7.90–8.16(m, E-isomer 2H, Z-isomer 2H).

Next, ethanol (250 ml), tin (60 g) and distilled water (150 ml) were added to 32 g of 3-(2-bromo-6-nitrophenyl)-2-propenenitrile (E-isomer:Z-isomer=3:1), the resulting mixture was heated to 90° C. under stirring, followed by dropwise addition of concentrated hydrochloric acid (256 ml) and stirring at 90° C. for 3 hours. After cooling to room temperature, the liquid layer was separated by decantation and cooled to 0° C. The resulting solid matter was collected by filtration, was diluted with aqueous ammonia and was extracted with ethyl acetate. The extract was concentrated and the residue was purified by silica gel column chromatography (ethyl acetate), to give 5.0 g of the title compound.

$^1$H-NMR(CDCl$_3$) δ (ppm): 4.88(2H, bs), 6.79(1H, d, J=9.3 Hz), 7.39(1H, t, J=8.9 Hz), 7.51(1H, d, J=8.9 Hz), 7.61(1H, d, J=8.9 Hz), 8.27(1H, d, J=9.3 Hz).

Preparation Example 2
2-Amino-5-chloroquinoline

The title compound was obtained from 2-chloro-6-nitrobenzaldehyde in the same manner as in Preparation Example 1.

$^1$H-NMR(CDCl$_3$) δ (ppm): 5.25(2H, bs), 6.80(1H, d, J=9.7 Hz), 7.32(1H, dd, J=7.5 Hz, 1.5 Hz), 7.46(1H, t, J=7.5 Hz), 7.57(1H, m), 8.30(1H, d, J=9.7 Hz, 1.0 Hz).

Preparation Example 3
3-Carbethoxy-4-hydroxy-8-bromoquinoline

A mixture of 50 g (0.291 mol) of 2-bromoaniline and 63 g (0.291 mol) of diethyl ethoxymethylenemalonate was heated at 100° C. under a reduced pressure for 3 hours, followed by heating at 200° C. for further 12 hours. After the completion of the reaction, the solid matter in the resulting reaction mixture was washed with ethyl acetate, and the crystals were collected by filtration and dried, to give 50 g of the title compound.

$^1$H-NMR(DMSO-d$_6$) δ (ppm): 1.26(3H, t, J=7.2 Hz), 4.21(2H, q, J=7.2 Hz), 7.34(1H, t, J=7.6 Hz), 8.03(1H, dd, J=1.6 Hz, 7.6 Hz), 8.15(1H, dd, J=1.6 Hz, 7.6 Hz), 8.43(1H, s), 11.56(1H, s).

Preparation Example 4
3-Carbethoxy-8-bromoquinoline

A mixture of 2.5 g (8.4 mmol) of 3-carbethoxy-4-hydroxy-8-bromoquinoline and 10 ml of phosphorus oxychloride was heated under reflux for 1 hour. After the completion of the reaction, phosphorus oxychloride was removed and the residue was purified by NH silica gel, to give 2.6 g of a chlorinated derivative. Next, 500 mg (1.6 mmol) of the chlorinated derivative was dissolved in 20 ml of dioxane, and 1 g of powdered zinc and 3 ml of acetic acid were added thereto, followed by heating at 65° C. for 30 minutes. To the reaction mixture was added ethyl acetate, followed by filtering through Celite. The filtrate was washed with brine, dried over magnesium sulfate and concentrated. To the residue was added 1 ml of acetic acid, and the mixture was left stand for 12 hours. Then, acetic acid was removed, and the residue was subjected to silica gel column chromatography and eluted with an eluent (ethyl acetate-n-hexane=1–7), to give 180 mg of the title compound.

$^1$H-NMR(CDCl$_3$) δ (ppm): 1.47(3H, t, J17.2 Hz), 4.50 (2H, q, J=7.2 Hz), 7.50(1H, t, J=7.6 Hz), 7.93(1H, dd, J=1.2 Hz, 7.6 Hz), 8.18(1H, dd, J=1.2 Hz, 7.6 Hz), 8.85(1H, d, J=2 Hz), 9.57(1H, d, J=2 Hz).

Preparation Example 5
3-Amino-8-bromoquinoline

To a mixture of ethanol (10 ml) and 1 N NaOH aqueous solution (10 ml) was added 500 mg (1.8 mmol) of 3-carbethoxy-8-bromoquinoline, followed by stirring at room temperature for 3 hours. Ethanol was removed, and the residue was neutralized with 1 N HCl. The resulting solid was collected by filtration, washed with water and dried, to give 450 mg of a carboxylic acid. Then, 450 mg (1.8 mmol) of the carboxylic acid was added to 25 ml of tert-butanol, and 0.58 ml (2.7 mmol) of DPPA and 0.37 ml (2.7 mmol) of triethylamine were further added thereto, followed by heating under reflux for 12 hours. The reaction mixture was concentrated, and the residue was subjected to silica gel chromatography and eluted with an eluent (ethyl acetate-n-hexane=1–4), to give 352 mg of an amide derivative. Then, 350 mg (1.1 mmol) of the amide derivative was added to a mixture of 4 ml of methanol and 2 ml of concentrated HCl, followed by stirring at room temperature for 1 hour. The reaction mixture was basified with aqueous ammonia and extracted with ethyl acetate. The organic layer was washed with brine, dried over magnesium sulfate and then concentrated, to give 240 mg of the title compound.

$^1$H-NMR(DMSO-d$_6$) δ (ppm): 5.88(2H, s), 7.13(1H, d, J=2.8 Hz), 7.24(1H, dd J=7.6 Hz, 8.4 Hz), 7.59–7.65(2H, m), 8.49(1H, d, J=2.8 Hz).

Preparation Example 6
3-Amino-8-iodoquinoline

The title compound was obtained from 2-iodoaniline in the same manner as in Preparation Examples 3 to 5.

$^1$H-NMR(DMSO-d$_6$) δ (ppm): 5.85(2H, s), 7.07(1H, d, J=2.8 Hz), 7.10(1H, t, J=7.6 Hz), 7.62(1H, dd, J=1.2 Hz, 7.6 Hz), 7.90(1H, dd, J=1.2 Hz, 7.6 Hz), 8.45(1H, dd, J=2.8 Hz).

Preparation Example 7
3-Amino-8-cyanoquinoline

The title compound was obtained from 2-cyanoaniline in the same manner as in Preparation Examples 3 to 5.

$^1$H-NMR(DMSO-d$_6$) δ (ppm): 6.03(2H, br s), 7.22(1H, d, J=2.8 Hz), 7.48(1H, dd, J=7.2 Hz, 8.4 Hz), 7.84(1H, dd, J=1.2 Hz, 8.4 Hz), 7.94(1H, dd, J=1.2 Hz, 8.4 Hz), 8.57(1H, d, J=2.8 Hz).

Preparation Example 8
3-Amino-8-(methylsulfonyl) quinoline

The title compound was obtained in the same manner as in Preparation Examples 3 to 5.

$^1$H-NMR(CDCl$_3$) δ (ppm): 6.00(2H, s), 7.26(1H, d, J=2.4 Hz), 7.53(1H, t, J=7.2 Hz), 7.91(1H, dd, J=1.6 Hz, 7.2 Hz), 7.96(1H, dd, J=1.2 Hz, 8.4 Hz), 8.58(1H, d, J=2.8 Hz).

Preparation Example 9
3-Amino-8-chloroquinoline

The title compound was obtained in the same manner as in Preparation Examples 3 to 5.

$^1$H-NMR(DMSO-d$_6$) δ (ppm): 5.90(2H, s), 7.17(1H, d, J=2.8 Hz), 7.33(1H, t, J=7.6 Hz), 7.46(1H, d, J=7.6 Hz), 7.58(1H, d, J=7.6 Hz), 8.52(1H, d, J=2.8 Hz).

Preparation Example 10
3-Amino-8-trifluoromethylquinoline

The title compound was obtained in the same manner as in Preparation Examples 3 to 5.

$^1$H-NMR(DMSO-d$_6$) δ (ppm): 5.94(2H, s), 7.23(1H, d, J=2.8 Hz), 7.48(1H, t, J=7.6 Hz), 7.69(1H, d, J=7.6 Hz), 7.91(1H, d, J=7.6 Hz), 8.55(1H, d, J=2.8 Hz).

Preparation Example 11
Ethyl 8-Chloro-4-vinylquinoline-3-carboxylate

To a solution of 2.0 g (7.4 mmol) of ethyl 4,8-dichloroquinoline-3-carboxylate obtained in the same manner as in Preparation Example 4 in toluene (20 ml) were added tributylvinyltin (2.8 ml) and tetrakis(triphenylphosphine)palladium (171 mg), followed by stirring for 2 hours while heating under reflux. The reaction mixture was filtrated through Celite and concentrated. Then, the residue was purified by silica gel chromatography, to give 1.92 g of the title compound.

$^1$H-NMR(DMSO-d$_6$) δ (ppm): 1.36(3H, t, J=7.6 Hz), 4.37(2H, d, J=7.6 Hz), 5.52(1H, d, J=18.0 Hz), 5.58(1H, d, J=16.4 Hz), 7.40(1H, dd, J=16.4, 18.0 Hz), 7.70(1H, t, J=8.0 Hz), 8.11(1H, d, J=8.0 Hz), 8.25(1H, d, J=8.0 Hz), 9.24(1H, s).

Preparation Example 12
3-Amino-8-chloro-4-vinylquinoline

The title compound was obtained from ethyl 4-vinyl-8-chloroquinoline-3-carboxylate in the same manner as in Preparation Example 5.

$^1$H-NMR(DMSO-d$_6$) δ (ppm): 5.69(1H, dd, J=1.6, 18.0 Hz), 5.81(2H, s), 5.84(1H, dd, J=1.6, 11.6 Hz), 6.91(1H, dd, J=11.6, 18.0 Hz), 7.38(1H, t, J=8.0 Hz), 7.52(1H, dd, J=1.2, 8.0 Hz), 7.85(1H, dd, J=1.2, 8.0 Hz), 8.60(1H, s).

Preparation Example 13
Ethyl 7-Amino-2-chloroquinoline-4-carboxylate

To 25 g (231 mmol) of m-phenylenediamine was added 43 g (231 mmol) of diethyl oxaloacetate, followed by stirring at 160 degrees for 1 hour. After standing to cool, the crystals were washed with methanol. To a solution of the crystals (3.0 g, 13 mmol) in chloroform (30 ml) was added phosphorus oxychloride (3.6 ml), followed by heating under reflux for 1 hour. After standing to cool, the reaction mixture was poured onto ice water, basified with 1 N sodium hydroxide aqueous solution, and the resulting crystals were collected by filtration. The crystals were washed with tetrahydrofuran and the filtrate was evaporated, to give 4.85 g of the title compound.

$^1$H-NMR(DMSO-d$_6$) δ (ppm): 1.31–1.42(3H, m), 4.34–4.46(2H, m), 6.92(1H, d, J=2.4 Hz), 7.12(1H, dd, J=2.4, 9.2 Hz), 7.40(1H, s), 8.21(1H, d, J=9.2 Hz).

Preparation Example 14
2-Benzylthio-4-methoxypyridazine

In dimethyl sulfoxide (30 ml) was suspended 843 mg (21 mmol, 55% in oil) of sodium hydroxide, and 2.0 ml (16.7 mol) of benzylmercaptan was added thereto under ice-cooling, followed by stirring for 10 minutes. To the reaction mixture was added 2.5 g (17.6 mmol) of 4-methoxy-2-chloropyridazine, followed by stirring at room temperature overnight. To the reaction mixture was added an aqueous saturated ammonium chloride, followed by extracting with ethyl acetate. The organic layer was washed with brine, dried over magnesium sulfate and concentrated. Then, the residue was purified by silica gel chromatography, to give 1.63 g of the title compound.

$^1$H-NMR(DMSO-d$_6$) δ (ppm): 3.98(3H, s), 4.48(2H, s), 7.12(1H, d, J=8.8 Hz) 7.22–7.26(1H, m), 7.29–7.37(2H, m), 7.41–7.44(2H, m), 7.57(1H, d, J=8.8 Hz).

Preparation Example 15
2-Benzylthio-4-carboxamidepyridine

To 25 g (159 mmol) of 2-chloroisonicotinic acid was added thionyl chloride (120 ml), followed by stirring for 3 hours while heating under reflux. After standing to cool, the reaction mixture was evaporated, to give the residue. A solution of the residue in tetrahydrofuran (200 ml) was poured into a mixed solution of a saturated ammonium aqueous solution (200 ml) and tetrahydrofuran solution (200 ml) under ice-cooling. After stirring for 15 minutes while ice-cooling, the mixture was evaporated, and the resulting crystals were collected by filtration and washed with water, to give 22.6 g of white crystals. To a solution of 5.13 g (32 mmol) of the above-prepared white crystals in dimethylformamide (70 ml) containing were added 4.2 ml (36 mmol) of benzylthiomercaptan and 10 g (77 mmol) of potassium carbonate were added, followed by stirring for 3 hours while heating under reflux. To the reaction mixture was added water, followed by extracting with ethyl acetate. The organic layer was washed with brine, dried over magnesium sulfate and evaporated. Then, the residue was purified by silica gel chromatography. The resulting crystals were washed with hexane, to give 6.3 g of the title compound.

$^1$H-NMR(DMSO-$d_6$) δ (ppm): 4.46(2H, s), 7.22–7.33 (3H, m), 7.41(2H, d, J=7.2 Hz), 7.49(1H, dd, J=1.6, 5.2 Hz), 7.67(1H, s), 7.73(1H, s), 8.21(1H, s), 8.58(1H, d, J=5.2 Hz).

Preparation Example 16
7-Amino-2-chloro-4-methylquinoline

To 27 g (251 mmol) of m-phenylenediamine was added 32 ml (251 mmol) of ethyl acetoacetate, followed by stirring at 200 degrees for 1 hour. After standing to cool, the crystals were washed with hexane. To 9.5 g (54 mmol) of the crystals was added 15 ml of phosphorus oxychloride, followed by heating under reflux for 2 hours. After standing to cool, the reaction mixture was poured onto ice-water and basified with a saturated ammonium aqueous solution. The resulting crystals were collected by filtration and washed with water. The crystals were washed with methanol and the filtrate was evaporated, to give 4.85 g of the title compound.

$^1$H-NMR(DMSO-$d_6$) δ (ppm): 3.18(3H, s), 5.95(2H, s), 6.82(1H, d, J=2.4 Hz) 6.98(1H, s), 7.01(1H, dd, J=2.4, 8.8 Hz), 7.76(1H, d, J=8.8 Hz).

Preparation Example 17
3,4-Dihydroisoquinoline

To a solution of 26.67 g (0.2 mol) of 1,2,3,4-tetrahydroisoquinoline in methylene chloride (300 ml) was added N-bromosuccinimide (39.2 g) under ice-cooling over 20 minutes. After stirring for 40 minutes, 30% sodium hydroxide aqueous solution (130 ml) was added to the reaction mixture. The organic layer was washed with water, extracted with 10% hydrochloric acid (200 ml), and the aqueous layer was washed with methylene chloride. The aqueous layer was basified with an aqueous ammonia, extracted with methylene chloride. The extract was dried over magnesium sulfate and then evaporated. The resulting residue was distilled (about 16 mm-Hg, 120 degrees), to give 21.5 g of the title compound as an oil.

$^1$H-NMR(DMSO-$d_6$) δ (ppm): 2.66(2H, t, J=8 Hz), 3.62 (2H, td, J=2 Hz, 8 Hz), 7.19–7.21(1H, m), 7.29–7.33(1H, m), 7.35–7.40(1H, m), 8.31 (1H, t, J=2 Hz).

Preparation Example 18
7-Nitroisoquinoline

To concentrated sulfuric acid (70 ml) was added 15 g of potassium nitrate, followed by adding a solution of 18 g (0.14 mol) of 3,4-dihydroisoquinoline in concentrated sulfuric acid (70 ml) at −15 degrees over 20 minutes. After stirring at room temperature for 1 hour, the mixture was heated at 60 degrees for 40 minutes. The reaction mixture was poured onto ice water, and the mixture was basified with aqueous ammonia and extracted with ethyl acetate. The organic layer was washed with brine, dried over magnesium sulfate and concentrated. To the residue were added decalin (100 ml), nitrobenzene (100 ml) and Pd-Black (2 g), followed by heating at 200 degrees in a stream of nitrogen overnight. The reaction mixture was washed with ethyl acetate and extracted with 2 N hydrochloric acid. The aqueous layer was washed with ethyl acetate, followed by adding an aqueous sodium hydroxide. The resulting precipitates were collected by filtration and washed with water, to give 14.4 g of the title compound.

$^1$H-NMR(CDCl$_3$) δ (ppm): 7.79(1H, d, J=5.6 Hz), 8.00 (1H, d, J=9.2 Hz), 8.48(1H, dd, J=2.4 Hz, 9.2 Hz), 8.75(1H, d, J=5.6 Hz), 8.96(1H, d, J=2 Hz), 9.48(1H, s).

Preparation Example 19
4-Bromo-7-nitroisoquinoline

To 1.6 g (9.19 mmol) of 7-nitroquinoline were added 1.2 ml of an aqueous hydrobromic acid and 3 ml of bromine, followed by heating at 180 degrees for 5.5 hours. The reaction mixture was extracted with ethyl acetate, and the extract was successively washed with sodium hydroxide aqueous solution, sodium thiosulfate aqueous solution and brine, dried over magnesium sulfate and concentrated. Then, the resulting residue was purified by silica gel column chromatography (eluted with hexane-hexane:ethyl acetate= 4:1), to give 500 mg of the title compound.

$^1$H-NMR(CDCl$_3$) δ (ppm): 8.36(1H, d, J=9.2 Hz), 8.58 (1H, d, J=2.4 Hz, 9.2 Hz), 8.93(1H, s), 8.96(1H, d, J=3.2 Hz), 9.38(1H, s).

Preparation Example 20
7-Amino-4-bromoisoquinoline

In 1 ml of ethanol, 2 ml of tetrahydrofuran and 1 ml of water was dissolved 66 mg (0.26 mmol) of 7-nitro-4-bromoisoquinoline, and 70 mg of powdered iron and 140 mg of ammonium chloride were added thereto, followed by heating at 50 degrees for 3 hours. To the reaction mixture was added 1 N sodium chloride aqueous solution, followed by extracting with chloroform. The organic layer was dried over magnesium sulfate and concentrated. Then, the resulting residue was crystallized from isopropyl ether, to give 33 mg of the title compound.

$^1$H-NMR(DMSO-$d_6$) δ (ppm): 5.98(2H, s), 6.97(1H, d, J=2.4 Hz), 7.31(1H, dd, J=2.4 Hz, 8.8 Hz), 8.28(1H, s), 8.89(1H, s).

Preparation Example 21
6-(4-Toluenesulfonylamino)isoquinoline

In pyridine (30 ml) was dissolved 6-aminoisoquinoline (3.348 g, Synthesis, 733 (1975), and 4-toluenesulfonyl chloride (5.13 g) was added thereto, followed by stirring at room temperature overnight. Water was added thereto, followed by extracting with ethyl acetate. The extract was washed with brine, dried over anhydrous magnesium sulfate and the solvent was evaporated. The residue was recrystallized from ethanol, to give the title compound (5.958 g, 85%) as pale yellow crystals.

$^1$H-NMR(DMSO-$d_6$) δ (ppm): 2.28(3H, s), 7.32(2H, d, J=8.2 Hz), 7.40(1H, dd, J=1.6, 9.2 Hz), 7.55(1H, brs), 7.67(1H, d, J=5.6 Hz), 7.74(2H, d, J=8.2 Hz), 7.97(1H, d, J=9.2 Hz), 8.36(1H, d, J=5.6 Hz), 9.10(1H, s).

Preparation Example 22
1-Chloro-6-(4-toluensulfonylamino)isoquinoline

In chloroform (100 ml) was dissolved 3.0 g of 6-(4-toluenesulfonylamino)isoquinoline (Preparation Example 21), and m-chloroperbenzoic acid (2.57 g) was added thereto under ice-cooling, followed by stirring at room temperature overnight. The solvent was evaporated, and the resulting crystals were washed with diethyl ether, collected by filtration and dried, to give pale yellow crystals. The obtained crystals were suspended in chloroform (83 ml), and phosphorus oxychloride (19 ml) was added thereto, followed by heating under reflux for 5 hours. After cooling, the solvent was evaporated, and the residue was basified with an aquesou sodium bicarbonate in an ice-bath, followed by extracting with ethyl acetate, The extract was washed with brine, dried over anhydrous magnesium sulfate and the solvent was evaporated. The residue was purified by silica gel column, to give crude crystals of the title compound (1.630 g, 49.40%). The crude crysatals were recrystallized from ethanol, to give the title compound as colorless crystals.

$^1$H-NMR(DMSO-$d_6$) δ (ppm): 2.29(3H, s), 7.34(2H, d, J=8.0 Hz), 7.52(1H, dd, J=2.0, 9.0 Hz), 7.65(1H, d, J=2.0 Hz), 7.76(1H, d, J=5.6 Hz), 7.77(2H, d, J=8.0 Hz), 8.14(1H, d, J=9.0 Hz), 8.16(1H, d, J=5.6 Hz).

Preparation Example 23
6-Amino -1-chloroisoquinoline

In sulfuric acid (30 ml) was dissolved 3.323 g of 1-chloro-6-(4-toluenesulfonylamino)isoquinoline (Preparation Example 22), followed by stirring at room temperature overnight. The reaction mixture was poured onto ice, and basified by adding an aqueous sodium hydroxide and then potassium carbonate, followed by extracting with ethyl acetate. The extract was washed with brine, dried over anhydrous magnesium sulfate and the solvent was evaporated, to give the title compound (1.37 g, 76.81%) as yellowish brown crystals.

$^1$H-NMR(DMSO-$d_6$) δ (ppm): 6.23(2H, brs), 6.76(1H, s), 7.09(1H, d, J=9.6 Hz), 7.37(1H, d, J=6.4 Hz), 7.89(1H, d, J=9.6 Hz), 7.90(1H, d, J=6.4 Hz).

Preparation Example 24
2-Chloro-1,6-naphthylidine

In phosphorus oxychloride (19 ml) was dissolved 1.0 g of 1,6-naphthyridin-2-one (J. Org. Chem. 4744 (1990), followed by heating under reflux at 120° C. for 2 hours. After cooling, the solvent was evaporated, the residue was basified with water and potassium carbonate, and then the mixture was extracted with ethyl acetate. The extract was washed with brine, dried over anhydrous magnesium sulfate and the solvent was evaporated, to give the title compound (0.658 g, 58.45%) as orange crystals.

$^1$H-NMR(CDCl$_3$) δ (ppm): 7.55(1H, d, J=8.8 Hz), 7.86 (1H, d, J=6.0 Hz), 8.28(1H, d, J=8.8 Hz), 8.80(1H, d, J=6.0 Hz), 9.29(1H, s).

Preparation Example 25
2-Amino-1,6-naphthylidine

In a sealed tube, 2-chloro-1,6-naphthylidine (0.628 g, Preparation Example 22) and aqueous ammonia (40 ml) were heated at 130° C. for 11 hours. After cooling, the reaction mixture was extracted with ethyl acetate, and the extract was washed with brine, dried over anhydrous magnesium sulfate and the solvent was evaporated. The residue was purified by silica gel column, to give the title compound (0.497 g, 89.73%) as pale yellow crystals.

$^1$H-NMR(DMSO-$d_6$) δ (ppm): 6.81(1H, d, J=8.8 Hz), 7.24(1H, d, J=5.8 Hz), 7.97(1H, d, J=8.8 Hz), 8.34(1H, d, J=5.8 Hz), 8.80(1H, s).

Preparation Example 26
N-(3-nitrophenethyl)phthalimide

In tetrahydrofuran (225 ml) was dissolved 15 g of 3-nitrophenethyl alcohol, followed by adding triphenylphosphine (26 g) and phthalimide (13.9 g). Then, the resulting mixture was ice-cooled, followed by dropwise addition of diethyl azodicarboxylate (15.5 ml). After stirring at room temperature for 1 hour, the resulting crystals were collected by filtration, washed with diethyl ether and dried, to give N-(3-nitrophenethyl)phthalimide as colorless crystals.

$^1$H-NMR(CDCl$_3$) δ (ppm): 3.12(2H, t, J=7.4 Hz), 3.98 (2H, t, J=7.4 Hz), 7.47(1H, dd, J=8.0, 8.0 Hz), 7.60(1H, d, J=8.0 Hz), 7.72(2H, m), 7.83(2H, m), 8.09(1H, d, J=8.0 Hz), 8.12(1H, s).

Preparation Example 27
3-Nitrophenethylamine

In ethanol (150 ml) was suspended N-(3-nitrophenethyl)phthalimide obtained in Preparation Example 26. To the mixture was added hydrazine (5.7 ml), followed by heating under reflux for 1 hour. Though the reaction mixture was once completely dissolved, crystals again precipitated. The crystals were filtered off and washed with cooled ethanol. Then, the solvent was evaporated, to give the title compound (5.559 g, 99%) as a yellow oil.

$^1$H-NMR(CDCl$_3$) δ (ppm): 2.87(2H, t, J=6.8 Hz), 3.04 (2H, t, J=6.8 Hz), 7.48(1H, dd, J=7.6, 8.4 Hz), 7.55(1H, ddd, J=1.2, 1.6, 7.6 Hz), 8.08(2H, m).

Preparation Example 28
N-Acetyl-N-(3-nitrophenethyl)amine

In pyridine (33 ml) was dissolved 5.559 g of 3-nitrophenethylamine (Preparation Example 25), followed by dropwise addition of acetyl chloride (2.5 ml) under ice-cooling. After stirring at room temperature for 0.5 hour, the mixture was again ice-cooled. Water was added thereto, followed by extracting with ethyl acetate, The extract was washed with brine, dried over anhydrous magnesium sulfate and the solvent was evaporated, to give the title compound (6.323 g, 91%) as a yellow oil.

$^1$H-NMR(CDCl$_3$) δ (ppm): 1.97(3H, s), 2.95(2H, t, J=7.0 Hz), 3.55(2H, dt, J=6.0, 7.0 Hz), 5.60(1H, brs), 7.49(1H, dd, J=7.2, 8.0 Hz), 7.55(1H, d, J=7.2 Hz), 8.07(1H, s), 8.12(1H, d, J=8.0 Hz).

Preparation Example 29
N-Acetyl-N-(3-aminophenethyl)amine

In ethanol (40 ml) was dissolved 2.1 g of N-acetyl-N-(3-nitrophenethyl)amine (Preparation Example 28), and powdered iron (2.25 g), ammonium acetate (4.3 g) and water (20 ml) were added thereto, followed by heating under reflux for 1.5 hours. The solid matter was filtered off and washed with ethanol, and a part of the filtrate was evaporated. The residue was extracted with ethyl acetate, washed with brine, dried over anhydrous magnesium sulfate and the solvent was evaporated, to give the title compound (1.723 g, 96%) as a yellow oil.

$^1$H-NMR(CDCl$_3$) δ (ppm): 1.94(3H, s), 2.72(2H, t, J=6.8 Hz), 3.50(2H, dt, J=6.0, 6.8 Hz), 6.53(1H, s), 6.57(1H, d, J=8.0 Hz), 6.59(1H, d, J=7.2 Hz), 7.10(1H, dd, J=7.2, 8.0 Hz).

Preparation Example 30
N-Acetyl-N-(3-ethoxycarbonylaminophenethyl)amine

In pyridine (5 ml) was dissolved 1.7 g of N-acetyl-N-(3-aminophenethyl)amine (Preparation Example 29), followed by dropwise addition of ethyl chloroformate (1.4 ml) under ice-cooling. After stirring at room temperature for 1 hour, the mixture was ice-cooled again. Water was added thereto, followed by extracting with ethyl acetate. The extract was washed with brine, dried over anhydrous magnesium sulfate and the solvent was evaporated, to give the title compound (2.358 g, 97%) as a yellow oil.

¹H-NMR(CDCl₃) δ (ppm): 1.29(3H, t, J=7.2 Hz), 1.93 (3H, s), 2.76(2H, t, J=7.0 Hz), 3.47(2H, dt, J16.0, 7.0 Hz), 4.20(2H, q, J=7.2 Hz), 5.57(1H, brs), 6.86(1H, d, J=7.2 Hz), 7.21(1H, dd, J=7.2, 8.0 Hz), 7.28(1H, d, J=8.0 Hz), 7.29(1H, s).

Preparation Example 31

6-Ethoxycarbonylamino-1-methyl-3,4-dihydroisoquinoline

Using 1.0 g of N-acetyl-N-(3-ethoxycarbonylaminophenethyl)amine (Preparation Example 30), cyclization reaction was conducted according to the procedure described in Heterocycles 31(2), 341 (1990). After the completion of the reaction, the reaction mixture was poured onto ice, the mixture was basified with potassium carbonate, and extracted with ethyl acetate. The extract was washed with brine, dried over anhydrous magnesium sulfate and the solvent was evaporated, to give the title compound as brown oil.

¹H-NMR(CDCl₃) δ (ppm): 1.19(3H, t, J=7.2 Hz), 2.23 (3H, s), 2.60(2H, t, J=7.4 Hz), 3.55(2H, t, J=7.4 Hz), 4.13(2H, q, J=7.2 Hz), 7.31(1H, d, J=6.8 Hz), 7.32(1H, s), 7.34(1H, d, J=6.8 Hz).

Preparation Example 32

6-Ethoxycarbonylamino-1-methylisoquinoline

To 6-ethoxycarbonylamino-1-methyl-3,4-dihydroisoquinoline were added p-cymene (100 ml) and palladium-carbon (0.9 g), followed by heating under stirring at 195° C. in nitrogen atmosphere for 1 hour. After filtering off the catalyst, the reaction mixture was washed with ethanol and a part of the filtrate was evaporated. The residue was extracted with 1N hydrochloric acid, and then basified with potassium carbonate, followed by extracting with ethyl acetate. The extract was washed with brine, dried over anhydrous magnesium sulfate and the solvent was evaporated, to give the title compound (0.629 g, 69%, 2 steps) as pale yellow crystals.

¹H-NMR(CDCl₃) δ (ppm): 1.30(3H, t, J=7.2 Hz), 2.89 (3H, s), 4.26(2H, q, J=7.2 Hz), 7.40(1H, d, J=5.8 Hz), 7.56(1H, dd, J=1.6, 8.8 Hz), 7.99(1H, d, J=8.8 Hz), 8.05(1H, d, J=1.6 Hz), 8.30(1H, d, J=5.6 Hz), 8.37(1H, s).

Preparation Example 33

6-Amino-1-methylisoquinoline

In ethanol (20 ml) was dissolved 0.629 g of 6-ethoxycarbonylamino-1-methylisoquinoline (Preparation Example 32), and 8 N sodium hydroxide aqueous solution (6.8 ml), followed by heating under reflux for 1.5 hours. After cooling as it was to room temperature, an aqueous saturated ammonium chloride was added thereto, followed by extracting with ethyl acetate. The extract was washed with brine, dried over anhydrous magnesium sulfate and the solvent was evaporated, to give the title compound (0.311 g, 72%) as pale yellow crystals.

¹H-NMR(CDCl₃) δ (ppm): 2.81(3H, s), 4.24(2H, brs), 6.60(1H, d, J=2.0 Hz), 6.91(1H, ddd, J=1.6, 2.0, 8.8 Hz), 7.18(1H, d, J=5.6 Hz), 7.84(1H, d, J=8.8 Hz), 8.16(1H, dd, J=1.6, 5.6 Hz).

Preparation Example 34

N-t-Butoxycarbonyl-3-nitrophenethylamine

In tetrahydrofuran (130 ml) was dissolved 4.559 g of 3-nitrophenethylamine (Preparation Example 27), and triethylamine (8.4 ml) and di-t-butyl dicarbonate (6.6 g) were added thereto, followed by stirring at room temperature for 2 hours. The solvent was evaporated, and to the residue was added brine, followed by extracting with ethyl acetate. The extract was washed with brine, dried over anhydrous magnesium sulfate and the solvent was evaporated, to give the title compound (8.789 g, including impurities) as a yellow oil. The product was subjected to the subsequent reaction as intact without further purification.

¹H-NMR(CDCl₃) δ (ppm): 1.53(9H, s), 2.92(2H, t, J=7.6 Hz), 3.42(2H, dt, J=6.4, 6.8 Hz), 4.58(1H, brs), 7.48(1H, dd, J=7.2, 8.0 Hz), 7.54(1H, d, J=8.0 Hz), 8.07(1H, s), 8.10(1H, d, J=7.2 Hz).

Preparation Example 35

3-(2-t-Butoxycarbonlylaminoethyl)-aniline

Using N-t-butoxycarbonyl-3-nitrophenethylamine (8.789 g, including impurities, Preparation Example 34), the title compound (5.521 g, 76%) was obtained as a yellow oil in the same manner as in Preparation Example 29.

¹H-NMR(CDCl₃) δ (ppm): 1.44(9H, s), 2.70(2H, t, J=7.4 Hz), 3.36(2H, brq), 4.54(1H, brs), 6.54(1H, s), 6.57(1H, d, J=8.0 Hz), 6.60(1H, d, J=7.2 Hz), 8.10(1H, dd, J=7.2, 8.0 Hz).

Preparation Example 36

3-(2-t-Butoxycarbonylaminoethyl)-ethoxycarbonylaminobenzene

Using 3-(2-t-butoxycarbonylaminoethyl)-aniline (5.521 g, Preparation Example 35), the title compound (0.320 g) was obtained as a yellow oil in the same manner as in Preparation Example 29. The product was subjected to the subsequent reaction as intact without further purification.

¹H-NMR(CDCl₃) δ (ppm): 1.31(3H, t, J=7.2 Hz), 1.43 (9H, s), 2.77(2H, t, J=7.4 Hz), 3.67(2H, brq), 4.22(2H, q, J=7.4 Hz), 4.55(1H, brs), 6.52(1H, brs), 6.89(1H, m), 7.24 (1H, m).

Preparation Example 37

3-Ethoxycarbonylaminophenethylamine hydrochloride

In ethanol (15 ml) was dissolved 14.96 g of 3-(2-t-butoxycarbonylaminoethyl)-ethoxycarbonylaminobenzene (Preparation Example 36). Under ice-cooling, hydrochloric acid (15 ml) was added thereto, followed by stirring at room temperature for 20 minutes. Hydrochloric acid (12 ml) and ethanol (15 ml) were further added thereto, followed by stirring at room temperature for 20 minutes. Then, hydrochloric acid (20 ml) and ethanol (30 ml) were further added thereto, followed by stirring at room temperature for 30 minutes. The solvent was evaporated (azeotropic distillation with toluene), to give the title compound (11.99 g) as pale yellow crystals.

¹H-NMR(DMSO-d₆) δ (ppm): 1.22(3H, t, J=7.2 Hz), 2.82(2H, m), 2.95(2H, m), 4.10(2H, q, J=7.2 Hz), 6.86(1H, d, J=7.6 Hz), 7.20(1H, dd, J=7.6, 8.4 Hz), 7.31(1H, d, J=8.4 Hz), 7.36(1H, s), 8.05(2H, brs), 9.61(1H, s).

Preparation Example 38

6-Aminoethyl-1,2,3,4-tetrahydroisoquinoline

The title compound (4.226 g, including impurities) was obtained as a yellow oil according to the procedure described in Chem. Pharm. Bull. 42(8), 1676 (1994), except using 3-ethoxycarbonylaminophenethylamine hydrochloride (4.7 g) obtained in Preparation Example 37.

¹H-NMR(CDCl₃) δ (ppm): 1.29(3H, t, J=7.2 Hz), 2.68 (1H, brs), 2.83(3H, m), 3.73(2H, m), 4.20(2H, q, J=7.2 Hz), 6.77(1H, s), 6.94(1H, d, J=8.4 Hz), 7.07(1H, d, J=8.4 Hz), 7.18(1H, brs).

Preparation Example 39
6-Ethoxycarbonylaminoisoquinoline

To 10 g of 6-aminoethyl-1,2,3,4-tetrahydroisoquinoline (Preparation Example 38) were added p-cymene (100 ml) and palladium-carbon (0.9 g), followed by heating under stirring at 195° C. in nitrogen atmosphere for 1 hour. The catalyst was filtered off and washed ethanol, followed by evaporating the filtrate. The resulting crystals were washed with diethyl ether and dried. The solvent was evaporated, to give the title compound (6.51 g, 66%) as pale yellow crystals.

$^1$H-NMR(CDCl$_3$) δ (ppm): 1.36(3H, t, J=7.2 Hz), 3.74 (1H, m), 4.29(2H, q, J=7.2 Hz), 6.70(1H, d, J=2.0 Hz), 7.46(1H, dd, J=2.0, 8.8 Hz), 7.58(1H, d, J=6.0 Hz), 7.90(1H, d, J=8.8 Hz), 8.04(1H, brs), 8.46(1H, d, J=6.0 Hz), 9.13(1H, s).

Preparation Example 40
6-Ethoxycarbonylaminoisoquinoline-N-oxide

The title compound (293 mg) was obtained as pale yellow crystals in the same manner as in Preparation Example 22, except using 6-ethoxycarbonylaminoisoquinoline (250 mg, Preparation Example 39).

$^1$H-NMR(DMSO-d$_6$) δ (ppm): 1.25(3H, t, J=7.2 Hz), 4.26(2H, q, J=7.2 Hz), 7.61(1H, dd, J=2.0, 8.8 Hz), 7.79(1H, d, J=8.8 Hz), 7.81(1H, d, J=7.2 Hz), 8.04(1H, dd, J=2.0, 7.2 Hz), 8.79(1H, s), 8.46(1H, d, J=6.0 Hz), 9.13(1H, s).

Preparation Example 41
1-Chloro-6-ethoxycarbonylaminoisoquinoline

The title compound (173 mg, 60%, 2 steps) was obtained as pale yellow crystals in the same manner as in Preparation Example 22, except using 6-ethoxycarbonylaminoisoquinoline-N-oxide (250 mg).

$^1$H-NMR(CDCl$_3$) δ (ppm): 1.34(3H, t, J=7.2 Hz), 4.29 (2H, q, J=7.2 Hz), 7.36(1H, brs), 7.50(1H, d, J=5.6 Hz), 7.52(1H, dd, J=2.4, 9.2 Hz), 8.11(1H, m), 8.19(1H, d, J=5.6 Hz), 8.22(1H, d, J=9.2 Hz).

Preparation Example 42
1-Methoxy-6-methoxycarbonylaminoisoquinoline

In dimethyl sulfoxide (45 ml) was dissolved 2.27 g of 1-chloro-6-ethoxycarbonylaminoisoquinoline (Preparation Example 41). To the mixture was added 28% sodium methoxide solution (8.7 ml), followed by heating under stirring at 110° C. for 1.5 hours. After cooling to room temperature as it was, an aqueous saturated ammonium chloride was added thereto and the mixture was extracted with ethyl acetate. The extract was washed with brine, dried over anhydrous magnesium sulfate and the solvent was evaporated, to give the title compound (1.75 g, 84%) as a brown oil.

$^1$H-NMR(CDCl$_3$) δ (ppm): 3.74(3H, s), 4.03(3H, s), 7.05 (1H, d, J=5.8 Hz), 7.41(1H, dd, J=2.0, 9.2 Hz), 7.86(1H, d, J=5.8 Hz), 7.90(1H, brs), 8.06(1H, d, J=9.22 Hz), 8.08(1H, brs).

Preparation Example 43
6-Amino-1-methoxyisoquinoline

The title compound (1.04 g, 99%) was obtained as light brown crystals in the same manner as in Preparation Example 41, except using 1-methoxy-6-methoxycarbonylaminoisoquinoline (1.75 g, Preparation Example 42) and methanol as a solvent.

$^1$H-NMR(CDCl$_3$) δ (ppm): 4.07(3H, s), 4.07(2H, brs), 6.78(1H, d, J=2.2 Hz), 6.88(1H, dd, J=2.2, 8.8 Hz), 6.95(1H, d, J=6.0 Hz), 7.84(1H, d, J=6.0 Hz), 8.03(1H, d, J=8.8 Hz).

Preparation Example 44
N-Propynyl-(3-nitrophenethyl)amine

The title compound (3.070 g, 77%, including impurities) was obtained as a yellow oil in the same manner as in Preparation Example 28, except using 3-nitrophenethylamine (3.0 g, Preparation Example 27) and propionyl chloride (2.5 ml).

$^1$H-NMR(CDCl$_3$) δ (ppm): 1.14(3H, t, J=7.6 Hz), 2.19 (2H, q, J=7.6 Hz), 2.96(2H, t, J=6.8 Hz), 3.56(2H, dt, J=6.4, 6.8 Hz), 7.49(1H, dd, J=7.6, 8.0 Hz), 7.55(1H, d, J=7.6 Hz), 8.07(1H, s), 8.10(1H, d, J=8.0 Hz).

Preparation Example 45
N-Propynyl-(3-aminophenethyl)amine

A similar reaction to that in Preparation Example 29 was performed using N-propynyl-(3-nitrophenethyl)amine (3.070 g, Preparation Example 44). The resulting residue was purified by silica gel column, to give the title compound (0.857 g, 32%) as a pale yellow oil.

$^1$H-NMR(CDCl$_3$) δ (ppm): 1.12(3H, t, J=7.6 Hz), 2.19 (2H, q, J=7.6 Hz), 2.71(2H, t, J=6.8 Hz), 3.49(2H, dt, J=6.0, 6.8 Hz), 5.56(1H, brs), 6.52(1H, s), 6.56(1H, d, J=7.6 Hz), 6.56(1H, d, J=7.6 Hz), 7.09(1H, dd, J=7.6, 7.6 Hz).

Preparation Example 46
N-Propynyl-(3-ethoxycarbonylaminophenethyl)amine

A similar reaction to that in Preparation Example 30 was performed using N-propynyl-(3-aminophenethyl)amine (0.857 g, Preparation Example 45). The resulting residue was purified by silica gel column, to give the title compound (0.747 g, 61%) as a light-colored oil.

$^1$H-NMR(CDCl$_3$) δ (ppm): 1.12(3H, t, J=7.6 Hz), 1.30 (3H, t, J=7.0 Hz), 2.16(2H, q, J=7.6 Hz), 2.78(2H, t, J=6.8 Hz), 3.50(2H, dt, J=6.0, 6.8 Hz), 4.21(2H, q, J=7.0 Hz), 6.67(1H, brs), 6.87(1H, d, J=6.8 Hz), 7.00(1H, brs), 7.22 (1H, dd, J=6.8, 8.4 Hz), 7.26(1H, d, J=8.4 Hz), 7.28(1H, s).

Preparation Example 47
6-Ethoxycarbonylamino-1-ethylisoquinoline

The procedures of Preparation Examples 31 and 32 were repeated, except using N-propynyl-(3-ethoxycarbonylaminophenethyl)amine (0.747 g, Preparation Example 46), to give 6-ethoxycarbonylamino-1-ethyl-3,4-dihydroxyisoquinoline as brown crystals, and then the title compound (0.516 g, 75%, 2 steps) as a yellow oil.

The data of the intermediate and the title compound are as follows.

6-Ethoxycarbonylamino-1-ethyl-3,4-dihydroisoquinoline $^1$H-NMR(CDCl$_3$) δ (ppm): 1.21(3H, t, J=7.6 Hz), 1.30 (3H, t, J=7.0 Hz), 2.66(2H, t, J=7.4 Hz), 2.74(2H, q, J=7.6 Hz), 3.64(2H, t, J=7.4 Hz), 4.23(2H, q, J=7.0 Hz), 7.32(1H, d, J=8.4 Hz), 7.37(1H, s), 7.43(1H, d, J=8.4 Hz), 7.79(1H, s).

6-Ethoxycarbonylamino-1-ethylisoquinoline $^1$H-NMR(CDCl$_3$) δ (ppm): 1.32(3H, t, J=7.0 Hz), 1.41 (3H, t, J=7.6 Hz), 3.27(2H, q, J=7.6 Hz), 4.27(2H, q, J=7.0 Hz), 7.40(1H, d, J=6.0 Hz), 7.52(1H, dd, J=2.0, 8.8 Hz), 7.89(1H, s), 8.02(1H, d, J=2.0 Hz), 8.25(1H, d, J=8.8 Hz), 8.34(1H, J=6.0 Hz).

Preparation Example 48
6-Amino-1-ethylisoquinoline

The title compound (0.320 g, 88%) was obtained as pale yellow crystals in the same manner as in Preparation Example 33, except using 6-ethoxycarbonylamino-1-ethylisoquinoline (0.516 g, Preparation Example 47).

$^1$H-NMR(CDCl$_3$) δ (ppm): 1.31(3H, t, J=7.2 Hz), 3.21 (2H, q, J=7.2 Hz), 4.20(2H, brs), 6.82(1H, d, J=2.4 Hz), 6.95(1H, dd, J=2.4, 8.8 Hz), 7.21(1H, d, J=6.0 Hz), 7.94(1H, d, J=8.8 Hz), 8.24(1H, d, J=6.0 Hz).

Preparation Example 49
1-Ethoxy-4-(3-nitrophenyl)propan-1-ene

Methoxymethylphosphonium chloride (31.1 g) was suspended in tetrahydrofuran (200 ml), followed by adding potassium t-butoxide (10.2 g) thereto under ice-cooling. At the time when the reaction mixture became red, a solution of 3-nitroacetophenone (10 g) in tetrahydrofuran (100 ml) was added thereto by portions using a pipette. After stirring at room temperature for 2.5 hours, an aqueous saturated ammonium chloride was added thereto under ice-cooling. The mixture was extracted with ethyl acetate, and the extract was washed with brine, dried over anhydrous magnesium sulfate and the solvent was evaporated. The resulting residue was purified by silica gel column, to give the title compound (8.010 g) as a yellow oil.

Preparation Example 50
2-(3-Nitrophenyl)propanal

To 1-methoxy-4-(3-nitrophenyl)propan-1-ene (8.010 g) was added 2 N hydrochloric acid (150 ml), followed by heating under stirring at 80° C. for 4 hours. Then, hydrochloric acid (5 ml) was added thereto, followed by heating under reflux for 2.5 hours. After cooling, the reaction mixture was neutralized with an aqueous sodium hydroxide and extracted with ethyl acetate. The extract was washed with brine, dried over anhydrous magnesium sulfate and the solvent was evaporated, to give the title compound (7.531 g) as a yellow oil.

Preparation Example 51
2-(3-Nitrophenyl)propan-1-ol

In ethanol (100 ml) was dissolved 7.531 g of 2-(3-nitrophenyl)propanal. Under ice-cooling, sodium borohydride (1.9 g) was added thereto, followed by stirring at room temperature for 1 hour. To the mixture was added brine, followed by extracting with ethyl acetate. The extract was washed with brine, dried over anhydrous magnesium sulfate and the solvent was evaporated. The resulting residue was purified by silica gel column, to give the title compound (6.275 g, 57.19% in 3 steps) as a brown oil.

$^1$H-NMR(CDCl$_3$) δ (ppm): 1.34(3H, d, J=6.8 Hz), 1.51 (1H, brs), 3.09(1H, tq, J=6.8, 6.8 Hz), 3.78(2H, d, J=6.8 Hz), 7.50(1H, dd, J=7.6, 8.4 Hz), 7.60(1H, ddd, J=1.2, 1.6, 7.6 Hz), 8.10(1H, ddd, J=1.2, 2.4, 8.4 Hz), 8.13(1H, dd, J=1.6, 2.4 Hz).

Preparation Example 52
2-(3-Nitrophenyl)propylamine

The title compound was obtained as a yellow oil by the procedures of Preparation Examples 26 and 27, except using 2-(3-nitrophenyl)propan-1-ol (1.908 g, Preparation Example 51).

Preparation Example 53
1-t-Butoxycarbonylamino-2-(3-nitrophenyl)propane

A similar reaction to that in Preparation Example 35 was performed using 2-(3-nitrophenyl)propylamine obtained in Preparation Example 52. The resulting residue was purified by silica gel column, to give the title compound (2.626 g) as a yellow oil.

$^1$H-NMR(CDCl$_3$) δ (ppm): 1.31(3H, d, J=6.8 Hz), 1.40 (9H, s), 3.10(1H, m), 3.26(1H, m), 3.38(1H, m), 7.49(1H, dd, J=7.6, 8.4 Hz), 7.56(1H, d, J=7.6 Hz), 8.08(1H, s), 8.10(1H, d, J=8.4 Hz).

Preparation Example 54
2-(3-Aminophenyl)-1-t-butoxycarbonylaminopropane

The title compound was obtained as a yellow oil by the procedure of Preparation Example 29, except using the above prepared 1-t-butoxycarbonylamino-2-(3-nitrophenyl) propane (2.626 g).

Preparation Example 55
1-t-Butoxycarbonylamino-2-(3-ethoxycarbonylaminophenyl)propane A similar reaction to that in Preparation Example 30 was performed using the above-prepared 2-(3-aminophenyl)-1-t-butoxycarbonylaminopropane. The resulting residue was purified by silica gel column, to give the title compound (2.960 g, 77.56% in 3 steps) as a brown oil.

$^1$H-NMR(CDCl$_3$) δ (ppm): 1.25(3H, d, J=7.6 Hz), 1.31 (3H, t, J=7.2 Hz), 1.41(9H, s), 2.90(1H, m), 3.18(1H, ddd, J=4.2, 7.6, 9.2 Hz), 3.39(1H, m), 4.42(2H, q, J=7.6 Hz), 4.45(1H, brs), 6 87(1H, brs), 6.94(1H, m), 7.22(3H, m).

Preparation Example 56
6-Ethoxycarbonylamino-4-methyl-1,2,3,4-tetrahydroisoquinoline The title compound (2.967 g, crude) was obtained as a yellow solid by the procedures of Preparation Examples 38 and 39, except using 1-t-butoxycarbonylamino-2-(3-ethoxycarbonylaminophenyl)propane (2.960 g, Preparation Example 55)

Preparation Example 57
6-Ethoxycarbonylamino-4-methylisoquinoline

The title compound (2.061 g, crude) was obtained as pale yellow crystals by a similar reaction to that in Preparation Example 40, except using the above-prepared 6-ethoxycarbonylamino-4-methyl-1,2,3,4-tetrahydroisoquinoline (2.967 g, crude).

$^1$H-NMR(CDCl$_3$) δ (ppm): 1.36(3H, t, J=7.2 Hz), 2.59 (3H, s), 4.30(2H, q, J=7.2 Hz), 7.12(1H, d, J=2.0 Hz), 7.49(1H, dd, J=2.0, 8.8 Hz), 7.91(1H, d, J=8.8 Hz), 8.12(1H, s), 8.32(1H, s), 9.00(1H, s).

Preparation Example 58
6-Amino-4-methylisoquinoline

The above-prepared 6-ethoxycarbonylamino-4-methylisoquinoline (2.061 g, crude) was subjected to a reaction in the same manner as in Preparation Example 30. The resulting crystals were washed with diethyl ether and dried, to give the title compound (0.403 g, 27.75% in 4 steps) as pale yellow crystals.

$^1$H-NMR(CDCl$_3$) δ (ppm): 2.48(3H, s), 4.18(2H, brs), 6.95(1H, d, J=2.0 Hz), 7.00(1H, dd, J=2.0, 8.8 Hz), 7.76(1H, d, J=8.8 Hz), 8.19(1H, s), 8.86(1H, s).

Preparation Example 59
2-(3-Nitrophenyl)butan-1-ol

The title compound (5.456 g, 50.08% in 3 steps) was obtained as a yellow oil by the procedures of Preparation Examples 52 to 55, except using 3-nitropropiophenone (10 g).

$^1$H-NMR(CDCl$_3$) δ (ppm): 0.86(3H, t, J=7.4 Hz), 1.63 (1H, m), 1.85(1H, m), 3.24(1H, m), 3.83(2H, m), 7.50(1H, dd, J=7.2, 8.0 Hz), 7.57(1H, d, J=8.0 Hz), 8.10(1H, s), 8.13(1H, d, J=7.2 Hz).

Preparation Example 60
2-(3-Nitrophenyl)butylamine

The title compound (5.247 g) was obtained as a yellow oil by the procedures of Preparation Examples 26 and 27, except using 2-(3-nitrophenyl)butan-1-ol (5.456 g, Preparation Example 59).

Preparation Examples 61
1-t-Butoxycarbonylamino-2-(3-nitrophenyl)butane

Then, the above-prepared 2-(3-nitrophenyl)butylamine (5.247 g) was subjected to the reaction in the same manner as in Preparation Example 27. The resulting residue was purified by silica gel column, to give the title compound (7.679 g) as a pale yellow oil.

$^1$H-NMR(CDCl$_3$) δ (ppm): 0.83(3H, t, J=7.4 Hz), 1.39 (9H, s), 1.63(1H, m), 1.79(1H, m), 2.84(1H, m), 3.21(1H, m), 3.52(1H, m), 4.42(1H, brs), 7.49(1H, d, J=7.6 Hz), 7.52(1H, dd, J=6.8, 7.6 Hz), 8.04(1H, s), 8.10(1H, d, J=6.8 Hz).

Preparation Example 62
2-(3-Aminophenyl)-1-t-butoxycarbonylaminobutane

The title compound (6.311 g, 85.40% in 4 steps) was obtained as a yellow oil by the procedure of Preparation Example 29, except using 1-t-butoxycarbonylamino-2-(3-nitrophenyl)butane (7.679 g).

Preparation Example 63
1-t-Butoxycarbonylamino-2-(3-ethoxycarbonylaminophenyl)butane The above-prepared compound was then treated in the same manner as in Preparation Example 30, to give the title compound (8.230 g, crude) as an orange solid.

$^1$H-NMR(CDCl$_3$) δ (ppm): 0.81(3H, t, J=7.4 Hz), 1.31 (3H, t, J=7.2 Hz), 1.40(9H, s), 1.55(1H, m), 1.68(1H, m), 2.63(1H, m), 3.14(1H, ddd, J=4.8, 8.8, 13.6 Hz), 3.52(1H, m), 4.22(2H, q, J=7.2 Hz), 4.38(1H, brs), 6 63(1H, brs), 6.87(1H, m), 7.23(3H, m).

Preparation Example 64
6-Ethoxycarbonylamino-4-ethyl-1,2,3,4-tetrahydroisoquinoline The title compound was obtained as a brown oil by the procedures of Preparation Examples 38 and 39, except using 1-t-butoxycarbonylamino-2-(3-ethoxycarbonylaminophenyl)butane (8.230 g, crude, Preparation Example 63).

Preparation Example 65
6-Ethoxycarbonylamino-4-ethyl-isoquinoline

The above-prepared 6-ethoxycarbonylamino-4-ethyl-1,2,3,4-tetrahydroisoquinoline (3.0 g) was subjected to the reaction in the same manner as in Preparation Example 40. The resulting crude crystals were washed with ethanol-diethyl ether and dried, to give the title compound as orange crystals.

$^1$H-NMR(DMSO-d$_6$) δ (ppm): 1.27(3H, t, J=7.2 Hz), 1.28(3H, t, J=7.2 Hz), 2.91(2H, q, J=7.2 Hz), 4.18(2H, q, J=7.2 Hz), 7.64(1H, d, J=8.8 Hz), 8.00(1H, d, J=8.8 Hz), 8.25(1H, s), 8.27(1H, s), 8.98(1H, s), 10.12(1H, s).

Preparation Example 66
6-Amino-4-ethyl-isoquinoline

The above-prepared 6-ethoxycarbonylamino-4-ethylisoquinoline was subjected to the reaction in the same manner as in Preparation Example 30. The resulting residue was purified by NH-silica gel column, and the resulting crude crystals were washed with diethyl ether and dried, to give the title compound (0.637 g) as orange crystals.

$^1$H-NMR(CDCl$_3$) δ (ppm): 1.35(3H, t, J=7.6 Hz), 2.92 (2H, q, J=7.6 Hz), 4.17(2H, brs), 6.99(1H, d, J=8.4 Hz), 7.00(1H, s), 7.77(1H, d, J=8.4 Hz), 8.21(1H, s), 8.86(1H, s).

Preparation Example 67
Diethyl Methyl-(3-nitrobenzyl)malonate

In ethanol (45 ml) was dissolved sodium (0.7 g), and diethyl methylmalonate (5.26 ml) and 3-nitrobenzyl chloride (5 g) were added thereto, followed by heating under reflux for 2 hours. The reaction mixture was ice-cooled, an aqueous saturated ammonium chloride was added thereto, followed by extracting with ethyl acetate. The extract was washed with brine, dried over anhydrous magnesium sulfate and the solvent was evaporated, to give the title compound (9.724 g) as a pale yellow oil.

$^1$H-NMR(CDCl$_3$) δ (ppm): 1.27(6H, t, J=7.2 Hz), 1.37 (3H, s), 3.32(2H, s), 4.21(4H, q, J=7.2 Hz), 7.44(1H, d, J=7.6 Hz), 7.48(1H, dd, J=7.6, 7.6 Hz), 8.03(1H, s), 8.11 (1H, d, J=7.6 Hz).

Preparation Example 68
Ethyl 1-Methyl -2-(3-nitrophenyl)propionate

In dimethyl sulfoxide (30 ml) was dissolved the above-prepared diethyl methyl(3-nitrobenzyl)malonate (9.724 g), and water (0.54 ml) and lithium chloride (2.54 g) were added thereto, followed by heating under reflux at 190° C. for 3.5 hours. After cooling as it was, water was added thereto, followed by extracting with ethyl acetate. The extract was washed with brine, dried over anhydrous magnesium sulfate and the solvent was evaporated, to give the title compound (5.071 g, 73.35% in 2 steps) as a brown oil.

$^1$H-NMR(CDCl$_3$) δ (ppm): 1.20(3H, t, J=7.2 Hz), 1.21 (3H, d, J=7.2 Hz), 2.79(2H, m), 3.10(1H, m), 4.10(2H, q, J=7.2 Hz), 7.45(1H, dd, J=7.6, 8.0 Hz), 7.52(1H, d, J=7.6 Hz), 8.06(1H, s), 8.08(1H, d, J=8.0 Hz).

Preparation Example 69
1-Methyl -2-(3-nitrophenyl)propionic acid

In ethanol (50 ml) was dissolved 5.071 g of ethyl 1-methyl-2-(3-nitrophenyl)propionate (Preparation Example 68), and 5 N sodium hydroxide aqueous solution (43 ml) was added thereto, followed by heating under reflux for 2.5 hours. After cooling as it was, diethyl ether and water were added thereto, to separate the aqueous layer. The organic layer was extracted with brine. The aqueous layers were combined, acidified with dilute hydrochloric acid, and then extracted with diethyl ether. The extract was washed with brine, dried over anhydrous magnesium sulfate and the solvent was evaporated. The resulting residue was purified by silica gel column, to give the title compound (2.918 g, 65.27%) as a red oil.

$^1$H-NMR(CDCl$_3$) δ (ppm): 1.24(3H, d, J=6.0 Hz), 2.83 (2H, s), 3.16(1H, m), 7.47(1H, dd, J=7.2, 8.0 Hz), 7.54(1H, d, J=7.2 Hz), 8.08(1H, s), 8.10(1H, d, J=8.0 Hz).

Preparation Example 69
N-Boc-1-methyl-2-(3-nitrophenyl)ethylamine

In t-butanol (36 ml) was dissolved 2.918 g of 1-methyl-2-(3-nitrophenyl)propionic acid (Preparation Example 69), and triethylamine (4.09 ml) and diphenylphosphorylazide were added thereto, followed by heating under reflux for 2.5 hours. After standing to cool, the solvent was evaporated. To the residue was added saturated sodium bicarbonate, followed by extracting with ethyl acetate. The extract was washed with brine, dried over anhydrous magnesium sulfate and the solvent was evaporated. The resulting residue was purified by silica gel column, to give the title compound (2.117 g, 54.14%) as yellow crystals.

$^1$H-NMR(CDCl$_3$) δ (ppm): 1.13(3H, d, J=6.8 Hz), 2.82 (1H, m), 2.92(1H, m), 3.94(1H, brs), 7.47(1H, dd, J=7.2, 8.0 Hz), 7.54(1H, d, J=7.2 Hz), 8.05(1H, s), 8.09(1H, d, J=8.0 Hz).

Preparation Example 71
N-Boc-2-(3-aminophenyl)-1-methylethylamine

N-Boc-1-methyl-2-(3-aminophenyl)-1-methylethylamine (2.117 g, Preparation Example 70) was subjected to the reaction in the same manner as in Preparation Example 29. After extracting, the resulting residue was purified by silica gel column, to give the title compound (0.976 g, 51.63%) as a yellow oil.

Preparation Example 72
N-Boc-1-methyl-2-(3-ethoxycarbonylaminophenyl) ethylamine The title compound (1.173 g, crude) was obtained as a yellow oil by the procedure of Preparation Example 30, except using N-Boc-2-(3-aminophenyl)-1-methylethylamine (0.976 g). The obtained compound was subjected to a subsequent reaction as intact without further purification.

$^1$H-NMR(CDCl$_3$) δ (ppm): 1.09(3H, d, J=6.4 Hz), 1.31 (3H, t, J=7.2 Hz), 1.43(9H, s), 2.62(1H, dd, J=6.8 Hz, 13.2 Hz), 2.82(1H, m), 3.88(1H, m), 4.22(2H, q, J=7.2 Hz), 4.38(1H, m), 6.56(1H, m), 6.89(1H, d, J=6.8 Hz), 7.18(1H, s), 7.22(1H, dd, J=6.8, 8.0 Hz), 7.23(1H, d, J=8.0 Hz).

Preparation Example 73
2-(3-Ethoxycarbonylaminophenyl)-1-methylethylamine hydrochloride In ethanol (5 ml) was dissolved 1.173 g of N-Boc-1-methyl-2-(3-ethoxycarbonylaminophenyl)ethylamine (crude), and hydrochloric acid (5 ml) was added thereto, followed by stirring at room temperature for 1.5 hours. Then, hydrochloric acid (2.5 ml) was further added thereto, followed by stirring at room temperature for 2 hours. The solvent was evaporated, to give the title compound (1.148 g, crude) as a yellow oil. The obtained compound was subjected to the subsequent reaction as intact without further purification.

$^1$H-NMR(DMSO-d$_6$) δ (ppm): 1.03(3H, d, J=6.8 Hz), 1.22(3H, t, J=7.2 Hz), 2.55(1H, m), 2.95(1H, m), 3.32(1H, m), 4.10(2H, q, J=7.2 Hz), 6.84(1H, d, J=7.2 Hz), 7.21(1H, dd, J=7.2, 7.2 Hz), 7.29(1H, d, J=7.2 Hz), 7.35(1H, s), 8.00(1H, brs), 9.60(1H, s).

Preparation Example 74
6-Ethoxycarbonylamino-3-methyl-1,2,3,4-tetrahydroisoquinoline The title compound (0.441 g) was obtained by performing the reaction by the procedure described in Chem. Pharm. Bull. 42(8), 1676 (1994) using 2-(3-ethoxycarbonylaminophenyl)-1-methylethylamine hydrochloride (1.148 g, Preparation Example 73) and purifying the product by NH-silica gel column.

$^1$H-NMR(CDCl$_3$) δ (ppm): 1.24(3H, d, J=6.4 Hz), 1.30 (3H, t, J=7.2 Hz), 2.48(1H, dd, J=10.0 Hz, 16.4 Hz), 2.75(1H, dd, J=3.6 Hz, 16.4 Hz), 3.01(1H, m), 4.03(2H, brq), 4.21(2H, q, J=7.2 Hz), 6.66(1H, s), 6.95(1H, d, J=8.4 Hz), 7.09(1H, d, J=8.4 Hz), 7.14(1H, s).

Preparation Example 75
6-Ethoxycarbonylamino-3-methylisoquinoline

The title compound (0.356 g) was obtained by the procedure of Preparation Example 39, except using the above-prepared 6-ethoxycarbonylamino-3-methyl-1,2,3,4-tetrahydroisoquinoline (0.441 g).

$^1$H-NMR(CDCl$_3$) δ (ppm): 1.34(3H, t, J=7.2 Hz), 2.67 (3H, s), 4.28(2H, q, J=7.2 Hz), 7.08(1H, brs), 7.39(1H, dd, J=2.0, 8.8 Hz), 7.40(1H, s), 7.85(1H, d, J=8.8 Hz), 7.94(1H, brs), 9.05(1H, s).

Preparation Example 76
6-Amino-3-methylisoquinoline

The above-prepared 6-ethoxycarbonylamino-3-methylisoquinoline (0.356 g) was subjected to the reaction in the same manner as in Preparation Example 33, to give crude crystals (0.182 g). The crystals were washed with diethyl ether and dried, to give the title compound (93 mg) as pale yellow crystals.

$^1$H-NMR(CDCl$_3$) δ (ppm): 2.63(3H, s), 4.14(2H, brs), 6.77(1H, d, J=2.0 Hz), 6.93(1H, dd, J=2.0, 8.8 Hz), 7.18(1H, s), 7.72(1H, d, J=8.8 Hz), 8.9

Example 1
N-(8-Bromoquinolin-3-yl)-3-pyridinesulfonamide

In pyridine (5 ml) was dissolved 3-amino-8-bromoquinoline (Preparation Example 5) was dissolved in pyridine (5 ml), and 3-pyridinesulfonyl chloride (254 mg) was added thereto, followed by stirring at room temperature for 30 minutes. After the completion of the reaction, the reaction mixture was poured onto brine, and extracted with ethyl acetate. The organic layer was dried over magnesium sulfate and then concentrated. The resulting crude crystals were washed with ethyl acetate and IPA, to give the title compound (270 mg).

$^1$H-NMR(DMSO-d$_6$) δ (ppm): 7.47(1H, t, J=8.0 Hz), 7.52–7.60(1H, m), 7.99–8.03(2H, m), 8.10(1H, d, J=2.4 Hz), 8.18–8.22(1H, m), 8.71(1H, d, J=2.4 Hz), 8.78(1H, dd, J=1.6 Hz, 4.8 Hz), 8.98(1H, d, J=2.4 Hz), 11.23(1H, br s).

Example 2
N-(5-Bromoquinolin-2-yl)-5-methyl-3-pyridinesulfonamide

The title compound was obtained from 2-amino-5-bromoquinoline (Preparation Example 1) and 5-methyl-3-pyridinesulfonyl chloride by the procedure of Example 1.

$^1$H-NMR(DMSO-d$_6$) δ (ppm): 2.37(3H, s), 7.58–7.72 (4H, m), 8.11(1H, br s), 8.37(1H, d, J=9.6 Hz), 8.59(1H, d, J=1.2 Hz), 8.86(1H, br s).

Example 3
6-Amino-N-(8-bromoquinolin-3-yl)-3-pyridinesulfonamide

The title compound was obtained from 3-amino-8-bromoquinoline (Preparation Example 5) and 6-amino-3-pyridinesulfonyl chloride by the procedure of Example 1.

$^1$H-NMR(DMSO-d$_6$) δ (ppm): 6.40(1H, d, J=8.8 Hz), 6.93(2H, brs), 7.44(1H, t, J=8.0 Hz), 7.65(1H, dd, J=2.4 Hz, 8.8 Hz), 7.96–7.99(2H, m), 8.01(1H, d, J=2.4 Hz), 8.31(1H, d, J=2.4 Hz), 8.70(1H, d, J=2.4 Hz), 10.73(1H, br s).

Example 4
N-(8-Bromoquinolin-3-yl)-4-cyanobenzenesulfonamide

The title compound was obtained from 3-amino-8-bromoquinoline (Preparation Example 5) and 4-cyanobenzenesulfonyl chloride by the procedure of Example 1.

$^1$H-NMR(DMSO-d$_6$) δ (ppm): 7.46(1H, t, J=8.0 Hz), 7.96–8.07(7H, m), 8.70(1H, d, J=2.4 Hz), 11.27(1H, br s).

Example 5
6-Chloro-N-(8-bromoquinolin3-yl)-3-pyridinesulfonamide

The title compound was obtained from 3-amino-8-bromoquinoline (Preparation Example 5) and 6-chloro-3-pyridinesulfonyl chloride by the procedure of Example 1.

$^1$H-NMR(DMSO-d$_6$) δ (ppm): 7.47(1H, t, J=8.0 Hz), 7.71(1H, d, J=8.4 Hz), 7.99–8.03(2H, m), 8.10(1H, d, J=2.4 Hz), 8.20(1H, dd, J=8.4 Hz), 8.71(1H, d, J=2.4 Hz), 8.83 (1H, d, J=2.4 Hz), 10.73(1H, br s).

Example 6
N-(8-Bromoquinolin-3-yl)-4-(N-ethylsulfamoyl)benzenesulfonamide

The title compound was obtained from 3-amino-8-bromoquinoline (Preparation Example 5) and 4-(N-ethylsulfamoyl)benzenesulfonyl chloride by the procedure of Example 1.

$^1$H-NMR(DMSO-$d_6$) δ (ppm): 0.82(3H, t, J=7.2 Hz), 2.69–2.76(2H, m), 7.45(1H, t, J=8.4 Hz), 7.75(1H, t, J=5.6 Hz), 7.90–8.04(7H, m), 8.70(1H, d, J=2.8 Hz), 11.18(1H, br s).

Example 7
N-(8-Bromoquinolin-3-yl)-5-cyano-2-pyridinesulfonamide

The title compound was obtained from 3-amino-8-bromoquinoline (Preparation Example 5) and 5-cyano-3-pyridinesulfonyl chloride by the procedure of Example 1.

$^1$H-NMR(DMSO-$d_6$) δ (ppm): 7.46(1H, t, J=8.0 Hz), 7.95(1H, d, J=8.0 Hz), 8.01(1H, d, J=8.0 Hz), 8.11(1H, d, J=2.4 Hz), 8.21(1H, d, J=8.4 Hz), 8.57(1H, dd, J=2.0 Hz, 8.4 Hz), 8.79(1H, d, J=2.4 Hz), 9.14(1H, d, J=2.0 Hz), 11.49 (1H, br s).

Example 8
N-(8-Cyanoquinolin-3-yl) 3-pyridinesulfonamide

The title compound was obtained from 3-amino-8-cyanoquinoline (Preparation Example 7) and 3-pyridinesulfonyl chloride by the procedure of Example 1.

$^1$H-NMR(DMSO-$d_6$) δ (ppm): 7.59(1H, dd, J=4.8 Hz, 8.0 Hz), 7.70(1H, t, J=8.0 Hz), 8.21–8.25(3H, m), 8.33(1H, d, J=8.0 Hz), 8.77–8.79(2H, m), 9.01(1H, d, J=2.8 Hz), 11.34 (1H, br s).

Example 9
N-(8-Cyanoquinolin-3-yl)-4-cyanobenzenesulfonamide

The title compound was obtained from 3-amino-8-cyanoquinoline (Preparation Example 7) and 4-cyanobenzenesulfonyl chloride by the procedure of Example 1.

$^1$H-NMR(DMSO-$d_6$) δ (ppm): 7.71(1H, t, J=8.0 Hz), 7.96–8.07(4H, m), 8.18(1H, d, J=2.8 Hz), 8.24(1H, d, J=8.0 Hz), 8.31(1H, d, J=8.0 Hz), 8.78(1H, d, J=2.8 Hz), 11.37 (1H, br s).

Example 10
N-(5-Bromoquinolin-2-yl)-3-pyridinesulfonamide

The title compound was obtained from 2-amino-5-bromoquinoline (Preparation Example 1) and 3-pyridinesulfonyl chloride by the procedure of Example 1.

$^1$H-NMR(DMSO-$d_6$) δ (ppm): 7.57–7.61(3H, m), 7.70–7.72(2H, m), 8.28(1H, br), 8.38(1H, d, J=9.6 Hz), 8.75(1H, dd, J=1.2 Hz, 4.8 Hz), 9.07(1H, br).

Example 11
N-(8-Bromoquinolin-3-yl)-5-indanesulfonamide

The title compound was obtained from 3-amino-8-bromoquinoline (Preparation Example 5) and 5-indanesulfonyl chloride by the procedure of Example 1.

$^1$H-NMR(DMSO-$d_6$) δ (ppm): 1.92–2.01(2H, m), 2.81–2.86(4H, m), 7.34(1H, d, J=8.0 Hz), 7.44(1H, t, J=8.0 Hz), 7.60(1H, dd, J=1.6 Hz, 8.0 Hz), 7.70(1H, d, J=1.6 Hz), 7.95(1H, d, J=8.0 Hz), 7.97(1H, d, J=8.0 Hz), 8.03(1H, d, J=2.4 Hz), 8.71(1H, d, J=2.4 Hz), 10.93(1H, br s).

Example 12
N-(8-Iodoquinolin-3-yl)-N*-acetyl-5-indolinesulfonamide

The title compound was obtained from 3-amino-8-iodoquinoline (Preparation Example 6) and N-acetyl-6-indolinesulfonyl chloride by the procedure of Example 1.

$^1$H-NMR(DMSO-$d_6$) δ (ppm): 2.11(3H, s), 3.11(2H, t, J=8.4 Hz), 4.06(2H, t, J=8.4 Hz), 7.28(1H, t, J=8.0 Hz), 7.65–7.68(2H, m), 7.93–7.96(2H, m), 8.05(1H, d, J=9.2 Hz), 8.22(1H, dd, J=1.2 Hz, 7.6 Hz), 8.64(1H, d, J=2.4 Hz), 10.87(1H, br s).

Example 13
N-(8-Bromoquinolin-3-yl)-3-quinolinesulfonamide

The title compound was obtained from 3-amino-8-bromoquinoline (Preparation Example 5) and 3-quinolinesulfonyl chloride by the procedure of Example 1.

$^1$H-NMR(DMSO-$d_6$) δ (ppm): 7.38(1H, t, J=8.0 Hz), 7.70–7.74(1H, m), 7.90–8.00(3H, m), 8.07(1H, d, J=8.0 Hz), 8.13(1H, d, J=2.4 Hz), 8.19(1H, dd, J=0.8 Hz, 8.4 Hz), 8.75(1H, d, J=2.4 Hz), 9.00–9.01(1H, m), 9.19(1H, d, J=2.4 Hz), 11.31(1H, br s).

Example 14
N-(8-Bromoquinolin-3-yl)-N*-acetyl-1,2,3,4-tetrahydroquinoline-6-sulfonamide The title compound was obtained from 3-amino-8-bromoquinoline (Preparation Example 5) and N-acetyl-1,2,3,4-tetrahydroquinoline-6-sulfonyl chloride by the procedure of Example 1.

$^1$H-NMR(CDCl$_3$) δ (ppm): 1.69(3H, s), 1.86–2.01(2H, m), 2.77(2H, t, J=6.4Hz), 3.65–3.76(2H, m), 7.11–7.18 (1H, m), 7.38(1H, t, J=7.6Hz), 7.42–7.49(1H, m), 7.77 (1H, dd, J=1.2 Hz, J=7.6 Hz), 7.93 (1H, dd, J=1.2 Hz, J=7.6 Hz), 8.22 (1H, d, J=2.4 Hz), 8.72(1H, J=2.4 Hz).

Example 15
N-(8-Iodoquinolin-3-yl)-4-isoquinolinesulfonamide

The title compound was obtained from 3-amino-8-iodoquinoline (Preparation Example 6) and 4-isoquinolinesulfonyl chloride by the procedure of Example 1.

$^1$H-NMR(DMSO-$d_6$) δ (ppm): 7.26(1H, t, J=8.0 Hz), 7.82–7.86(1H, m), 7.93–7.95(1H, m), 7.98(1H, d, J=2.4 Hz), 8.02–8.06(1H, m), 8.19(1H, dd, J=1.2 Hz, 7.6 Hz), 8.27(1H, d, J=8.4 Hz), 8.59(1H, d, J=2.4 Hz), 8.67(1H, d, J=8.4 Hz), 9.12(1H, s), 9.52(1H, s), 11.57(1H, br s).

Example 16
4-Cyano-N-(8-iodoquinolin-3-yl)-benzenesulfonamide

The title compound was obtained from 3-amino-8-iodoquinoline (Preparation Example 6) and 4-cyanobenzenesulfonyl chloride by the procedure of Example 1.

$^1$H-NMR(DMSO-$d_6$) δ (ppm): 7.31(1H, t, J=8.0 Hz), 7.96–8.04(6H, m), 8.26(1H, dd, J=1.2 Hz, 7.2 Hz), 8.65(1H, d, J=2.8 Hz), 11.24(1H, br s).

Example 17
N-(8-Iodoquinolin-3-yl)-3-pyridinesulfonamide

The title compound was obtained from 3-amino-8-iodoquinoline (Preparation Example 6) and 3-pyridinesulfonyl chloride by the procedure of Example 1.

$^1$H-NMR(DMSO-$d_6$) δ (ppm): 7.31(1H, t, J=8.0 Hz), 7.57–7.60(1H, m), 7.99(1H, d, J=1.2 Hz, 8.4 Hz), 8.04(1H, d, J=2.8 Hz), 8.18–8.21(1H, m), 8.26(1H, dd, 1.2 Hz, 7.2 Hz), 8.66(1H, d, J=2.8 Hz), 8.77(1H, dd, J=1.6 Hz, 4.8 Hz), 8.98(1H, d, J=2.8 Hz), 11.20(1H, br s).

Example 18
N-(5-Bromoquinolin-2-yl)-4-cyanobenzenesulfonamide

The title compound was obtained from 2-amino-5-bromoquinoline (Preparation Example 1) and 4-cyanobenzenesulfonyl chloride by the procedure of Example 1.

$^1$H-NMR(DMSO-d$_6$) δ (ppm): 7.57–7.73(4H, m), 8.00–8.08(4H, m), 8.38(1H, d, J=8.8 Hz).

Example 19
N-(8-Bromoquinolin-3-yl)-6-ethyl-3-pyridinesulfonamide

Pyridine (0.5 ml) and a solution of 6-ethyl-3-pyridinesulfonyl chloride (30 mg) in methylene chloride (0.5 ml) were added to 3-amino-8-bromoquinoline (18 mg, Preparation Example 5) at 0° C. After stirring at room temperature for 30 minutes, water was added thereto and the mixture was extracted with ethyl acetate. The extract was purified by preparative TLC (hexane-ethyl acetate=1:1), to give the title compound (20 mg).

$^1$H-NMR(CDCl$_3$) δ (ppm): 1.25(3H, t, J=7.5 Hz), 2.70 (2H, q, J=7.50 Hz), 7.34–7.98(5H, m), 8.19(1H, d, J=3.3 Hz), 8.54(1H, s), 8.83(1H, d, J=3.3 Hz).

Example 20
4-Chloro-N-(5-chloroquinolin-2-yl)-benzenesulfonamide

Pyridine (1 ml) and 4-chlorobenzenesulfonyl chloride (255 mg) were added to 2-amino-5-chloroquinoline (119 mg, Preparation Example 2) at room temperature. After stirring at room temperature for 3 days, water was added thereto and the mixture was extracted with ethyl acetate. The ethyl acetate layer was dried over sodium sulfate and concentrated. Then, the resulting solid was washed with methanol, to give the title compound (20 mg).

$^1$H-NMR(CDCl$_3$) δ (ppm): 6.96(1H, d, J=9.7 Hz), 7.34 (1H, d, J=8.4 Hz), 7.42–7.48(3H, m), 7.54(1H, t, J=8.4 Hz), 7.94(2H, d, J=6.3 Hz), 8.29(1H, d, J=9.7 Hz).

Example 21
N-(8-Chloroquinolin-3-yl)-6-ethyl -3-pyridinesulfonamide

The title compound was obtained from 3-amino-8-chloroquinoline (Preparation Example 9) and 6-ethyl-3-pyridinesulfonyl chloride by the procedure of Example 1.

$^1$H-NMR(CDCl$_3$) δ (ppm): 1.28(3H, t, J=8.3 Hz), 2.86 (2H, q, J=8.3 Hz), 7.24(1H, d, J=8.0 Hz), 7.49(1H, t, J=8.0 Hz), 7.73(1H, d, J=8.0 Hz), 7.78(1H, d, J=8.0 Hz), 7.95(1H, dd, J=8.0 Hz 2.1 Hz), 8.18(1H, d, J=2.5 Hz), 8.67(1H, d, J=2.5 Hz), 8.93(1H, d, J=2.1 Hz).

Example 22
N-(5-Chloroquinolin-2-yl -6-ethyl-3-pyridinesulfonamide

The title compound was obtained from 2-amino-5-chloroquinoline (Preparation Example 2) and 6-ethyl-3-pyridinesulfonyl chloride by the procedure of Example 1.

$^1$H-NMR(CDCl$_3$) δ (ppm): 1.32(3H, t, J=8.3 Hz), 2.89 (2H, q, J=8.3 Hz), 6.97(1H, d, J=9.4 Hz), 7.29(1H, d, J=8.0 Hz), 7.35(1H, d, J=8.0 Hz), 7.44(1H, d, J=8.0 Hz), 7.56(1H, t, J=8.0 Hz), 8.18(1H, dd, J=8.0 Hz, 2.6 Hz), 8.30(1H, d, J=9.4 Hz), 9.10(1H, d, J=2.6 Hz).

Example 23
N-(8-Chloroquinolin-3-yl)-benzenesulfonamide

The title compound was obtained from 3-amino-8-chloroquinoline (Preparation Example 9) and benzenesulfonyl chloride by the procedure of Example 1.

$^1$H-NMR(CDCl$_3$) δ (ppm): 7.30–7.48(6H, m), 7.84(2H, d, J=7.4 Hz), 8.11(1H, d, J=3.1 Hz), 8.66(1H, d , J=3.1 Hz).

Example 24
4-Cyano-N-(5-chloroquinolin-2-yl)-benzenesulfonamide

The title compound was obtained from 2-amino-5-chloroquinoline (Preparation Example 2) and 4-cyanobenzenesulfonyl chloride by the procedure of Example 1.

$^1$H-NMR(CDCl$_3$) δ (ppm): 6.96(1H, d, J=9.5 Hz), 7.35 (1H, d, J=8.7 Hz), 7.45(1H, d, J=8.7 Hz), 7.57(1H, t, J=8.7 Hz), 7.78(2H, d, J=8.9 Hz), 8.10(2H, d, J=8.9 Hz), 8.33(1H, d, J=9.5 Hz).

Example 25
N-(5-Chloroquinolin-2-yl)-4-methylbenzenesulfonamide

The title compound was obtained from 2-amino-5-chloroquinoline (Preparation Example 2) and 4-toluenesulfonyl chloride by the procedure of Example 1.

$^1$H-NMR(CDCl$_3$) δ (ppm): 2.41(3H, s), 6.98(1H, d, J=9.3 Hz), 7.28(2H, d, J=8.2 Hz), 7.35(1H, d, J=7.9 Hz), 7.41(1H, d, J=7.9 Hz), 7.53(1H, t, J=7.9 Hz), 7.88(2H, d, J=8.2 Hz), 8.26(1H, d, J=9.3 Hz)

Example 26
N-(5-Chloroquinolin-2-yl)-4-sulfamoylbenzenesulfonamide

The title compound was obtained from 2-amino-5-chloroquinoline (Preparation Example 2) and 4-sulfamoylbenzenesulfonyl chloride by the procedure of Example 1.

$^1$H-NMR(CDCl$_3$) δ (ppm): 7.42–7.49(3H, m), 7.58(1H, t, J=8.0 Hz), 8.00–8.12(4H, m,), 8.39(1H, d, J=9.3 Hz).

Example 27
N-(5-Bromoquinolin-2-yl)-4-(N-ethylsulfamoyl) benzenesulfonamide

The title compound was obtained from 3-amino-8-bromoquinoline (Preparation Example 2) and 4-(N-ethylsulfamoyl)benzenesulfonyl chloride by the procedure of Example 1.

$^1$H-NMR(CDCl$_3$) δ (ppm): 1.14(3H, t, J=7.5 Hz), 3.01–3.09(2H, m), 7.08(1H, d, J=9.5 Hz), 7.42(1H, dd, J=7.6 Hz, 1.3 Hz), 7.49(1H, t, J=7.6 Hz),7.65(1H, dd, J=7.6 Hz, 1.3 Hz), 7.96(2H, d, J=8.7 Hz), 8.10(2H, d, J=8.7 Hz), 8.31(1H, d, J=9.5 Hz).

Example 28
3-(Cyano-N-(8-chloroquinolin-3-yl)-benzenesulfonamide

The title compound was obtained from 3-amino-8-chloroquinoline (Preparation Example 9) and 3-cyanobenzenesulfonyl chloride by the procedure of Example 1.

$^1$H-NMR(CDCl$_3$) δ (ppm): 7.52(1H, t, J=7.9 Hz), 7.59 (1H, t, J=7.9 Hz), 7.72–7.86(3H, m, ), 8.00(1H, d, J=7.9 Hz), 8.13(1H, d, J=3.2 Hz), 8.16(1H, s, ), 8.64(1H, d, J=3.2 Hz).

Example 29
N-(8-Chloroquinolin-3-yl)-3-methylbenzenesulfonamide

The title compound was obtained from 3-amino-8-chloroquinoline (Preparation Example 9) and 3-toluenesulfonyl chloride by the procedure of Example 1.

$^1$H-NMR(CDCl$_3$) δ (ppm): 2.35(3H, s), 7.16–7.79(7H, m), 8.09(1H, d, J=2.7 Hz), 8.65(1H, d, J=2.7 Hz).

Example 30
N-(8-Chloroquinolin-3-yl)-3-sulfamoylbenzenesulfonamide

The title compound was obtained from 3-amino-8-chloroquinoline (Preparation Example 9) and 3-sulfamoylbenzenesulfonyl chloride by the procedure of Example 1.

$^1$H-NMR(CDCl$_3$) δ (ppm): 7.46(1H, t, J=7.6 Hz), 7.53 (1H, t, J=7.6 Hz), 7.58–7.78(2H, m, ), 8.00(1H, d, J=7.6 Hz), 8.04(1H, d, J=7.6 Hz), 8.14(1H, d, J=2.8 Hz) 8.47(1H, s), 8.59(1H, d, J=2.8 Hz).

Example 31
N-(8-Methylquinolin-3-yl)-3-pyridinesulfonamide

White crystals (562 mg) were obtained in the same manner as in Example 1, except using 1.02 g (5.2 mmol) of 7-amino-2-chloro-4-methylquinoline (Preparation Example 16) and 0.9 g (5.2 mmol) of 3-pyridinesulfonyl chloride. To 102 mg (0.29 mmol) of the white crystals were added methanol (4 ml), tetrahydrofuran (4 ml) and 10% palladium-carbon (5 mg), followed by stirring in hydrogen atmosphere for 6 hours. The reaction mixture was filtrated through Celite and then evaporated. The residue was washed with ethyl acetate, to give 65 mg of the title compound.

$^1$H-NMR(DMSO-d$_6$) δ (ppm): 2.82(3H, s), 7.64–7.66 (2H, m), 7.73(1H, d, J=5.2 Hz), 8.03(1H, s), 8.30–8.35(2H, m), 8.82(1H, dd, J=1.2, 4.8 Hz), 9.00(1H, d, J=5.2 Hz), 9.11(1H, d, J=2.0 Hz).

Example 32

N-(8-Methylquinolin-3-yl)-4-cyanobenzenesulfonamide

White crystals (358 mg) were obtained in the same manner as in Example 1, except using 305 mg (1.58 mmol) of 7-amino-2-chloro-4-methylquinoline (Preparation Example 16) and 0.48 g (2.4 mmol) of 4-cyanobenzenesulfonyl chloride. To the white crystals (140 mg, 0.38 mmol) were added acetic acid (6 ml), water (2 ml) and zinc (122 mg), followed by stirring at 60 degrees for 15 minutes. The reaction mixture was filtered through Celite and then an aqueous saturated sodium hydrogencarbonate was added thereto, followed by extracting with ethyl acetate. The organic layer was washed with brine, dried over magnesium sulfate and concentrated. Then, the residue was purified by silica gel chromatography, to give 82 mg of the title compound.

$^1$H-NMR(DMSO-d$_6$) δ (ppm): 2.60(3H, s), 7.26(1H, dd, J=1.2, 4.4 Hz), 7.41(1H, dd, J=2.4, 8.8 Hz), 7.64(1H, d, J=2.4 Hz), 7.97–8.06(1H, m), 7.98(2H, d, J=8.4 Hz), 8.04 (2H, d, J=8.4 Hz), 8.66(1H, d, J=4.4 Hz), 11.06(1H, s).

Example 33

N-(6-(6-Chloro-8-cyanoquinolin-3-yl)-3-pyridinesulfonamide

White crystals (764 mg) were obtained in the same manner as in Example 1, except using 3.0 g (13 mmol) of ethyl 7-amino-2-chloroquinoline-4-carboxylate (Preparation Example 13) and 2.3 g (13 mmol) of 3-pyridinesulfonyl chloride. To a solution of 108 mg (0.28 mmol) of the prepared crystals in ethanol (6 ml) was added 1 N sodium hydroxide (0.5 ml), followed by stirring overnight. To the reaction mixture was added 1 N hydrochloric acid, followed by extracting twice with ethyl acetate. The organic layer was washed with brine, dried over magnesium sulfate and concentrated, to give the residue. To a solution of the residue in tetrahydrofuran (10 ml) were added oxalyl chloride (0.04 ml) and one drop of dimethylformamide under ice-cooling, followed by stirring at room temperature for 30 minutes. After 30 minutes, a saturated ammonium aqueous solution (5 ml) was added thereto, followed by stirring for further 10 minutes. To the reaction mixture was added brine, followed by extracting with ethyl acetate. The organic layer was dried over magnesium sulfate and concentrated, to give the residue. To a solution of the residue in tetrahydrofuran (6 ml) were added pyridine (0.06 ml) and trifluoroacetic anhydride (0.05 ml) under ice-cooling, followed by stirring at room temperature for 30 minutes. To the reaction mixture was added brine, followed by extracting with ethyl acetate. The organic layer was dried over magnesium sulfate and concentrated. The residue was purified by silica gel chromatography, to give 37 mg of the title compound.

$^1$H-NMR(DMSO-d$_6$) δ (ppm): 7.62–7.66(1H, m), 7.68–7.72(2H, m), 8.08(1H, d, J=8.8 Hz), 8.23(1H, s), 8.26–8.29(1H, m), 8.81(1H, dd, J=1.6, 4.8 Hz), 9.04(1H, d, J=2.4 Hz).

Example 34

N-(8-Chloroquinolin-3-yl)-4-cyanobenzenesulfonamide

The title compound (58 mg) was obtained by the procedure of Example 1, except using 38 mg (0.21 mmol) of 3-amino-8-chloroquinoline (Preparation Example 9) and 43 mg (0.21 mmol) of 4-cyanobenzenesulfonyl chloride.

$^1$H-NMR(DMSO-d$_6$)δ (ppm): 7.55(1H, t, J=7.6 Hz), 7.84 (1H, d, J=7.6 Hz), 7.95(1H, t, J=7.6 Hz), 7.99(2H, d, J=8.8 Hz), 8.04(2H, d, J=8.8 Hz), 8.09(1H, d, J=2.8 Hz), 8.73(1H, d, J=2.8 Hz), 11.39(1H, s).

Example 35

N-(8-Chloroquinolin-3-yl1)-4-(N-ethylsulfamoyl) benzenesulfonamide

The title compound (36 mg) was obtained in the same manner as in Example 1, except using 36 mg (0.19 mmol) of 3-amino-8-chloroquinoline (Preparation Example 9) and 52 mg (0.19 mmol) of 4-(N-ethylsulfamoyl)benzenesulfonyl chloride.

$^1$H-NMR(DMSO-d$_6$) δ (ppm): 0.84(3H, t, J=7.2 Hz), 2.78–2.71(2H, m), 7.54(1H, t, J=7.6 Hz), 7.77(1H, t, J=6.0 Hz), 7.83(1H, t, J=7.6 Hz), 7.92–7.95(1H, m), 7.93(2H, d, J=8.8 Hz), 8.03(2H, d, J=8.8 Hz), 8.07(1H, d, J=2.4 Hz), 8.73(1H, d, J=2.4 Hz), 11.20(1H, s).

Example 36

N-(8-Chloroquinolin-3-yl)-3-pyridinesulfonamide

The title compound (29 mg) was obtained by the procedure of Example 1, except using 33 mg (0.19 mmol) of 3-amino-8-chloroquinoline (Preparation Example 9) and 33 mg (0.19 mmol) of 3-pyridinesulfonyl chloride.

$^1$H-NMR(DMSO-d$_6$) δ (ppm): 7.54(1H, t, J=7.6 Hz), 7.60(1H, dd, J=4.8, 7.6 Hz), 7.81(1H, d, J=7.6 Hz), 7.94(1H, d, J=7.6 Hz), 8.09(1H, d, J=2.8 Hz), 8.19–8.26(1H, m), 8.72(1H, d, J=2.8 Hz), 8.77(1H, d, J=1.6, 4.8 Hz), 9.00(1H, d, J=2.8 Hz), 11.46(1H, s).

Example 37

N-(8-Chloroquinolin-3-yl)-5-ethylsulfamoyl-2-pyridinesulfonamide

The title compound (10 mg) was obtained by the procedure of Example 1, except using 30 mg (0.17 mmol) of 3-amino-8-chloroquinoline (Preparation Example 9) and 95 mg (0.34 mmol) of 5-ethylsulfamoyl-2-chlorosulfonylpyridine.

$^1$H-NMR(DMSO-d$_6$) δ (ppm): 0.88(3H, t, J=7.6 Hz), 2.79–2.86(2H, m), 7.55(1H, t, J=7.6 Hz), 7.85(1H, t, J=7.6 Hz), 7.94(1H, d, J=7.6 Hz), 8.00(1H, t, J=6.4 Hz), 8.16(1H, d, J=2.8 Hz), 8.27(1H, d, J=8.0 Hz), 8.41(1H, d, J=2.4, 8.0 Hz), 8.84(1H, d, J=2.8 Hz), 9.04(1H, d, J=2.4 Hz), 11.47 (1H, s).

Example 38

N-(8-Trifluoromethylquinolin-3-yl)-4-cyanobenzenesulfonmide

The title compound (59 mg) was obtained by the procedure of Example 1, except using 35 mg (0.17 mmol) of 3-amino-8-trifluoromethylquinoline (Preparation Example 10) and 37 mg (0.18 mmol) of 4-cyanobenzenesulfonyl chloride.

$^1$H-NMR(DMSO-d$_6$) δ (ppm): 7.71(1H, t, J=7.6 Hz), 8.03–8.09(5H, m), 8.19(1H, d, J=2.4 Hz), 8.30(1H, d, J=7.6 Hz), 8.78(1H, d, J=2.4 Hz), 11.72(1H, s).

Example 39

N-(8-Trifluoromethylquinolin-3-yl)-4-(N-ethylsulfamoyl) benzenesulfonamide

The title compound (60 mg) was obtained by the procedure of Example 1, except using 35 mg (0.17 mmol) of 3-amino-8-trifluoromethylquinoline (Preparation Example 10) and 56 mg (0.20 mmol) of 4-(N-ethylsulfamoyl)benzenesulfonyl chloride.

$^1$H-NMR(DMSO-d$_6$) δ (ppm): 0.83(3H, t, J=7.2 Hz), 2.71–2.78(2H, m), 7.69(1H, t, J=8.0 Hz), 7.76(1H, t, J=5.6 Hz), 7.93(1H, d, J=8.8 Hz), 8.04–8.07(3H, m), 8.13(1H, d, J=2.8 Hz), 8.25(1H, d, J=8.0 Hz), 8.75(1H, d, J=2.8 Hz), 11.28(1H, s).

Example 40
N-(8-Trifluoromethylquinolin-3-yl)-3-pyridinesulfonamide

The title compound (71 mg) was obtained by the procedure of Example 1, except using 45 mg (0.21 mmol) of 3-amino-8-trifluoromethylquinoline (Preparation Example 10) and 45 mg (0.25 mmol) of 3-pyridinesulfonyl chloride.

$^1$H-NMR(DMSO-d$_6$) δ (ppm): 7.59–7.63(1H, m), 7.70 (1H, t, J=7.6 Hz), 8.06(1H, d, J=7.6 Hz), 8.20(1H, d, J=2.8 Hz), 8.23–8.24(1H, m), 8.30(1H, d, J=7.6 Hz), 8.76(1H, d, J=2.8 Hz), 8.79(1H, dd, J=1.6, 4.8 Hz), 9.03(1H, d, J=2.0 Hz), 11.64(1H, s).

Example 41
N-(8-Chloroquinolin-3-yl)-1,2,3,4-tetrahydro-6-naphthalenesulfonamide The title compound (46 mg) was obtained by the procedure of Example 1, except using 33 mg (0.19 mmol) of 3-amino-8-chloroquinoline (Preparation Example 9) and 73 mg (0.22 mmol) of 6-chlorosulfonyl-1,2,3,4-tetrahydronaphthalene.

$^1$H-NMR(DMSO-d$_6$) δ (ppm): 1.68(4H, br), 2.71(4H, br), 7.20(1H, t, J=8.4 Hz), 7.52(1H, t, J=7.6 Hz), 7.53(1H, dd, J=2.0, 8.4 Hz), 7.58(1H, d, J=2.0 Hz), 7.80(1H, d, J=7.6 Hz), 7.93(1H, d, J=7.6 Hz), 8.06(1H, d, J=2.4 Hz), 8.73(1H, d, J=2.4 Hz), 10.94(1H, s).

Example 42
N-(8-Chloroquinolin-3-yl)-2,3-dihydro-9-benzofuransulfonamide

The title compound (57 mg) was obtained by the procedure of Example 1, except using 30 mg (0.17 mmol) of 3-amino-8-chloroquinoline (Preparation Example 9) and 44 mg (0.20 mmol) of 5-chlorosulfonyl-2,3-dihydrobenzofuran.

$^1$H-NMR(DMSO-d$_6$) δ (ppm): 3.19(2H, t, J=8.8 Hz), 4.58(2H, t, J=8.8 Hz), 6.86(1H, d, J=8.8 Hz), 7.23(1H, t, J=7.6 Hz), 7.62(1H, dd, J=1.6, 8.8 Hz), 7.72(1H, d, J=1.6 Hz), 7.80(1H, d, J=7.6 Hz), 7.92(1H, d, J=7.6 Hz), 8.03(1H, d, J=2.4 Hz), 8.73(1H, d, J=2.4 Hz), 10.85(1H, s).

Example 43
N-(8-Chloro-4-vinylquinolin-3-yl)-4-cyanobenzenesulfonamide

The title compound (15 mg) was obtained by the procedure of Example 1, except using 30 mg (0.15 mmol) of 3-amino-4-vinyl-8-chloroquinoline (Preparation Example 12) and 36 mg (0.18 mmol) of 4-cyanobenzenesulfonyl chloride.

$^1$H-NMR(DMSO-d$_6$) δ (ppm): 5.29(1H, d, J=17.6 Hz), 5.59(1H, d, J=11.6 Hz), 6.75(1H, dd, J=11.6, 17.6 Hz), 7.59(1H, t, J=8.0 Hz), 7.80(2H, dd, J=8.8 Hz), 7.96(1H, d, J=8.0 Hz), 8.00–8.04(3H, m), 8.74(1H, s), 10.58(1H, s).

Example 44
N-(8-Trifluoromethylquinolin-3-yl)-5-(N-acetylindoline)sulfonamide The title compound (186 mg) was obtained by the procedure of Example 1, except using 109 mg (0.51 mmol) of 3-amino-8-trifluoromethylquinoline (Preparation Example 10) and 200 mg (0.77 mmol) of 5-chlorosulfonyl-N-acetylindoline.

$^1$H-NMR(DMSO-d$_6$) δ (ppm): 2.13(3H, s), 3.14(2H, t, J=8.0 Hz), 4.09(2H, t, J=8.8 Hz), 7.67(1H, t, J=8.4 Hz), 7.69–7.73(2H, m), 8.01(1H, d, J=7.2 Hz), 8.07–8.09(2H, m), 8.24(1H, d, J=8.4 Hz), 8.73(1H, d, J=2.8 Hz), 10.98(1H, s).

Example 45
N-(8-Bromoquinolin-3-yl)-2-methylthio-5-pyridinesufonamide

White crystals (197 mg, 0.556 mmol) were obtained in the same manner as in Example 1, except using 100 mg (0.56 mmol) of 3-amino-8-bromoquinoline (Preparation Example 5) and 142 mg (0.67 mmol) of 2-chloro-5-pyridinesulfonyl chloride. To the crystals (60 mg, 0.17 mmol) were added dimethylformamide (1 ml), pyridine (1 ml) and sodium thiomethoxide (111 mg, 1.6 mmol), followed by stirring at room temperature for 3 hours. TO the reaction mixture was added brine, followed by extracting with ethyl acetate. The organic layer was dried over magnesium sulfate and concentrated. The resulting residue was purified by silica gel chromatography, to give 62 mg of the title compound.

$^1$H-NMR(DMSO-d$_6$) δ (ppm): 3.33(3H, s), 7.47(1H, d, J=8.8 Hz), 7.55(1H, t, J=8.0 Hz), 7.84(1H, d, J=6.8 Hz), 7.97(1H, d, J=8.8 Hz), 7.98(1H, d, J=8.8 Hz), 8.13(1H, d, J=2.0 Hz), 8.74(1H, d, J=2.4 Hz), 8.82(1H, d, J=2.0 Hz), 11.16(1H, s).

Example 46
N-(8-Bromoquinolin-3-yl)-4-(2-methylsulfonylethyl)benzenesulfonamide The title compound (55 mg) was obtained by the procedure of Example 1, except using 30 mg (0.13 mmol) of 3-amino-8-bromoquinoline (Preparation Example 5) and 57 mg (0.20 mmol) of 4-(2-methylsulfonylethyl)benzenesulfonyl chloride.

$^1$H-NMR(DMSO-d$_6$) δ (ppm): 2.92(3H, s), 3.00–3.05 (2H, m), 3.37–3.44(2H, m), 7.46(1H, t, J=7.6 Hz), 7.48(2H, d, J=8.0 Hz), 7.80(2H, d, J=8.0 Hz), 7.96(1H, d, J=7.6 Hz), 7.99(1H, d, J=7.6 Hz), 8.04(1H, d, J=2.4 Hz), 8.71(1H, d, J2.4 Hz), 11.02(1H, s).

Example 47
N-(8-Bromoquinolin-3-yl)-4-oxa-7-thiochromansulfonamide

The title compound (99 mg) was obtained by the procedure of Example 1, except using 51 mg (0.23 mmol) of 3-amino-8-bromoquinoline (Preparation Example 5) and 86 mg (0.34 mmol) of 7-chlorosulfonyl-4-oxa-benzothiochroman.

$^1$H-NMR(DMSO-d$_6$) δ (ppm): 3.18(2H, t, J=8.4 Hz), 4.39(2H, t, J=8.4 Hz), 6.92(1H, d, J=8.8 Hz), 7.42(1H, dd, J=2.4, 8.8 Hz), 7.46(1H, t, J=7.6 Hz), 7.59(1H, d, J=2.4 Hz), 7.99(1H, d, J=7.6 Hz), 8.02(1H, d, J=7.6 Hz), 8.05(1H, br), 8.71(1H, d, J=2.4 Hz), 10.92(1H, s).

Example 48
N-(8-Bromoquinolin-3-yl)-4-(2-acetamideethyl)benzenesulfonamide

The title compound (56 mg) was obtained by the procedure of Example 1, except using 30 mg (0.13 mmol) of 3-amino-8-bromoquinoline (Preparation Example 5) and 201 mg (0.77 mmol) of N-(4-chlorosulfonylphenethyl)acetamide.

$^1$H-NMR(DMSO-d$_6$) δ (ppm): 2.71(2H, t, J=7.2 Hz), 3.25–3.20(2H, m), 7.37(2H, d, J=8.4 Hz), 7.46(1H, t, J=8.0 Hz), 7.78(2H, d, J=8.4 Hz), 7.86(1H, br), 7.97(1H, d, J=8.0 Hz), 8.00(1H, d, J=8.0 Hz), 8.04(1H, d, J=2.8 Hz), 8.72(1H, d, J=2.8 Hz), 10.99(1H, s).

Example 49
N-(8-Bromoquinolin-3-yl)-1,2,3,4-tetrahydro-N-acetyl-7-isoquinolinesulfonamide White crystals (180 mg) were obtained in the same manner as in Example 1, except using 145 mg (0.65 mmol) of 3-amino-8-bromoquinoline (Preparation Example 5) and 277 mg (0.85 mmol) of 1,2,3,4-tetrahydro-2-(trifluoroacetyl)isoquinoline-7-sulfonyl chloride. To the crystals were added ethanol (20 ml) and 1 N sodium hydroxide aqueous solution (0.5 ml), followed by stirring at room temperature for 30 minutes. To the reaction mixture was added 1 N hydrochloric acid (0.4 ml), followed by extracting with ethyl acetate. The organic layer was washed with brine, dried over magnesium sulfate and concentrated. To the resulting residue were added pyridine (0.5 ml) and acetic anhydride (0.014 ml), followed by stirring at room temperature for 1 hour. Brine was added thereto, and the mixture was extracted with ethyl acetate. The organic layer was dried over magnesium sulfate and concentrated. The residue was purified by silica gel chromatography, to give 113 mg of the title compound.

$^1$H-NMR(DMSO-$d_6$) δ (ppm): 1.19–1.28(2H, m), 2.05 (3H, s), 2.97(1H, t, J=6.4 Hz), 3.03(1H, t, J=6.4 Hz), 3.75(1H, t, J=6.4 Hz), 4.73(1H, s), 7.37(1H, t, J=8.8 Hz), 7.53–7.58(1H, m), 7.75–7.87(2H, m), 7.91(1H, d, J=8.0 Hz), 8.19–8.27(2H, m), 8.76–8.78(1H, m).

Example 50
N-(8-Bromoquinolin-3-yl) -1,1-dioxide-6-yl -sulfonamide

White crystals were obtained in the same manner as in Example 1, except using 71 mg (0.32 mmol) of 3-amino-8-bromoquinoline (Preparation Example 5) and 119 mg (0.48 mmol) of 6-chlorosulfonylbenzothiochroman. To the crystals were added chloroform (10 ml) and m-chloroperbenzoic acid (145 mg) under ice-cooling, followed by stirring at room temperature for 1 hour. An aqueous saturated sodium thiosulfate was added thereto, and the mixture was extracted with ethyl acetate. The organic layer was washed with brine, dried over magnesium sulfate and concentrated. The residue was purified by silica gel chromatography, to give 113 mg of the title compound.

$^1$H-NMR(DMSO-$d_6$) δ (ppm): 2.26–2.29(2H, m), 3.05 (2H, t, J=6.0 Hz), 3.53–3.56(2H, m), 7.48(1H, t, J=7.6 Hz), 7.86–7.90(2H, m), 7.96–8.04(3H, m), 8.10(1H, d, J=2.4 Hz), 8.75(1H, d, J=2.4 Hz), 11.24(1H, s).

Example 51
N-(8-Bromoquinolin-3-yl)-4-(3-methylsulfonylpropyl)benzenesulfonamide The title compound (62 mg) was obtained by the procedure of Example 1, except using 33 mg (0.14 mmol) of 3-amino-8-bromoquinoline (Preparation Example 5) and 66 mg (0.22 mmol) of 4-(3-methylsulfonylpropyl)benzenesulfonyl chloride.

$^1$H-NMR(DMSO-$d_6$) δ (ppm): 1.90–1.98(2H, m), 2.72 (2H, t, J=8.0 Hz), 2.93(3H, s), 3.06(2H, t, J=8.0 Hz), 7.42(2H, d, J=8.0 Hz), 7.46(1H, d, J=7.6 Hz), 7.97(2H, d, J=7.6 Hz), 8.00(1H, d, J=7.6 Hz), 8.05(1H, d, J=2.4 Hz), 8.72(1H, d, J=2.4 Hz), 11.01(1H, s).

Example 52
N-(8-Bromoquinolin-3-yl)-4-fluorobenzenesulfonamide

The title compound (50 mg) was obtained by the procedure of Example 1, except using 33 mg (0.14 mmol) of 3-amino-8-bromoquinoline (Preparation Example 5) and 39 mg (0.20 mmol) of 4-fluorobenzenesulfonyl chloride.

$^1$H-NMR(DMSO-$d_6$) δ (ppm): 7.40(1H, t, J=8.8 Hz), 7.47(1H, t, J=7.6 Hz), 7.89–7.93(2H, m), 9.78(1H, dd, J=0.9, 7.6 Hz), 8.01(1H, dd, J=0.9, 7.6 Hz), 8.06(1H, d, J=2.4 Hz), 8.71(1H, d, J=2.4 Hz), 11.06(1H, s).

Example 53
N-(8-Bromoquinolin-3-yl)-4-methoxy-2-pyridazinesulfonamide

Under ice-cooling, chlorine gas was blown into a solution of 2-benzylthio-5-methoxypyridazine (0.86 g, 3.7 mmol, Preparation Example 14) in concentrated hydrochloric acid (8 ml), followed by stirring for 1 hour. Then, to the reaction mixture was added ice water, followed by extracting with ethyl acetate. The organic layer was successively washed with water and brine, dried over magnesium sulfate and concentrated, to give the residue 700 mg (2.1 mmol). The title compound (93 mg) was obtained by the procedure of Example 1, except using 180 mg (0.54 mmol) of the above-obtained residue and 60 mg (0.27 mmol) of 3-amino-8-bromoquinoline (Preparation Example 5).

$^1$H-NMR(DMSO-$d_6$) δ (ppm): 4.07(3H, s), 7.44(1H, d, J=9.2 Hz), 7.47(1H, t, J=7.6 Hz), 7.96(1H, t, J=7.6 Hz), 8.02(1H, t, J=7.6 Hz), 8.13(1H, d, J=2.4 Hz), 8.17(1H, d, J=9.2 Hz), 8.82(1H, d, J=2.4 Hz), 11.54(1H, s).

Example 54
N-(8-Bromoquinolin-3-yl)-benzenesulfonamide

The title compound (49 mg) was obtained by the procedure of Example 1, except using 30 mg (0.13 mmol) of 3-amino-8-bromoquinoline (Preparation Example 5) and 35 mg (0.20 mmol) of benzenesulfonyl chloride.

$^1$H-NMR(DMSO-$d_6$) δ (ppm): 7.45(1H, d, J=7.6 Hz), 7.53–7.63(3H, m), 7.84–7.86(2H, m), 7.96(1H, dd, J=1.2, 7.6 Hz), 7.99(1H, dd, J=1.2, 7.6 Hz), 8.04(1H, d, J=2.8 Hz), 8.71(1H, d, J=2.8 Hz), 11.02(1H, s).

Example 55
N-(8-Bromoquinolin-3-yl)-4-carboxamide-2-pyridinesulfonamide

Under ice-cooling, chlorine gas was blown into a solution of 2-benzylthio-4-carboxamidopyridine (1.1 g, 4.3 mmol, Preparation Example 15) in concentrated hydrochloric acid (16 ml), followed by stirring for 1 hour. Then, to the reaction mixture was added ice water, followed by extracting with ethyl acetate. The organic layer was successively washed with water and brine, dried over magnesium sulfate and concentrated. The title compound (37 mg) was obtained by the procedure of Example 1, except using 140 mg (0.40 mmol) of the above-obtained residue and 45 mg (0.20 mmol) of 3-amino-8-bromoquinoline.

$^1$H-NMR(DMSO-$d_6$) δ (ppm): 7.46(1H, d, J=8.0 Hz), 7.94–7.96(2H, m), 8.00–8.02(2H, m), 8.12(1H, d, J=2.4 Hz), 8.44(1H, br), 8.49(1H, br), 8.83–8.85(2H, m), 11.35(1H, s).

Example 56
N-(8-Bromoquinolin-3-yl)-3-methoxybenzenesulfonamide

The title compound (70 mg) was obtained by the procedure of Example 1 except using 40 mg (0.18 mmol) of 3-amino-8-bromoquinoline (Preparation Example 5) and 56 mg (0.27 mmol) of 3-methoxybenzenesulfonyl chloride.

$^1$H-NMR(DMSO-$d_6$) δ (ppm): 3.76(3H, s), 7.17(1H, dd, J=2.8, 8.0 Hz), 7.34–7.40(2H, m), 7.45(1H, t, J=7.6 Hz), 7.46(1H, t, J=7.6 Hz), 7.99(2H, t, J=7.6 Hz), 8.07(1H, d, J=2.4 Hz), 8.72(2H, m), 11.35(1H, d, J=2.4 Hz)

Example 57
N-(8-Bromoquinolin-3-yl)-3-hydroxybenzenesulfonamide

The title compound (73 mg) was obtained by the procedure of Example 1, except using 45 mg (0.20 mmol) of 3-amino-8-bromoquinoline (Preparation Example 5) and 117 mg (0.61 mmol) of 3-hydroxybenzenesulfonyl chloride.

¹H-NMR(DMSO-d₆) δ (ppm): 6.97(1H, d, J=8.0 Hz), 7.18(1H, br), 7.25(1H, d, J=8.0 Hz), 7.34(1H, t, J=8.0 Hz), 7.47(1H, t, J=8.0 Hz), 7.97(1H, d, J=8.0 Hz), 8.01(1H, d, J=8.0 Hz), 8.04(1H, d, J=2.4 Hz), 8.73(1H, d, J=2.4 Hz), 10.15(1H, s), 10.96(1H, s).

Example 58
N-(4-Bromoisoquinolin-7-yl)-4-chlorobenzenesulfonamide

In 1.5 ml of pyridine was dissolved 20 mg (0.09 mmol) of 7-amino-4-bromoisoquinoline (Preparation Example 20), 23 mg of 4-chlorobenzenesulfonyl chloride was added thereto, followed by stirring at room temperature overnight. To the reaction mixture was added water, followed by extracting with ethyl acetate. The extract was dried over magnesium sulfate and concentrated. Then, the resulting residue was purified by silica gel thin layer chromatography, to give 13 mg of the title compound. Melting point: gradually decomposed from 229 degrees.

¹H-NMR(DMSO-d₆) δ (ppm): 7.59–7.61(2H, m), 7.66 (1H, dd, J=2 Hz, 9.2 Hz), 7.82–7.84(3H, m), 7.99(1H, d, J=9.2 Hz), 8.60(1H, s).

Example 59
N-(4-Bromoisoquinolin-7-yl)-6-chloro-3-pyridinesulfonamide

The title compound was obtained from 7-amino-4-bromo isoquinoline (Preparation Example 20) and 6-chloro-3-pyridinesulfonyl chloride in the same manner as in Example 58.

¹H-NMR(DMSO-d₆) δ (ppm): 7.66(1H, dd, J=2.4 Hz, 9.2 Hz), 7.70(1H, d, J=8.4 Hz), 7.89(1H, d, J=2.4 Hz), 8.02(1H, d, J=9.2 Hz), 8.20(1H, dd, J=2.4 Hz, 8.4 Hz), 8.64(1H, s), 8.84(1H, d, J=2.4 Hz), 9.26(1H, s).

Example 60
2-(4-(Chlorobenzenesulfonylamino)-1,6-naphthylidine

In dichloromethane (6.0 ml) was dissolved 200 mg of 2-amino-1,6-naphthyridine (Preparation Example 25), and triethylamine (0.20 ml) and 4-chlorobenzenesulfonyl chloride (0.31 g) were added thereto, followed by stirring at 40° C. for 1.5 hours. An aqueous saturated sodium bicarbonate was added thereto, followed by extracting with ethyl acetate. The extract was washed with brine, dried over anhydrous magnesium sulfate and the solvent was evaporated. The residue was purified by silica gel column, to give the title compound (84 mg, 21.44%) as pale yellow crystals.

¹H-NMR(CDCl₃) δ (ppm): 7.10(1H, d, J=9.2 Hz), 7.37 (1H, d, J=5.4 Hz), 7.46(2H, d, J=8.8 Hz), 7.93(2H, d, J=8.8 Hz), 8.94(1H, d, J=9.2 Hz), 8.66(1H, d, J=5.4 Hz), 8.92(1H, brs).

Example 61
1-Chloro-6-(4-cyanobenzenesulfonylamino)isoquinoline

The title compound was obtained by the procedure of Example 1, except using 6-amino-1-chloroisoquinoline (Preparation Example 23) and 4-cyanobenzenesulfonyl chloride.

¹H-NMR(DMSO-d₆) δ (ppm): 7.52(1H, dd, J=2.0, 8.8 Hz), 7.68(1H, d, J=2.0 Hz), 7.79(1H, d, J=5.6 Hz), 8.03(4H, m), 8.18(1H, d, J=5.6 Hz), 8.21(1H, d, J=8.8 Hz), 11.36(1H, s).

Example 62
1-Chloro-6-(4-chlorobenzenesulfonylamino)isoquinoline

The title compound was obtained by the procedure of Example 1, except using 6-amino-1-chloroisoquinoline (Preparation Example 23) and 4-chlorobenzenesulfonyl chloride.

¹H-NMR(CDCl₃) δ (ppm): 7.33(1H, brs), 7.39(1H, dd, J=2.0, 8.8 Hz), 7.44(2H, d, J=8.8 Hz), 7.50(1H, d, J=5.6 Hz), 7.58(1H, d, J=2.0 Hz), 7.81(2H, d, J=8.8 Hz), 8.24(1H, d, J=5.6 Hz), 8.25(1H, d, J=8.8 Hz).
FAB-MS: 353.

Example 63
1-Chloro-6-(4-(pyrrolidin-1-ylsulfonyl)benzenesulfonylamino)isoquinoline The title compound was obtained by the procedure of Example 1, except using 6-amino-1-chloroisoquinoline (Preparation Example 23) and 4-(pyrrolidin-1-ylsulfonyl)benzenesulfonyl chloride.

¹H-NMR(CDCl₃) δ (ppm): 1.71(4H, m), 3.20(4H, t, J=7.0 Hz), 7.46(1H, d, J=5.4 Hz), 7.49(1H, dd, J=2.0, 9.2 Hz), 7.61(1H, d, J=2.0 Hz), 7.87(2H, d, J=8.8 Hz), 8.02(2H, d, J=8.8 Hz), 8.19(1H, d, J=9.2 Hz), 8.20(1H, d, J=5.4 Hz), 9.72(1H, s).

Example 64
1-Chloro-6-(4-(N-ethylsulfamoyl)benzenesulfonylamino)isoquinoline

The title compound was obtained by the procedure of Example 1, except using 6-amino-1-chloroisoquinoline (Preparation Example 23) and 4-(N-ethylsulfamoyl)benzenesulfonyl chloride.

¹H-NMR(DMSO-d₆) δ (ppm): 0.81(3H, t, J=7.2 Hz), 2.73(2H, m), 7.53(1H, d, J=9.2 Hz), 7.67(1H, s), 7.75(1H, d, J=6.0 Hz), 7.78(1H, d, J=6.0 Hz), 7.92(2H, d, J=8.0 Hz).

Example 65
1-Methoxy-6-(pyridin-3-ylsulfonylamino)isoquinoline

The title compound was obtained by the procedure of Example 1, except using 6-amino-1-methoxyisoquinoline (Preparation Example 43) and 3-pyridinesulfonyl chloride.

¹H-NMR(DMSO-d₆) δ (ppm): 4.09(3H, s), 7.09(1H, d, J=6.0 Hz), 7.25(1H, dd, J=2.0, 8.8 Hz), 7.37(1H, d, J=8.0, 8.8 Hz), 7.48(1H, d, J=2.0 Hz), 7.96(1H, d, J=6.0 Hz), 8.07(1H, ddd, J=1.6, 2.0, 8.0 Hz), 8.14(1H, d, J=8.8 Hz), 8.74(1H, dd, J=1.6, 8.8 Hz), 9.08(1H, d, J=2.0 Hz).
ESI-MS: 316.0.

Example 66
6-(4-Cyanobenzenesulfonylamino)-1-methoxyisoquinoline

The title compound was obtained by the procedure of Example 1, except using 6-amino-1-methoxyisoquinoline (Preparation Example 43) and 4-cyanobenzenesulfonyl chloride.

¹H-NMR(DMSO-d₆) δ (ppm): 3.97(3H, s), 7.25(1H, d, J=5.6 Hz), 7.32(1H, d, J=8.8 Hz), 7.51(1H, s), 7.90(1H, d, J=5.6 Hz), 7.97(2H, d, J=7.6 Hz), 8.01(2H, d, J=7.6 Hz), 8.03(1H, d, J=8.8 Hz).

Example 67
6-(4-Carbamoylbenzenesulfonylamino)-1-methoxyisoquionline

The title compound was obtained according to the procedure described in Synthesis, 949 (1989), except using 6-(4-cyanobenzenesulfonylamino)-1-methoxyisoquinoline (Example 66).

¹H-NMR(DMSO-d₆) δ (ppm): 3.96(3H, s), 7.24(1H, d, J=6.4 Hz), 7.33(1H, d, J=9.2 Hz), 7.51(1H, s), 7.55(1H, brs), 7.88(1H, d, J=6.4 Hz), 7.89(2H, d, J=8.0 Hz), 7.93(2H, d, J=8.0 Hz), 8.01(1H, d, J=9.2 Hz), 8.06(1H, brs), 10.95(1H, s).
FAB-MS: 358.

Example 68
6-(4-(N-Ethylsufamoyl)benzenesulfonylamino)-1-methoxyisoquinoline The title compound was obtained by the procedure of Example 1, except using 6-amino-1-methoxyisoquinoline (Preparation Example 43) and 4-(N-ethylsulfamoyl)benzenesulfonyl chloride.

$^1$H-NMR(DMSO-d$_6$) δ (ppm): 0.81(3H, t, J=6.8 Hz), 2.71(2H, m), 3.96(3H, s), 7.23(1H, d, J=6.4 Hz), 7.32(1H, d, J=8.8 Hz), 7.48(1H, s), 7.73(1H, brs), 7.89(2H, d, J=8.0 Hz), 7.90(1H, d, J=6.4 Hz), 8.01(3H, m), 11.03(1H, brs).

ESI MS: 422.0.

Example 69
6-(2-Aminopyridin-5-ylsulfonylamino)-1-methoxyisoquinoline

The title compound was obtained by the procedure of Example 1, except using 6-amino-1-methoxyisoquinoline (Preparation Example 43) and 6-amino-3-pyridinesulfonyl chloride.

$^1$H-NMR(DMSO-d$_6$) δ (ppm): 3.96(3H, s), 6.39(1H, d, J=8.8 Hz), 6.89(2H, s), 7.25(1H, d, J=4.2 Hz), 7.32(1H, d, J=9.2 Hz), 7.47(1H, s), 7.64(1H, d, J=9.2 Hz), 7.89(1H, d, J=4.2 Hz), 8.01(1H, d, J=8.8 Hz), 8.31(1H, s), 10.95(1H, s).

ESI MS: 331.0.

Example 70
1-Methoxy-6-(4-methylbenzenesulfonylamino)isoquinoline

The title compound was obtained by the procedure of Example 1, except using 6-amino-1-methoxyisoquinoline (Preparation Example 43) and 4-toluenesulfonyl chloride.

$^1$H-NMR(DMSO-d$_6$) δ (ppm): 2.28(3H, s), 3.96(3H, s), 7.22(1H, d, J=6.0 Hz), 7.32(3H, m), 7.48(1H, s), 7.71(2H, d, J=8.4 Hz), 7.88(1H, d, J=6.0 Hz), 8.00(1H, d, J=9.2 Hz), 10.79(1H, s).

ESI MS: 329.0.

Example 71
6(4-Acetylaminobenzenesulfonylamino)-1-methoxyisoquinoline

The title compound was obtained by the procedure of Example 1, except using 6-amino-1-methoxyisoquinoline (Preparation Example 43) and 4-acetamidobenzenesulfonyl chloride.

$^1$H-NMR(DMSO-d$_6$) δ (ppm): 2.01(3H, s), 3.96(3H, s), 7.23(1H, d, J=6.0 Hz), 7.32(1H, d, J=9.2 Hz), 7.47(1H, s), 7.67(2H, d, J=8.8 Hz), 7.76(2H, d, J=8.8 Hz), 7.88(1H, d, J=6.0 Hz), 8.00(1H, d, J=9.2 Hz), 10.26(1H, s), 10.75(1H, s).

EST MS: 372.1.

Example 72
6-(4-Methanesulfonylaminobenzenesulfonylamino)-1-methoxyisoquinoline The nitro group of the compound synthesized in the same manner as in Example 1, except using 6-amino-1-methoxyisoquinoline (Preparation Example 43) and 4-nitrobenzenesulfonyl chloride was reduced in the same manner as in Preparation Example 170. The resulting compound was dissolved in pyridine, and under ice-cooling, methanesulfonyl chloride was added thereto, followed by stirring as it was for 4 hours. Brine was added thereto, followed by extracting with ethyl acetate, The extract was washed with brine, dried over anhydrous magnesium sulfate and the solvent was evaporated. Then, the residue was purified by silica gel column, and the resulting crystals were recrystallized from ethanol, to give the title compound.

$^1$H-NMR(DMSO-d$_6$) δ (ppm): 3.06(3H, s), 3.97(3H, s), 7.24(3H, m), 7.33(1H, d, J=9.0 Hz), 7.49(1H, s), 7.79(2H, d, J=8.8 Hz), 7.89(1H, d, J=6.0 Hz), 8.01(1H, d, J=9.0 Hz), 10.39(1H, s), 10.80(1H, s).

ESI MS: 372.1.

Example 73
6-(2-Chloropyridin-5-ylsulfonylamino)-1-methoxyisoquinoline

The title compound was obtained by the procedure of Example 1, except using 6-amino-1-methoxyisoquinoline (Preparation Example 43) and 6-chloro-3-pyridinesulfonyl chloride.

$^1$H-NMR(DMSO-d$_6$) δ (ppm): 3.31(3H, s), 3.99(3H, s), 7.30(1H, d, J=6.0 Hz), 7.34(1H, d, J=8.8 Hz), 7.56(1H, s), 7.71(1H, d, J=8.8 Hz), 7.92(1H, d, J=6.0 Hz), 8.06(1H, d, J=8.8 Hz), 8.19(1H, d, J=8.8 Hz), 11.13(1H, s).

ESI MS: 350.1.

Example 74
1-Methoxy-6-(3-methylbenzenesulfonylamino)isoquinoline

The title compound was obtained by the procedure of Example 1, except using 6-amino-1-methoxyisoquinoline (Preparation Example 43) and 3-toluenesulfonyl chloride.

$^1$H-NMR(DMSO-d$_6$) δ (ppm): 2.31(3H, s), 3.96(3H, s), 7.22(1H, d, J=6.0 Hz), 7.32(1H, dd, J=2.0, 8.8 Hz), 7.39(2H, m), 7.47(1H, d, J=2.0 Hz), 7.62(1H, m), 7.67(1H, s), 7.87(1H, d, J=6.0 Hz), 8.00(1H, d, J=8.8 Hz), 10.84(1H, s).

Example 75
6-Benzylsulfonylamino-1-methoxyisoquinoline

The title compound was obtained by the procedure of Example 1, except using 6-amino-1-methoxyisoquinoline (Preparation Example 43) and benzylsulfonyl chloride.

$^1$H-NMR(CDCl$_3$) δ (ppm): 4.13(3H, s), 4.42(2H, s), 6.69(1H, brs), 7.13(2H, m), 7.22(2H, m), 7.30–7.37(3H, m), 7.50(1H, d, J=2.4 Hz), 7.99(1H, d, J=6.0 Hz), 8.20(1H, d, J=8.8 Hz).

Example 76
6-(3-Cyanobenzenesulfonylamino)-1-methoxyisoquinoline

The title compound was obtained by the procedure of Example 1, except using 6-amino-1-methoxyisoquinoline (Preparation Example 43) and 3-cyanobenzenesulfonyl chloride.

$^1$H-NMR(DMSO-d$_6$) δ (ppm): 3.98(3H, s), 7.28(1H, d, J=6.0 Hz), 7.34(1H, dd, J=2.0, 8.8 Hz), 7.53(1H, d, J=2.0 Hz), 7.75(1H, dd, J=8.0, 8.0 Hz), 7.91(1H, d, J=6.0 Hz), 8.04(1H, d, J=8.8 Hz), 8.09(2H, m), 9.29(1H, m), 11.05(1H, s).

Example 77
1-Methoxy-6-(4-thiazol-2-ylbenzenesulfonylamino)isoquinoline

The compound (40 mg) obtained by the procedure of Example 1, except using 6-amino-1-methoxyisoquinoline (Preparation Example 43) and 4-iodobenzenesulfonyl chloride, 2-tri-n-butylstannylthiazole (136 mg), tetrakis(triphenylphosphine)palladium(0) (11 mg) were heated under reflux in toluene in nitrogen atmosphere for 1 hour. The solvent was evaporated and the residue was purified by silica gel column. The resulting crystals were recrystallized from methanol, to give the title compound (20 mg).

$^1$H-NMR(CDCl$_3$) δ (ppm): 4.08(3H, s), 6.94(1H, brs), 7.09(1H, d, J=6.0 Hz), 7.23(1H, dd, J=2.0, 8.8 Hz), 7.41(1H, d, J=3.6 Hz), 7.45(1H, d, J=2.0 Hz), 7.89(2H, d, J=8.4 Hz), 7.90(1H, d, J=8.6 Hz), 7.95(1H, d, J=6.0 Hz), 7 82(2H, d, J=8.4 Hz), 8.13(1H, d, J=8.8 Hz).

Example 78
6-(4-Chlorobenzenesulfonylamino)-1-methoxyisoquinoline

The title compound was obtained by the procedure of Example 1, except using 6-amino-1-methoxyisoquinoline (Preparation Example 43) and 4-chlorobenzenesulfonyl chloride.

$^1$H-NMR(DMSO-$d_6$) δ (ppm): 4.00(3H, s), 7.27(1H, d, J=5.6 Hz), 7.45(1H, dd, J=2.0, 8.8 Hz), 7.53(1H, d, J=2.0 Hz), 7.63(2H, d, J=8.8 Hz), 7.85(1H, d, J=8.8 Hz), 7.92(1H, d, J=5.6 Hz), 8.06, (1H, J=8.8 Hz), 10.97(1H, s).

Example 79
6-(4-Chlorobenzenesulfonylamino)-1-methylisoquinoline

The title compound was obtained by the procedure of Example 1, except using 6-amino-1-methylisoquinoline (Preparation Example 33) and 4-chlorobenzenesulfonyl chloride.

$^1$H-NMR(DMSO-$d_6$) δ (ppm): 2.76(3H, s), 7.56(1H, d, J=6.0 Hz), 7.52(2H, m), 7.60(2H, d, J=8.8 Hz), 7.82(2H, d, J=8.8 Hz), 8.08(1H, d, J=9.2 Hz), 8.20(1H, d, J=6.0 Hz).
ESI-MS: 333.0.

Example 80
6-(4-Chlorobenzenesulfonylamino)-1-ethylisoquinoline

The title compound was obtained by the procedure of Example 1, except using 6-amino-1-ethylisoquinoline (Preparation Example 48) and 4-chlorobenzenesulfonyl chloride.

$^1$H-NMR(DMSO-$d_6$) δ (ppm): 1.39(3H, t, J=7.6 Hz), 3.25(2H, q, J=7.6 Hz), 7.35(1H, dd, J=2.4, 9.2 Hz), 7.38(1H, d, J=5.6 Hz), 7.41(2H, d, J=8.8 Hz), 7.53(1H, d, J=2.4 Hz), 7.81(2H, d, J=8.8 Hz), 8.05(1H, d, J=9.2 Hz), 8.37(1H, d, J=5.6 Hz). ESI-MS: 347.0.

Example 81
6-(4-(Chlorobenzenesulfonylamino)-4-methylisoquinoline

The title compound was obtained by the procedure of Example 1, except using 6-amino-4-ethylisoquinoline (Preparation Example 66) and 4-chlorobenzenesulfonyl chloride.

$^1$H-NMR(DMSO-$d_6$) δ (ppm): 1.18(3H, t, J=7.2 Hz), 2.85(2H, q, J=7.2 Hz), 7.38(1H, d, J=8.8 Hz), 7.60(1H, s), 7.62(2H, d, J=8.0 Hz), 7.82(2H, d, J=8.0 Hz), 8.00(1H, d, J=8.8 Hz), 8.26(1H, s), 8.99(1H, s).

Example 82
6-(4-Chlorobenzenesulfonylamino)-4-methylisoquinoline

The title compound was obtained by the procedure of Example 1, except using 6-amino-4-methylisoquinoline (Preparation Example 58) and 4-chlorobenzenesulfonyl chloride.

$^1$H-NMR(DMSO-$d_6$) δ (ppm): 2.43(3H, s), 7.41(1H, d, J=8.8 Hz), 7.56(1H, s), 7.62(2H, d, J=8.8 Hz), 7.85(2H, d, J=8.8 Hz), 7.99(1H, d, J=8.8 Hz), 8.26(1H, s), 8.98(1H, s), 11.09(1H, brs).

Example 83
6-(4-Chlorobenzenesulfonylamino)-3-methylisoquinoline

The title compound was obtained by the procedure of Example 1, except using 6-amino-3-methylisoquinoline (Preparation Example 76) and 4-chlorobenzenesulfonyl chloride.

$^1$H-NMR(DMSO-$d_6$) δ (ppm): 2.53(3H, s), 7.30(1H, d, J=8.8 Hz), 7.45(1H, s), 7.50(1H, s), 7.62(2H, d, J=8.4 Hz), 7.84(2H, d, J=8.4 Hz), 7.93(1H, d, J=8.8 Hz), 9.03(1H, s).

Example 84
6-(4-Chlorobenzenesulfonylamino)-1-cyanoisoquinoline

The compound obtained by the procedure of Example 1, except using 6-aminoisoquinoline (0.5 g, Synthesis, 733 (1975) and 4-chlorobenzenesulfonyl chloride (0.88 g) was dissolved in chloroform (150 ml). Under ice-cooling, m-chloroperbenzoic acid (0.9 g) was added thereto, followed by stirring at room temperature overnight. The solvent was evaporated, and the resulting crystals were washed with diethyl ether, collected by filtration and dried, to give 6-(4-chlorobenzenesulfonylamino)isoquinoline-N-oxide (1.072 g). In acetonitrile (1.5 ml) was dissolved 50 mg of the obtained compound. To the mixture were added trimethyl cyanide (0.08 ml) and triethylamine (0.04 ml), followed by heating under reflux for 3.5 hours. After evaporating the solvent, the residue was purified by silica gel column, to give the title compound (23 mg, 64%) as yellow crystals.

$^1$H-NMR(DMSO-$d_6$) δ (ppm): 7.66(2H, d, J=8.8 Hz), 7.67(1H, dd, J=2.0, 9.2 Hz), 7.80(1H, d, J=2.0 Hz), 7.93(2H, d, J=8.8 Hz), 8.17(1H, d, J=9.2 Hz), 8.18(1H, d, J=5.6 Hz), 8.59(1H, d, J=5.6 Hz).
ESI-MS: 344.1

Example 85
1-Carbamoyl-6-(4-chlorobenzenesulfonylamino)isoquinoline

The crystals obtained by the procedure described in Synthesis, 949 (1989), except using 6-(4-chlorobenzenesulfonylamino)-1-cyanoisoquinoline (30 mg, Example 83) was washed with diethyl ether, to give the title compound (26 mg, 82%) as colorless crystals.

$^1$H-NMR(CDCl$_3$) δ (ppm): 6.25(1H, brs), 7.35(2H, d, J=8.8 Hz), 7.43(1H, dd, J=2.0, 9.2 Hz), 7.62(1H, d, J=2.0 Hz), 7.66 1H, d, J=6.8 Hz), 7.81(2H, d, J=8.8 Hz), 8.04(1H, brs), 8.37(1H, brs), 9.32(1H, d, J=9.2 Hz), 9.76(1H, brs).

Example 86
6-(4-Chlorobenzenesulfonylamino)-1-methylaminoisoquinoline

A mixture of 1-chloro-6-(4-chlorobenzenesulfonylamino)isoquinoline (50 mg, Example 61) and 40% methylamine methanol solution (5.0 ml) was heated in a sealed tube at 130° C. for 18 hours. After standing to cool, an aqueous saturated sodium bicarbonate was added thereto and the mixture was extracted with ethyl acetate. The extract was washed with brine, dried over anhydrous magnesium sulfate and the solvent was evaporated. The residue was purified by silica gel column, to give the title compound (28 mg, 52%) as a pale yellow solid.

$^1$H-NMR(CDCl$_3$) δ (ppm): 3.14(3H, s), 5.22(1H, brs), 6.89(1H, d, J=6.0 Hz), 7.19(1H, dd, J=2.4 Hz, 9.2 Hz), 7.31(1H, d, J=2.4 Hz), 7.40(2H, d, J=8.8 Hz), 7.64(1H, d, J=9.2 Hz), 7.73(2H, d, J=8.8 Hz), 7.98(1H, d, J=6.0 Hz).

Example 87
1-Amino-6-(4-chlorobenzenesulfonylamino)isoquinoline

The Crystals obtained by the procedure described in YAKUGAKU ZASSHI (Journal of the Pharmaceutical Society of Japan), 84, 35 (1964), except using 6-(4-chlorobenzenesulfonylamino)isoquinoline-N-oxide (50 mg, intermediate in Example 83) was washed with diethyl ether and dried, to give the title compound (2 mg) as light brown crystals.

$^1$H-NMR(DMSO-$d_6$) δ (ppm): 7.76(1H, d, J=6.0 Hz), 6.93(2H, brs), 7.15(1H, dd, J=2.0, 8.8 Hz), 7.27(1H, d, J=2.0 Hz), 7.59(2H, d, J=8.8 Hz), 7.63(1H, d, J=6.0 Hz), 7.80(2H, d, J=8.8 Hz), 9.05(1H, d, J=6.0 Hz).
ESI-MS: 334.1.

Example 88
6-(4-Chlorobenzenesulfonylamino)-1-dimethylaminoisoquinoline

In dimethyl sulfoxide (1 ml) was dissolved 60 mg of 1-chloro-6-(4-chlorobenzenesulfonylamino)isoquinoline (Example 61). To the mixture was added 50% dimethylamine methanol solution (0.04 ml), followed by heating under stirring at 80° C. for 10 hours. After standing to cool, water was added thereto and the mixture was extracted with ethyl acetate. The extract was washed with brine, dried over anhydrous magnesium sulfate and the solvent was evaporated. The residue was purified by preparative TLC and solidified from isopropyl ether, to give the title compound (17 mg).

$^1$H-NMR(DMSO-d$_6$) δ (ppm): 2.96(6H, s), 7.12(1H, d, J=6.0 Hz), 7.27(1H, dd, J=2,0, 9.2 Hz), 7.45(1H, d, J=2.0 Hz), 7.64(2H, d, J=8.8 Hz), 7.85(2H, d, J=8.8 Hz), 7.93(1H, d, J=6.0 Hz), 8.01(1H, d, J=9.2 Hz), 10.91(1H, brs).

Example 89
6-(4-Chlorobenzenesulfonylamino)-1-hydroxyisoquinoline

In acetic anhydride (0.75 ml) was dissolved 50 mg of 6-(4-chlorobenzenesulfonylamino)isoquinoline-N-oxide (intermediate in Example 83), followed by heated under stirring at 80° C. for 16 hours and then for 2 hours. After standing to cool, an aqueous saturated sodium bicarbonate was added thereto and the mixture was extracted with ethyl acetate. The extract was washed with brine, dried over anhydrous magnesium sulfate and the solvent was evaporated. The residue was dissolved in ethanol (2.0 ml) and water (0.5 ml), followed by heating under reflux for 0.5 hour. After evaporating the solvent, the residue was purified by silica gel column, to give the title compound (20 mg) as a pale red solid.

$^1$H-NMR(CDCl$_3$) δ (ppm): 6.58(1H, d, J=7.2 Hz), 7.22 (1H, d, J=7.2 Hz), 7.31(1H, dd, J=2.0, 8.4 Hz), 7.54(1H, d, J=2.0 Hz), 7.56 (2H, d, J=8.8 Hz), 8.01(2H, d, J=8.8 Hz), 8.53(1H, d, J=8.4 Hz), 10.36(1H, brs).

ESI-MS: 335.1.

Example 90
6-(4-Chlorobenzenesulfonylamino)-1-ethoxyisoquinoline

In dimethyl sulfoxide (1 ml) was dissolved 57 mg of 1-chloro-6-(4-chlorobenzenesulfonylamino)isoquinoline (Example 61). To the mixture were added ethanol (0.1 ml) and 60% sodium hydride (14 mg), followed by heating under stirring at 80° C. for 9 hours. After standing to cool, water was added thereto and the mixture was extracted with ethyl acetate. The extract was washed with brine, dried over anhydrous magnesium sulfate and the solvent was evaporated. Then, the residue was purified by preparative TLC and solidified from isopropyl ether, to give the title compound (21 mg).

$^1$H-NMR(DMSO-d$_6$) δ (ppm): 1.38(3H, t, J=7.2 Hz), 4.46(2H, q, J=7.2 Hz), 7.24(1H, d, J=6.0 Hz), 7.35(1H, dd, J=2.0, 9.2 Hz), 7.50(1H, d, J=2.0 Hz), 7.63(2H, d, J=8.8 Hz), 7.90(1H, d, J=6.0 Hz), 8.04(1H, d, J=9.2 Hz), 10.94(1H, brs).

Example 91
N-(5-Vinylquinolin-2-yl)-3-pyridinesulfonamide

A solution of 2-amino-5-bromoquinoline (510 mg, Preparation Example 1), vinyltributyltin (0.94 ml), toluene (4 ml), tetrakis(triphenylphosphine)palladium(0) (20 mg) and 2,6-di-t-butyl-p-cresol (about 0.1 mg) was stirred at 120° C. for 4 hours. After cooling to room temperature, water was added thereto and the mixture was extracted with ethyl acetate. The ethyl acetate layer was dried over sodium sulfate and concentrated. Then, the resulting solid was washed with hexane, to give 282 mg of a solid containing a vinyl derivative. The solid was dissolved in 2 ml of pyridine and 412 mg of 3-pyridinesulfonyl chloride was added thereto, followed by stirring at room temperature overnight. Water was added thereto and the mixture was extracted with ethyl acetate. The ethyl acetate layer was dried over sodium sulfate and concentrated. Then, the resulting solid was washed with methanol, to give the title compound (235 mg).

$^1$H-NMR(CDCl$_3$) δ (ppm): 5.59(1H, dd, J=10.8 Hz, 1.5 Hz), 5.82(1H, dd, J=16.9 Hz, 1.5 Hz), 6.95(1H, d, J=10.3 Hz), 7.20(1H, dd, J=10.8 Hz, 16.9 Hz), 7.36(1H, d, J=8.5 Hz), 7.43(1H, m), 7.50(1H, d, J=8.5 Hz), 7.62(1H, t, J=8.5 Hz), 8.24(1H, d, J=10.3 Hz), 8.29(1H, m), 8.74(1H, m), 9.22(1H, m).

Example 92
N-(4-Trifluoromethylcoumarin-7-yl)-4-chlorobenzenesulfonamide

To a solution of 7-amino-4-trifluoromethylcoumarin (200 mg, 0.87 mmol) and 4-dimethylaminopyridine (1 mg) in pyridine (3 ml) was added 4-chlorobenzenesulfonyl chloride (203 mg, 0.96 mmol), followed by stirring at 70 degrees for 50 minutes. To the reaction mixture was added 2 N hydrochloric acid, followed by extracting with ethyl acetate. The organic layer was washed with water and brine, dried over magnesium sulfate and evaporated. The resulting residue was crystallized from ethyl acetate-diisopropyl ether, to give 253 mg of the title compound as a pale yellow solid.

$^1$H-NMR(DMSO-d$_6$) δ (ppm): 6.87(1H, s), 7.12(1H, d, J=2.4 Hz), 7.17(1H, dd, J=2.6, 8.4 Hz), 7.60(1H, d, J=8.4 Hz), 7.67(2H, d, J=6.8 Hz), 7.87(2H, d, J=6.8 Hz), 11.29 (1H, s).

TABLE 2-1

| Ex. No. | Structural Formula |
|---|---|
| 1 | 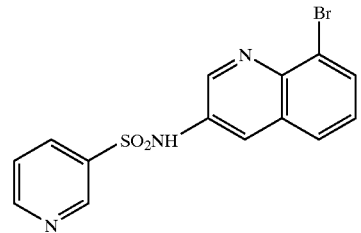 |
| 2 | 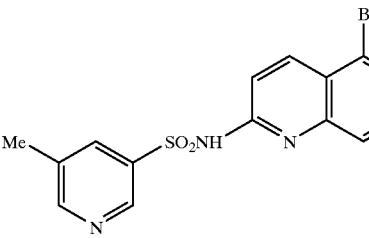 |
| 3 | 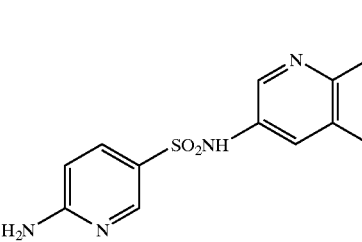 |

TABLE 2-1-continued

| Ex. No. | Structural Formula |
|---|---|
| 4 | 4-NC-C6H4-SO2NH-(8-Br-quinolin-3-yl) |
| 5 | 4-Cl-C6H4-SO2NH-(8-Br-quinolin-3-yl) |
| 6 | 4-(EtHNO2S)-C6H4-SO2NH-(8-Br-quinolin-3-yl) |
| 7 | (5-NC-pyridin-2-yl)-SO2NH-(8-Br-quinolin-3-yl) |
| 8 | (pyridin-3-yl)-SO2NH-(8-CN-quinolin-3-yl) |
| 9 | (4-NC-C6H4)-SO2NH-(8-CN-quinolin-3-yl) |
| 10 | (pyridin-3-yl)-SO2NH-(5-Br-quinolin-2-yl) |
| 11 | (indan-5-yl)-SO2NH-(8-Br-quinolin-3-yl) |
| 12 | (1-Ac-indolin-5-yl)-SO2NH-(8-I-quinolin-3-yl) |
| 13 | (quinolin-3-yl)-SO2NH-(8-Br-quinolin-3-yl) |
| 14 | (1-Ac-1,2,3,4-tetrahydroquinolin-6-yl)-SO2NH-(8-Br-quinolin-3-yl) |

TABLE 2-2

| Ex. No. | Structural Formula |
|---|---|
| 15 | isoquinoline-4-SO₂NH-(8-iodoquinolin-3-yl) |
| 16 | 4-cyanophenyl-SO₂NH-(8-iodoquinolin-3-yl) |
| 17 | pyridin-3-yl-SO₂NH-(8-iodoquinolin-3-yl) |
| 18 | 4-cyanophenyl-SO₂NH-(5-bromoquinolin-2-yl) |
| 19 | (8-bromoquinolin-3-yl)-NH-SO₂-(6-ethylpyridin-3-yl) |
| 20 | (5-chloroquinolin-2-yl)-NH-SO₂-(4-chlorophenyl) |

TABLE 2-2-continued

| Ex. No. | Structural Formula |
|---|---|
| 21 | 8-chloroquinolin-3-yl-NH-SO₂-(6-ethylpyridin-3-yl) |
| 22 | 5-chloroquinolin-2-yl-NH-SO₂-(6-ethylpyridin-3-yl) |
| 23 | 8-chloroquinolin-3-yl-NH-SO₂-phenyl |
| 24 | 5-chloroquinolin-2-yl-NH-SO₂-(4-cyanophenyl) |
| 25 | 5-chloroquinolin-2-yl-NH-SO₂-(4-methylphenyl) |
| 26 | 5-chloroquinolin-2-yl-NH-SO₂-C₆H₄-SO₂NH₂ |
| 27 | 5-bromoquinolin-2-yl-NH-SO₂-C₆H₄-S(=O)₂-NH-ethyl |

TABLE 2-2-continued

| Ex. No. | Structural Formula |
| --- | --- |
| 28 | 8-chloroquinolin-3-yl NHSO₂-(3-cyanophenyl) |

TABLE 2-3

| Ex. No. | Structural Formula |
| --- | --- |
| 29 | 8-chloroquinolin-3-yl NHSO₂-(3-methylphenyl) |
| 30 | 8-chloroquinolin-3-yl NHSO₂-(3-sulfamoylphenyl) |
| 31 | 8-methylquinolin-3-yl NHSO₂-(pyridin-3-yl) |
| 32 | 8-methylquinolin-3-yl NHSO₂-(4-cyanophenyl) |
| 33 | 6-chloro-8-cyanoquinolin-3-yl NHSO₂-(pyridin-3-yl) |
| 34 | 8-chloroquinolin-3-yl NHSO₂-(4-cyanophenyl) |
| 35 | 8-chloroquinolin-3-yl NHSO₂-(4-(N-ethylsulfamoyl)phenyl) |

TABLE 2-3-continued

| Ex. No. | Structural Formula |
|---|---|
| 36 | (3-pyridyl)-SO₂NH-(8-chloroquinolin-3-yl) |
| 37 | 5-(EtNHSO₂)-pyridin-2-yl-SO₂NH-(8-chloroquinolin-3-yl) |
| 38 | 4-NC-C₆H₄-SO₂NH-(8-trifluoromethylquinolin-3-yl) |
| 39 | 4-(EtNHSO₂)-C₆H₄-SO₂NH-(8-trifluoromethylquinolin-3-yl) |
| 40 | (3-pyridyl)-SO₂NH-(8-trifluoromethylquinolin-3-yl) |
| 41 | (5,6,7,8-tetrahydronaphthalen-2-yl)-SO₂NH-(8-chloroquinolin-3-yl) |
| 42 | (2,3-dihydrobenzofuran-5-yl)-SO₂NH-(8-chloroquinolin-3-yl) |
| 43 | 4-NC-C₆H₄-SO₂NH-(8-chloro-4-vinylquinolin-3-yl) |
| 44 | (1-acetyl-2,3-dihydroindol-5-yl)-SO₂NH-(8-trifluoromethylquinolin-3-yl) |

TABLE 2-3-continued

| Ex. No. | Structural Formula |
|---|---|
| 45 | MeS-(6-pyridyl)-SO₂NH-(8-bromoquinolin-3-yl) |
| 46 | MeSO₂CH₂CH₂-(4-phenyl)-SO₂NH-(8-bromoquinolin-3-yl) |
| 47 | 2,3-dihydro-1,4-benzoxathiine-6-SO₂NH-(8-bromoquinolin-3-yl) |
| 48 | AcNHCH₂CH₂-(4-phenyl)-SO₂NH-(8-bromoquinolin-3-yl) |

TABLE 2-4

| Ex. No. | Structural Formula |
|---|---|
| 49 | 2-acetyl-1,2,3,4-tetrahydroisoquinolin-7-SO₂NH-(8-bromoquinolin-3-yl) |
| 50 | 3,4-dihydro-2H-1-benzothiopyran 1,1-dioxide-6-SO₂NH-(8-bromoquinolin-3-yl) |
| 51 | MeSO₂(CH₂)₃-(4-phenyl)-SO₂NH-(8-bromoquinolin-3-yl) |
| 52 | 4-F-C₆H₄-SO₂NH-(8-bromoquinolin-3-yl) |

TABLE 2-4-continued

| Ex. No. | Structural Formula |
|---|---|
| 53 | 6-methoxy-pyridazine-3-sulfonic acid (8-bromoquinolin-3-yl)amide |
| 54 | benzenesulfonic acid (8-bromoquinolin-3-yl)amide |
| 55 | 4-carbamoyl-pyridine-2-sulfonic acid (8-bromoquinolin-3-yl)amide |
| 56 | 3-methoxy-benzenesulfonic acid (8-bromoquinolin-3-yl)amide |
| 57 | 3-hydroxy-benzenesulfonic acid (8-bromoquinolin-3-yl)amide |
| 58 | 4-chloro-benzenesulfonic acid (4-bromoisoquinolin-7-yl)amide |
| 59 | 6-chloro-pyridine-3-sulfonic acid (4-bromoisoquinolin-7-yl)amide |
| 60 | 4-chloro-benzenesulfonic acid (1,6-naphthyridin-2-yl)amide |

TABLE 2-4-continued

| Ex. No. | Structural Formula |
|---|---|
| 61 | 4-cyanophenyl-SO₂NH-(1-chloroisoquinolin-6-yl) |
| 62 | 4-chlorophenyl-SO₂NH-(1-chloroisoquinolin-6-yl) |
| 63 | 4-(pyrrolidin-1-ylsulfonyl)phenyl-SO₂NH-(1-chloroisoquinolin-6-yl) |
| 64 | 4-(ethylaminosulfonyl)phenyl-SO₂NH-(1-chloroisoquinolin-6-yl) |
| 65 | pyridin-3-yl-SO₂NH-(1-methoxyisoquinolin-6-yl) |
| 66 | 4-cyanophenyl-SO₂NH-(1-methoxyisoquinolin-6-yl) |

TABLE 2-5

| Ex. No. | Structural Formula |
|---|---|
| 67 | 4-(H₂NOC)-C₆H₄-SO₂NH-(1-methoxyisoquinolin-6-yl) |
| 68 | 4-(EtNH-SO₂)-C₆H₄-SO₂NH-(1-methoxyisoquinolin-6-yl) |
| 69 | 6-amino-pyridin-3-yl-SO₂NH-(1-methoxyisoquinolin-6-yl) |
| 70 | 4-Me-C₆H₄-SO₂NH-(1-methoxyisoquinolin-6-yl) |
| 71 | 4-(AcNH)-C₆H₄-SO₂NH-(1-methoxyisoquinolin-6-yl) |
| 72 | 4-(MsNH)-C₆H₄-SO₂NH-(1-methoxyisoquinolin-6-yl) |

TABLE 2-5-continued

| Ex. No. | Structural Formula |
| --- | --- |
| 73 | 6-chloropyridine-3-sulfonamide of 1-methoxyisoquinolin-6-amine |
| 74 | 3-methylbenzenesulfonamide of 1-methoxyisoquinolin-6-amine |
| 75 | phenylmethanesulfonamide of 1-methoxyisoquinolin-6-amine |
| 76 | 3-cyanobenzenesulfonamide of 1-methoxyisoquinolin-6-amine |
| 77 | 4-(thiazol-2-yl)benzenesulfonamide of 1-methoxyisoquinolin-6-amine |
| 78 | 4-chlorobenzenesulfonamide of 1-methoxyisoquinolin-6-amine |

TABLE 2-5-continued

| Ex. No. | Structural Formula |
|---|---|
| 79 | 4-Cl-C6H4-SO2NH-(1-methylisoquinolin-6-yl) |
| 80 | 4-Cl-C6H4-SO2NH-(1-ethylisoquinolin-6-yl) |
| 81 | 4-Cl-C6H4-SO2NH-(4-ethylisoquinolin-6-yl) |
| 82 | 4-Cl-C6H4-SO2NH-(4-methylisoquinolin-6-yl) |

TABLE 2-6

| Ex. No. | Structural Formula |
|---|---|
| 83 | 4-Cl-C6H4-SO2NH-(3-methylisoquinolin-6-yl) |
| 84 | 4-Cl-C6H4-SO2NH-(1-cyanoisoquinolin-6-yl) |

TABLE 2-6-continued
| Ex. No. | Structural Formula |
| --- | --- |
| 85 | 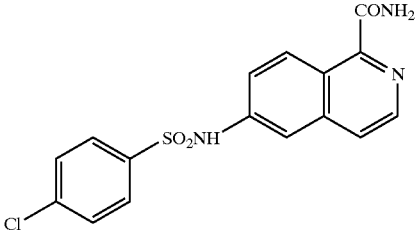 |
| 86 | 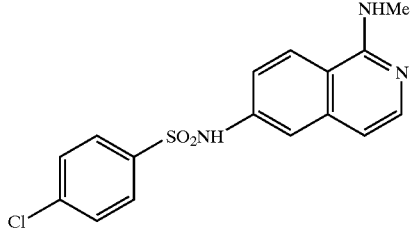 |
| 87 | 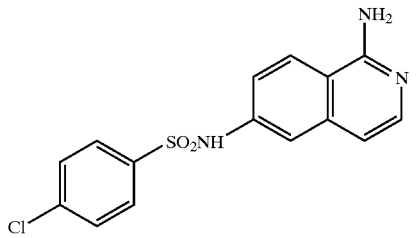 |
| 88 | 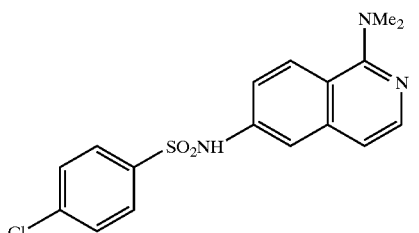 |
| 89 | 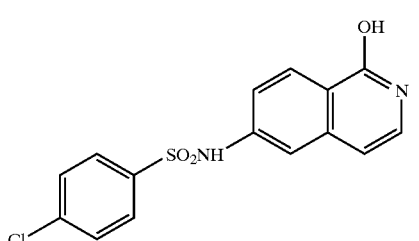 |
| 90 | 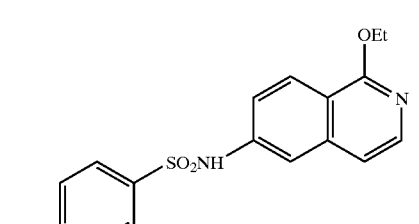 |

TABLE 2-6-continued

| Ex. No. | Structural Formula |
|---|---|
| 91 | |
| 92 | |

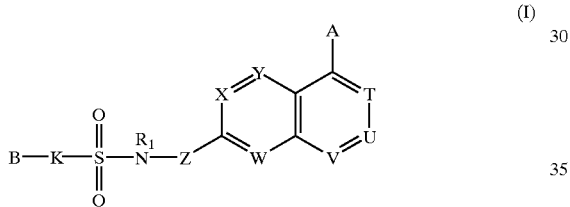

What is claimed is:

1. A compound of formula (I), a pharmacologically acceptable salt or hydrates thereof:

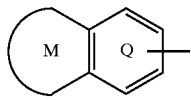

(I)

wherein A in formula (I) is a hydrogen atom, halogen atom, hydroxyl group, C1–C4 alkyl group or alkoxy group which may be substituted with a halogen atom, cyano group, —(CO)kNR$^2$R$^3$ (wherein, R$^2$ and R$^3$ are the same as or different from each other and each means hydrogen atom or a C1–C4 alkyl group which may be substituted with a halogen atom; and k means 0 or 1), C2–C4 alkenyl group or alkynyl group which may have a substituent, or a phenyl group or phenoxy group which may have a substituent selected from the following group A;

B is an aryl group or monocyclic heteroaryl group which may have a substituent selected from the following group A, or (wherein, the ring Q is an aromatic ring which may have one or two nitrogen atoms; the ring M is an unsaturated C5–C12 monocyclic or polycyclic ring which shares a double bond with the ring Q, and the ring may have 1 to 4 hetero atoms selected from nitrogen atom, oxygen atom and sulfur atom; the ring Q and the ring M may share nitrogen atom with each other, and the ring Q and the ring M may each have a substituent selected from the following group A);

K is a single bond or —(CR$^4$R$^5$)m— (wherein, R$^4$ and R$^5$ are the same as or different from each other and each means hydrogen atom or a C1–C4 alkyl group; and m is an integer of 1 or 2);

one of T, U, V, W, X and Y is a nitrogen atom and the rest are =C(D)— (wherein D is a hydrogen atom, halogen atom, hydroxyl group, C1–C4 alkyl group or alkoxy group which may be substituted by a halogen atom, cyano group, —(CO)nNR$^6$R$^7$ (wherein R$^6$ and R$^7$ are the same as or different from each other and each means a hydrogen atom or a C1–C4 alkyl group which may be substituted with a halogen atom; and n means 0 or 1), or a C2–C4 alkenyl group or alkynyl group which may have a substituent);

Z is a single bond or —CO—NH—;

R$_1$ is a hydrogen atom or a C1–C4 alkyl group; and ----- means a single or double bond, Group A is a halogen atom, hydroxyl group, C1–C4 alkyl group or alkoxy group which may be substituted by a halogen atom, cyano group, —R$^8$R$^9$N(NH)p— (wherein R$^8$ and R$^9$ are the same as or different from each other and each means hydrogen atom or a C1–C4 alkyl group which may be substituted with a halogen atom; and p means 0 or 1, and R$^8$ and R$^9$ may be combined with the nitrogen atom to which they bound to form a 5- or 6-membered ring which may further include a nitrogen atom, oxygen atom or sulfur atom and may have a substituent), an aminosulfonyl group which may be substituted with one or two C1–C4 alkyl groups, an optionally substituted C1–C8 acyl group, a C1–C4 alkyl-S(O)s-C1–C4 alkylene group (wherein s means an integer of 0, 1 or 2), a phenylsulfonylamino group which may have a C1–C4 alkyl or a substituent, —(CO)qNR$^{10}$R$^{11}$ (wherein R$^{10}$ and R$^{11}$ are the same as or different from each other and each means hydrogen atom or a C1–C4 alkyl group which may be substituted with an amino group which may be substituted with a halogen atom or a C1–C4 alkyl group; and q means 0 or 1), or an aryl or heteroaryl group which may have a substituent, provided that the following cases are excluded: 1) A and D are both hydrogen atoms; 2) when Y is a nitrogen atom, then T, U, V, X and Y are =C(D$^2$)—, wherein D$^2$ is a hydrogen atom, K and Z are single bonds, A is a hydroxyl group, and B is a p-tolyl group.

2. The compound, the pharmacologically acceptable salt or hydrates thereof according to claim 1, wherein Z is a single bond.

3. The compound, the pharmacologically acceptable salt or hydrates thereof according to claim 1, wherein A is a halogen atom, a C1–C4 alkyl or alkoxy group which may be substituted with a halogen atom, cyano group, —(CO)rNR$^{12}$R$^{13}$ (where R$^{12}$ and R$^{13}$ are the same as or different from each other and each means hydrogen atom or a C1–C4 alkyl group which may be substituted with a halogen atom; and r means 0 or 1) or a C2–C4 alkenyl group or alkynyl group which may have a substituent.

4. The compound, the pharmacologically acceptable salt or hydrates thereof according to claim 1, wherein only one of T, W and Y is a nitrogen atom.

5. A quinoline compound represented by the formula:

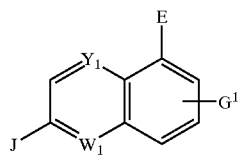
(II)

wherein $Y_1$ and $W_1$ are different from each other and each means a nitrogen atom or =C(D$^3$)— (wherein, D$^3$ is hydrogen atom, halogen atom, hydroxyl group, C1–C4 alkyl group or alkoxy group which may be substituted with a halogen atom, cyano group or —(CO)nNR$^6$R$^7$ (wherein, R$^6$ and R$^7$ are the same as or different from each other and each means a hydrogen atom or a C1–C4 alkyl group which may be substituted with a halogen atom; and n denotes 0 or 1);

E is a halogen atom, cyano group or a C1–C4 alkyl group which may be substituted with a halogen atom;

J is an amino group which may have a protecting group or a carboxyl group which may have a protecting group; and $G^1$ is a hydrogen atom, halogen atom, hydroxyl group, a C1–C4 alkyl group or alkoxy group which may be substituted with a halogen atom, cyano group, —(CO)tNR$^{14}$R$^{15}$ (wherein, R$^{14}$ and R$^{15}$ are the same as or different from each other and each means hydrogen atom or a C1–C4 alkyl group which may be substituted with a halogen atom; and t denotes 0 or 1) or a C2–C4 alkenyl group or alkynyl group which may have a substituent or a salt thereof.

6. A process for producing a compound represented by the formula (IV):

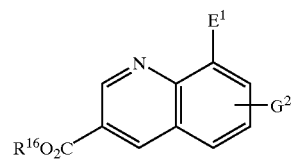
(IV)

wherein E$^1$ is a halogen atom; R$^{16}$ is a carboxyl-protecting group; G$^2$ is a hydrogen atom, halogen atom, hydroxyl group or a C1–C4 alkyl group or alkoxy group which may be substituted with a halogen atom, wherein said method comprises the steps of:

reducing a compound represented by formula (III):

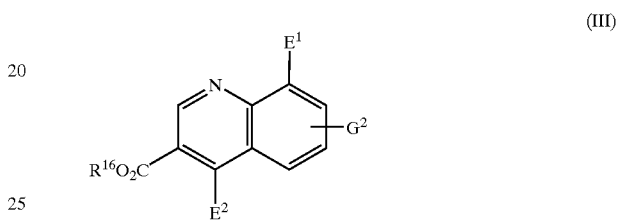
(III)

(wherein E$^1$ is a halogen atom; E$^2$ is chlorine atom or bromine atom; R$^{16}$ is a carboxyl-protecting group; G$^2$ is hydrogen atom, a halogen atom, hydroxyl group, or a C1–C4 alkyl group or alkoxy group which may be substituted with a halogen atom) with tin, zinc or iron; and producing said compound of formula (IV).

7. A pharmaceutical composition comprising:
the compound, the pharmacologically acceptable salt or hydrates thereof as claimed in claim 1 as an active ingredient; and
a pharmaceutically acceptable carrier.

8. A method for treating a disease against which an antiangiogenic effect is efficacious for the treatment, said method comprising:
administering a pharmacologically effective amount of the compound, the pharmacologically acceptable salt or hydrates thereof as claimed in claim 1 to a patient in need thereof.

9. The method according to claim 8, wherein the disease is cancer, cancer-metastasis, diabetic retinopathy, rheumatic arthritis or hematoma.

* * * * *

UNITED STATES PATENT AND TRADEMARK OFFICE
CERTIFICATE OF CORRECTION

PATENT NO. : 6,787,534 B2
DATED : September 7, 2004
INVENTOR(S) : Toru Haneda et al.

It is certified that error appears in the above-identified patent and that said Letters Patent is hereby corrected as shown below:

Title page,
Item [57], ABSTRACT,
Line 6, wherein the ring portion of formula (1) reading "V=U" should read as --V=U--.

Column 2,
Lines 41-49, the ring portion of formula (1) reading "V=U" should read as --V=U--.

Column 8,
Lines 14-19, the ring portion of formula (VII) reading "V=U" should read as --V=U--.

Lines 26-35, the ring portion of formula (VII) reading "V=U" should read as --V=U--.

Columns 9-10,
The ring portion of each of formulae (VIII), (X) and (XI) reading "V=U" should each read as --V=U--.

Column 75,
Lines 28-37, the ring portion of formula (1) reading "V=U" should read as --V=U--.

Signed and Sealed this

Tenth Day of May, 2005

JON W. DUDAS
*Director of the United States Patent and Trademark Office*